(12) United States Patent
Baumgartner et al.

(10) Patent No.: US 10,823,438 B1
(45) Date of Patent: *Nov. 3, 2020

(54) VENT BYPASS SYSTEM

(71) Applicant: Altapure, LLC, Tomahawk, WI (US)

(72) Inventors: Paul Baumgartner, Port St. Lucie, FL (US); Jonathan J. Ricciardi, West Richland, WA (US); Carl L. Ricciardi, Tomahawk, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/561,068

(22) Filed: Sep. 5, 2019

(51) Int. Cl.
  *F24F 7/04* (2006.01)
  *A61L 2/24* (2006.01)

(52) U.S. Cl.
  CPC . *F24F 7/04* (2013.01); *A61L 2/24* (2013.01); *F24F 2221/22* (2013.01)

(58) Field of Classification Search
  CPC ...... F24F 7/04; F24F 7/06; F24F 7/065; F24F 7/08; F24F 7/10; F24F 2221/22; F24F 13/26; F24F 13/32; F24F 13/02; F24F 13/0218; F24F 13/0236; F24F 13/0272; F24F 13/084; A61L 2/24
  See application file for complete search history.

(56) References Cited

U.S. PATENT DOCUMENTS

| | | | | |
|---|---|---|---|---|
| 2,939,378 A | * | 6/1960 | Allen | F24F 13/0218 454/63 |
| 3,433,461 A | * | 3/1969 | Scarpa | B06B 1/0666 366/112 |
| 3,485,671 A | * | 12/1969 | Stephens | F24F 13/02 134/7 |
| 3,540,719 A | * | 11/1970 | Jensen | A61G 13/124 5/647 |
| 3,729,138 A | * | 4/1973 | Tysk | B05B 17/0607 239/102.2 |
| 4,109,863 A | * | 8/1978 | Olson | A61M 15/0085 239/102.2 |
| 4,163,650 A | * | 8/1979 | Watson | B03C 3/36 15/339 |
| 4,366,125 A | * | 12/1982 | Kodera | A61L 2/10 422/20 |
| 4,452,169 A | * | 6/1984 | Matsuda | B05C 7/02 118/317 |
| 4,512,951 A | * | 4/1985 | Koubek | A01N 59/00 422/33 |
| 4,829,882 A | * | 5/1989 | Jackson | E02D 31/008 236/49.1 |

(Continued)

*Primary Examiner* — Avinash A Savani
*Assistant Examiner* — Martha M Becton
(74) *Attorney, Agent, or Firm* — Donald J. Ersler

(57) ABSTRACT

A vent bypass system is created by forming a bypass hole through a vent cover door of two adjacent vent cover doors. A tube flange is extended from a bottom surface of the vent cover door, concentric with the bypass hole. A first vent cover door covers an entry vent and the second vent cover door covers an exit vent. One end of a flexible tube is secured to one of the two tube flanges and the other end of the flexible tube is secured to the other one of the two tube flanges. Air/gas blown into the room will bypass circulating through the room by going through the flexible tube from the entry vent to the exit vent. Any suitable means to connect the various vents can be used, such as, but not limited to any pipe, hose, tube, conduit, or the like.

12 Claims, 23 Drawing Sheets

(56) References Cited

U.S. PATENT DOCUMENTS

| | | | | |
|---|---|---|---|---|
| 4,886,532 A * | 12/1989 | Zimmerman | D01H 11/005 | 55/302 |
| 4,902,315 A * | 2/1990 | Spicer | B01D 46/42 | 454/238 |
| 4,952,370 A * | 8/1990 | Cummings | A61L 2/20 | 422/27 |
| 4,955,344 A * | 9/1990 | Tatsumi | E02F 9/2296 | 123/352 |
| 4,976,259 A * | 12/1990 | Higson | A61M 15/0085 | 128/200.14 |
| 5,165,732 A * | 11/1992 | Townsend | F16L 13/163 | 126/307 R |
| 5,281,246 A * | 1/1994 | Ray | B01D 46/002 | 55/302 |
| 5,300,260 A * | 4/1994 | Keshet | B05B 17/0615 | 239/102.2 |
| 5,383,973 A * | 1/1995 | Curry, Jr. | B08B 6/00 | 134/22.1 |
| 5,438,729 A * | 8/1995 | Powell | B08B 9/0436 | 15/304 |
| 5,702,296 A * | 12/1997 | Grano | F24F 7/013 | 165/54 |
| 5,724,701 A * | 3/1998 | Jones | B01D 46/0032 | 15/304 |
| 5,868,858 A * | 2/1999 | Creed | B08B 9/0436 | 134/21 |
| 5,873,919 A * | 2/1999 | Vross | B01D 46/00 | 126/343.5 A |
| 5,878,355 A * | 3/1999 | Berg | B01J 13/0095 | 427/212 |
| 5,925,966 A * | 7/1999 | Riftin | G10K 11/006 | 310/311 |
| 5,966,773 A * | 10/1999 | Jones | B01D 46/0032 | 15/304 |
| 6,035,484 A * | 3/2000 | Jones | B01D 46/0032 | 15/304 |
| 6,047,714 A * | 4/2000 | Akazawa | B08B 9/043 | 134/22.12 |
| 6,102,992 A * | 8/2000 | Berg | B01J 13/0095 | 261/29 |
| 6,143,048 A * | 11/2000 | Comproni | B01D 46/0036 | 118/326 |
| 6,372,052 B1 * | 4/2002 | Jones | B01D 46/0023 | 134/21 |
| 6,395,047 B1 * | 5/2002 | Smith | B08B 15/002 | 454/187 |
| 6,461,235 B2 * | 10/2002 | Rutler | F24F 13/085 | 454/289 |
| 6,575,827 B1 * | 6/2003 | Rutler | F24F 13/085 | 454/289 |
| 6,616,720 B1 * | 9/2003 | Smith | B08B 15/002 | 454/187 |
| 6,749,499 B1 * | 6/2004 | Snyder | F24F 13/085 | 454/284 |
| 6,979,359 B2 * | 12/2005 | Laiti | B01D 46/0023 | 454/187 |
| 7,185,868 B2 * | 3/2007 | Wang | A47F 5/04 | 248/125.1 |
| 7,354,551 B2 * | 4/2008 | Mielnik | A61L 2/208 | 422/32 |
| 7,566,354 B2 * | 7/2009 | Ryan | B01D 46/008 | 55/385.1 |
| 8,001,909 B2 * | 8/2011 | Overgaard | A47B 9/06 | 108/147 |
| 8,298,057 B2 * | 10/2012 | Huber | F04D 29/424 | 454/338 |
| 8,359,984 B1 * | 1/2013 | Wolf, II | A61L 9/14 | 108/147.19 |
| 8,460,417 B2 * | 6/2013 | Reid | B08B 15/04 | 55/356 |
| 8,506,900 B1 * | 8/2013 | Ricciardi | A61L 2/04 | 422/292 |
| 8,844,578 B2 * | 9/2014 | Pinkalla | F24F 13/0254 | 138/107 |
| D745,129 S * | 12/2015 | Nakagawa | D23/364 | |
| 9,211,354 B2 * | 12/2015 | Hill | A61L 2/22 | |
| 9,376,857 B1 * | 6/2016 | Baumgartner | F16M 11/38 | |
| 9,468,958 B2 * | 10/2016 | Hammers | B08B 15/00 | |
| 9,498,805 B2 * | 11/2016 | Hammers | B08B 15/002 | |
| 9,505,041 B2 * | 11/2016 | Hammers | B23K 37/08 | |
| 9,505,042 B2 * | 11/2016 | Hammers | B08B 15/02 | |
| 9,604,266 B2 * | 3/2017 | Hammers | F24F 7/007 | |
| 9,605,864 B2 * | 3/2017 | Pinkalla | F16L 11/02 | |
| 9,605,865 B2 * | 3/2017 | Pinkalla | F24F 13/0254 | |
| 9,612,033 B2 * | 4/2017 | Pinkalla | F16L 11/10 | |
| 9,927,139 B2 * | 3/2018 | Pinkalla | F24F 13/0218 | |
| 9,927,140 B2 * | 3/2018 | Pinkalla | F24F 13/0218 | |
| 9,943,620 B2 * | 4/2018 | Bender | C01B 11/024 | |
| 10,029,274 B1 * | 7/2018 | Baumgartner | A61L 9/14 | |
| 10,094,128 B2 * | 10/2018 | Hartman | E04G 23/0203 | |
| 10,195,632 B1 * | 2/2019 | Baumgartner | G01K 7/02 | |
| 10,213,803 B1 * | 2/2019 | Baumgartner | G01K 7/02 | |
| 10,228,155 B2 * | 3/2019 | Harman | F24F 13/085 | |
| 10,322,431 B1 * | 6/2019 | Baumgartner | B05B 17/0607 | |
| 10,436,462 B1 * | 10/2019 | Baumgartner | F24F 3/16 | |
| 10,480,813 B2 * | 11/2019 | Pinkalla | F24F 7/065 | |
| 10,588,245 B2 * | 3/2020 | Lucia | H05K 7/20745 | |
| 10,596,284 B2 * | 3/2020 | Bender | A61L 9/12 | |
| 2002/0077059 A1 * | 6/2002 | Rutler | F24F 13/085 | 454/289 |
| 2004/0146437 A1 * | 7/2004 | Arts | A61L 9/015 | 422/186.07 |
| 2004/0184950 A1 * | 9/2004 | McVey | A61L 2/24 | 422/4 |
| 2004/0262240 A1 * | 12/2004 | Oke | C02F 1/72 | 210/758 |
| 2005/0042130 A1 * | 2/2005 | Lin | A61L 2/22 | 422/33 |
| 2006/0008379 A1 * | 1/2006 | Mielnik | A61L 2/208 | 422/32 |
| 2007/0053789 A1 * | 3/2007 | Ricciardi | A61L 2/22 | 422/28 |
| 2008/0178779 A1 * | 7/2008 | Agee | A47B 9/04 | 108/147 |
| 2008/0202617 A1 * | 8/2008 | Baek | F16L 11/081 | 138/118 |
| 2010/0233020 A1 * | 9/2010 | Klaassen | A61L 2/24 | 422/20 |
| 2011/0114744 A1 * | 5/2011 | Ricciardi | A61L 9/14 | 239/4 |
| 2011/0123394 A1 * | 5/2011 | Plantinga | A61L 2/18 | 422/28 |
| 2012/0125472 A1 * | 5/2012 | Pinkalla | F24F 7/065 | 138/96 R |
| 2012/0282153 A1 * | 11/2012 | Cheong | F22B 1/282 | 422/292 |
| 2014/0000744 A1 * | 1/2014 | Pinkalla | F16L 3/18 | 138/103 |
| 2014/0007971 A1 * | 1/2014 | Pinkalla | F16L 3/18 | 138/172 |
| 2014/0261835 A1 * | 9/2014 | Pinkalla | F24F 7/065 | 138/107 |
| 2016/0058901 A1 * | 3/2016 | Bender | C01B 11/024 | 204/157.3 |
| 2017/0159965 A1 * | 6/2017 | Pinkalla | F24F 13/0254 | |
| 2017/0159966 A1 * | 6/2017 | Pinkalla | F24F 13/0254 | |
| 2018/0078979 A1 * | 3/2018 | Intravatola | B08B 15/00 | |
| 2018/0093003 A1 * | 4/2018 | Bender | A61L 2/20 | |
| 2018/0180319 A1 * | 6/2018 | Pinkalla | F16L 11/00 | |

* cited by examiner

VENT BYPASS SYSTEM

CROSS-REFERENCES TO RELATED APPLICATIONS

This is a continuation-in-part patent application, which takes priority from patent application Ser. No. 14/886,124, filed on Oct. 19, 2015 and is herein incorporated by reference in its entirety.

BACKGROUND OF THE INVENTION

Field of the Invention

The present invention relates generally to disinfecting a hospital room and more specifically to a vent bypass system, which covers and connects inbound air/gas vents to other covered outbound air/gas vents, which can reduce, and eliminate, the movement of any air, gas, or aerosol, from moving into or out of any sealed or closed room(s) or space(s). Further, the present invention relates generally to the cleaning and decontamination of the interior of various air duct(s) and/or HVAC part(s) by connecting any air entry vent(s) and air exit vent(s) in room(s) and area(s) of a building(s) using one or more vent bypass system(s) to connect the various ductwork and/or supply and return air duct(s) in an HVAC system(s), and allowing deployed airborne agent(s) to be flowed through the interconnected system of various connected air duct(s), conduit(s), and/or any other HVAC part(s) and related equipment(s) for their sanitization, disinfection, sterilization, and/or decontamination. Additionally, the present invention relates generally to an enhanced aerosol and/or vapor generator design where the generated aerosol and/or vapor and gas(s) is flowed into at least one pressurized chamber and then flowed into various, enclosure(s), space(s), conduit(s) and/or airduct(s), overcoming a delinquency in many aerosol and/or vapor generator designs where an effective air/gas(s) flow is not provided or generated to deploy any, aerosol, gas(s), and/or vapor(s), effectively into any, enclosure(s), space(s), conduit(s) and/or air duct(s) with long horizontal and/or vertical runs. Finally, the present invention also relates to an enhanced vent bypass system that can treat, decontaminate, dehumidify, remove unwanted vapor(s) or gas(s), and/or dry, various air duct(s), conduit(s), HVAC system(s), and/or any other HVAC part(s) and related equipment(s).

Discussion of the Prior Art

A vent cover is placed over a heating/cooling vent, which is a portion of a HVAC system, when a hospital room is disinfected. Automation of the vent covering process speeds up the disinfection process. U.S. Pat. No. 8,359,984 (984 patent) to Wolf I I et al. discloses a portable automated vent cover. U.S. Pat. No. 8,359,984 is herein incorporated into this patent application by reference in its entirety. However, the vent cover door of the '984 patent does not always release from a vent opening without manual intervention on the part of an operator, because the vacuum in the vent retains the vent cover door against the vent opening. U.S. Pat. No. 9,789,508 to Baumgartner et al. and U.S. Pat. No. 7,641,130 to Ricciardi et al. are hereby incorporated by reference in their entirety.

Accordingly, there is a clearly felt need in the art for a vent bypass system that covers and connects inbound air/gas vents to other covered outbound air/gas vents, which can reduce, and eliminate, the movement of any air, gas, or aerosol, from moving into or out of any sealed or closed room(s) or space(s).

SUMMARY OF THE INVENTION

The present invention provides a vent cover system, which allows a vent cover door to be withdrawn from a vent opening without operator intervention. The vent cover system preferably includes a portable automated vent cover and the vacuum release door. The portable automated vent cover includes a drive system, a telescoping tube, a vent cover door and a collapsible mobile tripod. The telescoping tube includes an outer support tube and an inner cover tube that slides within the outer support tube. A bottom of the outer support tube is attached to the collapsible mobile tripod. The drive system is retained at a top of the outer support tube. The drive system moves the inner cover tube along a vertical axis. However, the drive system may be replaced with a manual lift system to provide a portable manually operated vent cover.

The vacuum release door preferably includes a vacuum door plate, a plurality of retention pins, a sealing gasket and a tube flange. The sealing gasket includes the same outer perimeter as the vacuum door plate. A vacuum break opening is formed through a center of the vent cover door. The vacuum break opening can be any suitable size and the vacuum release door may drop any suitable distance. The sealing gasket is preferably attached to a top of the vacuum door plate. A plurality of pin holes are formed around a perimeter of the vacuum door plate to slidably receive the plurality of retention pins. Each retention pin includes a head portion and a pin portion. The pin portion extends from the head portion. The pin portion is inserted through the plurality of pin holes and attached to the vent cover door with fasteners or the like. The tube flange includes a tube opening, which is sized to snugly receive a top end of the inner cover tube. The tube flange is attached to a bottom of the vacuum door plate.

In use, the vent cover door is raised, until a peripheral sealing ring on a top of the vent cover door seals around a perimeter of a vent opening. When an attempt is made to lower the vent cover door from the vent opening, the inner cover tube will first cause a seal to be broken between the vacuum door plate and the vent cover door. After the seal is broken, the plurality of retention pins will experience a downward force, which will cause a seal between the vent cover door and the vent opening to be broken. The vent cover system makes it easier to break a seal between the vent opening and the vent cover door, because the perimeter of the vacuum release door is much smaller than a perimeter of the vent cover door. Consequently, it is easier to break a small length seal than a larger length seal.

A vent bypass system is created by forming a bypass hole through a vent cover door of two adjacent vent cover doors. A tube flange is extended from a bottom surface of the vent cover door, concentric with the bypass hole. A first vent cover door covers an entry vent and the second vent cover door covers an exit vent. One end of a flexible tube is secured to one of the two tube flanges and the other end of the flexible tube is secured to the other one of the two tube flanges. Gas (air, gas, aerosol, vapor or gaseous substance) blown into the room will bypass circulating through the room by going through the flexible tube from the entry vent to the exit vent. Any suitable means to connect the various vents can be used, such as, but not limited to any pipe, hose, tube, conduit, or the like. The vent bypass system will also keep a balance in a circulating system by not sealing up a normal flow pattern through the room.

It is preferred, without limitation, that this connection or communication between these vents and their covers or sealed covers, is complete, without any leaking, or at least without any substantially effective leaking, of substances such as, but not limited to any, gas(s), vapor(s), and/or aerosol(s).

This can be, without limitation, accomplished by combining and effectively connecting or interfacing one or more of any means such as, but not limited to, any effective, channeling, piping, hose, and/or ducting, (Herein called "Hose"), with or to, one or more of any effective means to cover and/or seal one or more of any "entry vent(s)" and "exit vent(s)" (Herein called "Vent cover(s)"). Without being limited, the one or more "vent cover(s)" can be, without limitation, one or more of any effective means to cover, close, seal, and/or seal, around and/or to, one or more of any "entry vent(s)" and "exit vent(s)". It is preferred, without limitation, that the "vent cover(s)" is any vent cover plate, and more preferably any vent cover door.

It is preferred, without limitation, that the one or more hose(s) are effectively interfaced and connected to the various vent cover(s), all in a manner known to those skilled in the art. It is even more preferred, without limitation, that these one or more hose(s) have an easily releasable and effectively air-tight connection(s) to the vent cover(s), all in a manner known to those skilled in the art. Without being limited, the hose(s) may connect directly or indirectly to any vent cover(s) in one or more of any location(s) or position(s). It is preferred, without limitation, that the location(s) or position(s) are at least effective. Also, and without being limited, the hose(s) may connect directly or indirectly to the vent cover(s), in one or more of any ways such as, but not limited to using any, connected component(s), structure(s), pipe(s), connection(s), connector(s), male and female connector(s), conduit(s), hose(s), and the like (Herein called "Hose Connection(s)").

Any hose(s) known to those skilled in the art, may be used in the present invention. Without being limited, each hose(s) that is utilized, can have any effective and suitable, length, diameter, width, flexibility, material, shape, construction, and design. Without being limited, one or more of any suitable and effective hoses may be used in the same room(s) or area(s).

The diameter of the various hoses can vary for various reasons including, but not limited to, the flow rate or volume of air and/or gas(s), leaving and/or entering the various vents. It is preferred, without limitation, that the hose(s) have a diameter between less than one-quarter (0.25) inch to about eight (8) inches or more. It is more preferred, without limitation, that the hose(s) have a diameter between about one (1) inch to about six (6) inches. It is even more preferred, without limitation, that the hose(s) have a diameter between about one (1) inch to about three (3) inches. It is very preferred, without limitation, that the hose(s) have a diameter of about two (2) inches.

Without being limited, the hose(s) may be constructed in various ways such as, but not limited to, being smooth or ribbed. The hose(s) may also be made from one or more of any material(s). It is preferred, without limitation, that the hose(s) are constructed from any flexible ribbed polypropylene that is suitable.

The one or more of any "entry vent(s)" and "exit vent(s)", can be located in one or more of any location(s), space(s), and/or room(s). It is preferred, without limitation, that the "entry vent(s)" and "exit vent(s)", are located in the same, or at least effectively connected, location(s), space(s), and/or room(s).

Without being limited, this new apparatus and method, can be used to, without limitation, balance, equalize, eliminate, and/or effectively reduce, any positive and/or negative air or atmospheric pressure within any room(s), space(s), and/or sealed room(s). However, it is preferred, without limitation, that this new apparatus and method, is used to effectively reduce or even effectively eliminate, the movement of one or more substance such as, but not limited to any, air, gas(s), vapor(s), and/or aerosol(s) from entering and/or leaving the one or more, room(s), space(s), and/or targeted area(s), in which the "entry vent(s)" and "exit vent(s)" are located. It is also more preferred, without limitation, that this new apparatus and method is used to effectively seal any "entry" and "exit" vent(s) or port(s) in a sealed area or room, and carry at least some, but preferably all, of the air, gas(s), or other substances, via suitable hose(s), from the one or more of any vent(s) meant to supply any, air, gas(s), or other substances, into one or more of any, room(s), space(s), and/or sealed room(s), to one or more of any other vent(s) that are meant to remove or exhaust any, air, gas(s), or other substances, out of the same one or more room(s) or space(s), or at least any effectively connected, room(s), space(s), and/or sealed room(s) or space(s).

Any vent cover design(s) known in the art, and any one or more of any hose(s) connected to any of the one or more vent cover(s), can be interfaced or connected to one or more of any effective means to effectively, position, cover, and/or seal, the "entry vent(s)" and "exit vent(s)".

Broadly, and without limitation, one or more of any means, such as, but not limited to any, poles, masts, telescoping tubes, support structure(s), and/or support structure(s), that can be adjusted and/or moved for any length, height, and/or distance, may be directly and/or indirectly connected to one or more of any vent cover(s), and used to apply, transfer, or help to transfer, one or more of any effective pressure(s) and/or force(s), to the vent cover(s), and/or any connecting sealing material(s), to help them cover, and/or seal on and/or around, one or more of any entry vent(s) and/or exit vent(s). The one or more vent cover(s) may be moved into or out of any location or position, in any effective manner, such as but not limited to, mechanically, manually, automatically, automated, and/or non-automated. It is preferred, without limitation, that the various vent cover(s) are positioned or moved into any effective location, with an automated vent cover apparatus described in U.S. Pat. No. 8,359,984 (Wolf I I et al.).

In a preferred detailed summary aspect, and without limitation, one or more of any vent cover(s) can be also be attached to any manually extendable means known to those in the art such as, but not limited to any, manually extended pole(s) that can be effectively arrested or locked at any length or height (Herein called "Pole"), and can hold one or more vent cover(s) on its end. The pole can be, without limitation, manually extended and arrested or locked at any effective length, and used to manually position the vent cover(s), and their accompanying one or more connected hose(s) over, around, and/or against, the "entry vent(s)" and/or "exit vent(s)". It is preferred, without limitation, that a suitable vent cover with one or more connecting hose(s), is suitably connected to this type of manually adjusted pole, and an end of this pole, preferably one or more of any effective member or end of any member on the opposing side, without the vent cover, is interfaced with a surface such as, but not limited to any, floor, and the pole is manually extended in length until the connected vent cover is effectively positioned and covering and/or sealing the vent cover(s).

In another more preferred summary aspect, and without limitation, one or more of any vent cover(s) can also be suitably attached to any automated and extendable means such as, but not limited to, the one that has already been disclosed in U.S. Pat. No. 8,359,984 (Wolf I I et al.). The automated lifting and lowering means described in the U.S. Pat. No. 8,359,984 (Wolf I I et al.), can also be used, without limitation, to effectively locate one or more vent cover(s), and their accompanying one or more connected hoses, over, around, and/or against, the "entry vent(s)" and/or "exit vent(s)". It is preferred, without limitation, that a suitable vent cover with one or more connecting hose(s), is suitably connected to an apparatus as described in U.S. Pat. No. 8,359,984 (Wolf I I et al.), and the vent cover is positioned using this automated device so that one or more targeted vent opening(s) is effectively covered and/or sealed by the vent cover(s).

Without being limited, the various hose(s) can be added or removed from the various vent cover(s) at any suitable time. It is preferred, without limitation, that the various hose(s) are added to the various vent cover(s), before the various vent cover(s) are raised into position to cover and/or seal the "entry vent(s)". It is also preferred, without limitation, that the various hoses are removed from the various vent cover(s), after the vent cover(s) are lowered and uncovered and/or unsealed from the "entry vent(s)" and the "exit vent(s)".

Certain spaces or areas such as, but not limited to any, hospital room(s), operating room(s), clean room(s), clean area(s), laboratory area(s), and/or production area(s), can have one or more "entry" vent(s) and "exit" vent(s) that may require being covered and/or sealed with the improvements disclosed in the present invention. Without being limited, this can influence the number of hoses and associated components that are used. One or more of any suitable and effective combination(s) of the one or more vent cover(s), hose(s), and their various connection(s), may be made.

In one example, and without limitation, a hospital room can have one [1] "entry" vent, and two [2] "exit" vent(s). In this example, a vent cover is positioned and effectively sealed into place over the "entry" vent, via any suitable automatic, mechanical, or manual means, known in the art. Two [2] hose(s) are suitably interfaced and connected with this "entry" vent cover, with any suitable hose connection device known to those skilled in the art. A vent cover is also positioned and effectively sealed into place over each of the other two [2] "exit" vents, via any suitable automatic, mechanical, or manual means, known in the art. One of the hoses that extends from the "entry" vent cover is suitably interfaced and connected with one of the "exit" vent covers, with any suitable hose connection device known to those skilled in the art. One of the other hoses that extends from the "entry" vent cover is also suitably interfaced and connected with one of the other "exit" vent covers, with any suitable hose connection device known to those skilled in the art.

In another example, and without limitation, a hospital room can have two [2] "entry" vents, and one [1] "exit" vent(s). In this example, a vent cover is positioned and effectively sealed into place over each of the "entry" vents, via any suitable automatic, mechanical, or manual means, known in the art. One [1] hose is suitably interfaced and connected with each of these "entry" vent covers, with any suitable hose connection device known to those skilled in the art. A vent cover is also positioned and effectively sealed into place over the one [1] "exit" vent, via any suitable automatic, mechanical, or manual means, known in the art. Each of the hoses that extends from each of the "entry" vent covers is suitably interfaced and connected with the one "exit" vent cover, with any suitable hose connection device known to those skilled in the art.

According to an embodiment, and without limitation, the vent cover can also have any effective, shape, geometry, volume, height, length, width, and depth. The vent cover can also be modified to effectively cover and seal around objects such as, but not limited to any, smoke detectors, fire alarms, lights, and the like.

Accordingly, it is object of the present invention to provide a vent bypass system, which is positioned, either manually, or via any effective automated means, over one or more of any inbound and/or outbound air/gas vents, and rerouting the airflow from one or more of any "entry" vent(s) to one or more of any "exit" vent(s), through one or more of any effective hose connection(s), thus preventing unwanted airflow into or out of any room(s) or targeted space(s). Any one or more combination(s), of one or more of any components such as, but not limited to any, air/gas entry vent(s), air/gas exit vent(s), vent cover(s), hose(s), and hose coupling device(s), may be connected in any number of ways, all in a manner known to those skilled in the art.

An apparatus and method of an embodiment of the present invention, briefly summarized and without limitation, comprises the use of a vent bypass system to provide the treatment of, and more preferably and without limitation, the decontamination of, various surfaces inside of various connected and/or indirectly connected ductwork, air ducts, connected air supply ducts, air return ducts, HVAC equipment, entire HVAC systems and associated ducting, and/or any other connected and/or related parts that can be, without limitation, connected to various parts and equipment used for heating, ventilation, cooling, movement, distribution, and/or filtering, of air and/or gas(s), that is supplied to one or more room(s), various rooms and/or area(s) in a building and/or home.

The problem with the current art, and without being limited, is that one cannot flow airborne agent(s) such as, but not limited to any, aerosol(s), gas(s), and/or vapor(s), through various air distribution and/or HVAC related part(s), such as, but not limited to any, air duct(s), air duct system(s), air supply duct(s), air supply trunk line(s), air return trunk line(s), vent component(s), air outlets, air inlets, air return duct(s), air shaft(s), hose(s) (40)(4380), blower(s), fan(s), valve(s), means to channel, stop, restrict, and/or direct air, and/or any other conduit(s) to move any air and/or gas(s) through, to, and/or from, one or more of any room(s) (4410), area(s), and/or building(s), HVAC part(s) and component(s) used to heat, cool, filter, and/or move air/gas(s) throughout a home or building, and more specifically through the connected and/or interconnected air duct system of an entire building or even one or more of any isolated area(s) of a building, because the various air supply duct(s) and their associated air supply vent(s), will supply airflow into one or more various room(s) and/or area(s), and the return and/or exit air vent(s) will allow air from these same room(s) and/or area(s) to exit the said room(s), and preferably and without limitation return it back to the said various HVAC equipment, thus posing problems known to those skilled in the art, such as, but not limited to, the said room(s) and/or area(s) will fill with the deployed and airborne agent(s), and any return or exit air ducts may not be exposed to an effective quantity and/or concentration of the deployed and airborne agent(s) for any effective treatment. Without being limited, the said deployed and airborne agent(s) can be used for purposes such as, but not limited to any, cleaning, sanitization, disinfection, sterilization, and/or decontamination, of the interior and/or exterior of the said various, air distribution duct(s), air duct(s) and/or HVAC related part(s) and component(s).

More specifically, and without limitation, the problem with the current art, and without being limited, is that airborne agent(s) such as, but not limited to any, aerosol(s), gas(s), and/or vapor(s), when deployed into any air supply ducts, will eventually flow into the various room(s) and/or area(s) in any building or home, through the various air supply vents located in these various room(s) and/or area(s). In many situations, and without being limited, this is not desired for various reasons known to those skilled in the art. In addition, and without limitation, it would be time consuming and larger amounts of airborne agent(s) would need to be used to fill these various rooms and/or area(s) with an effective amount and/or concentration of the said airborne agent(s) so that the airborne agent(s) can effectively flow from these room and/or area(s) and effectively treat the various air exit and/or air return vent(s) located in these various room(s) and/or area(s) as well as the various directly and/or indirectly connected air return and/or air exit duct(s) in the air duct system(s). Without being limited, the air supply duct(s) and air supply vent(s) can be any duct(s) and vent(s) that can supply air flow and/or deployed and airborne agent(s) to any room(s) and/or area(s), and the exit and/or return vent(s) and any connected air duct(s) can be any vent(s) and duct(s) that can allow airflow and/or deployed and airborne agent(s) to leave any room(s) and/or area(s).

Without being limited, by using the vent bypass system in the various room(s) and/or area(s) the one or more supply air duct(s) can be effectively connected to and communicate with the one or more return air duct(s), and more specifically the various room air supply vent(s) that connect with the various supply air duct(s) are effectively sealed and effectively connected via one or more of any suitable hose(s) and/or conduit(s) to the various room air return and/or exit vent(s) that connect with the various air return and/or air exit duct(s), thus allowing the air and the deployed agent(s) in the various air duct(s) and/or air duct system, to bypass the one or more room(s) and instead flow through the various conduit(s) and air ducts, and also preferably and without limitation, the various HVAC equipment and parts, that are all, preferably and without limitation, effectively connected together.

The present invention also describes, and without limitation, an enhanced vent bypass system that includes any suitable and effective means including, but not limited to any means to, filter air/gas(s), dehumidify air/gas(s), subject air/gas(s) to UV light, move, flow, blow and/or pump air/gas(s) and/or deployed agent(s), as well as any suitable and effective means to deploy, disperse, and/or administer any deployed agent(s), that can be and/or are moved and/or flowed though various, area(s), space(s), air/gas(s) duct(s), air/gas(s) shaft(s), HVAC system(s), HVAC part(s) and equipment(s), including the one or more enhanced vent bypass system(s).

Another problem with the current art is that many, aerosol generator(s), gas generator(s), and/or vapor generator(s), product(s) lack the ability or means to effectively treat remote location(s) and/or conduit(s) and/or air duct(s) with complex geometry(s), horizontal runs, and/or vertical runs, of various design complexities and/or long lengths, all in a manner known to those skilled in the art.

The present invention addresses these shortcomings, by directing, piping, and/or channeling, preferably and without limitation, in any suitable and effectively sealed manner, the generated vapor(s), gas(s), and/or aerosol(s), into at least one aerosol(s), gas(s), and/or vapor(s) collection chamber(s) and/or agent flow compartment(s), which is connected to and communicates with at least one effective, blower(s), fan(s), and/or air pump(s), and where the said collection chamber(s) and/or agent flow compartment(s) can directly and/or indirectly removably communicate and/or connect with various, enclosure(s), chamber(s), room(s), space(s), conduit(s), HVAC equipment, vent bypass system(s), air shaft(s), and/or air duct(s), to effectively flow the generated aerosol(s), gas(s), and/or vapor(s), into these various space(s), location(s), and/or area(s) to coat and/or treat their various surfaces.

These and additional objects, advantages, features and benefits of the present invention will become apparent from the following specification.

DETAILED DESCRIPTION OF THE PREFERRED EMBODIMENTS

Figure 6:
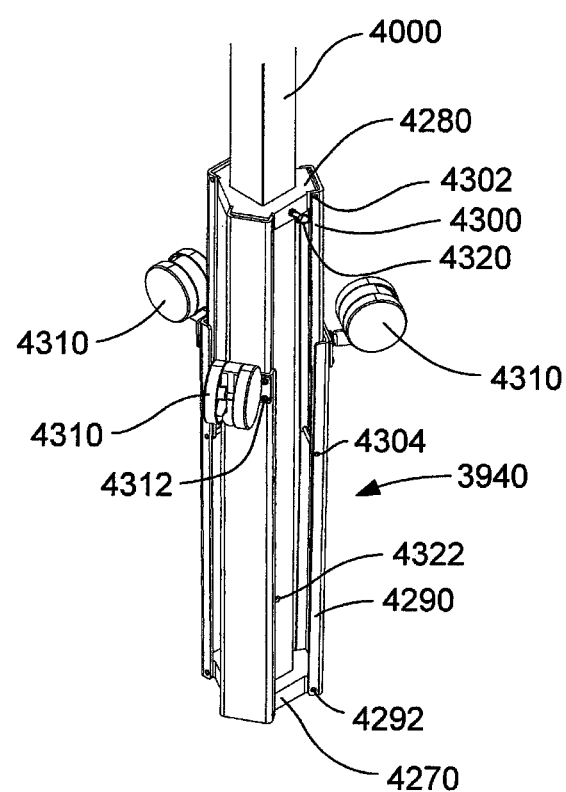
FIG. 6 is an enlarged perspective view of a mobile tripod of a portable automated vent cover in a collapsed orientation.
Figure 7:
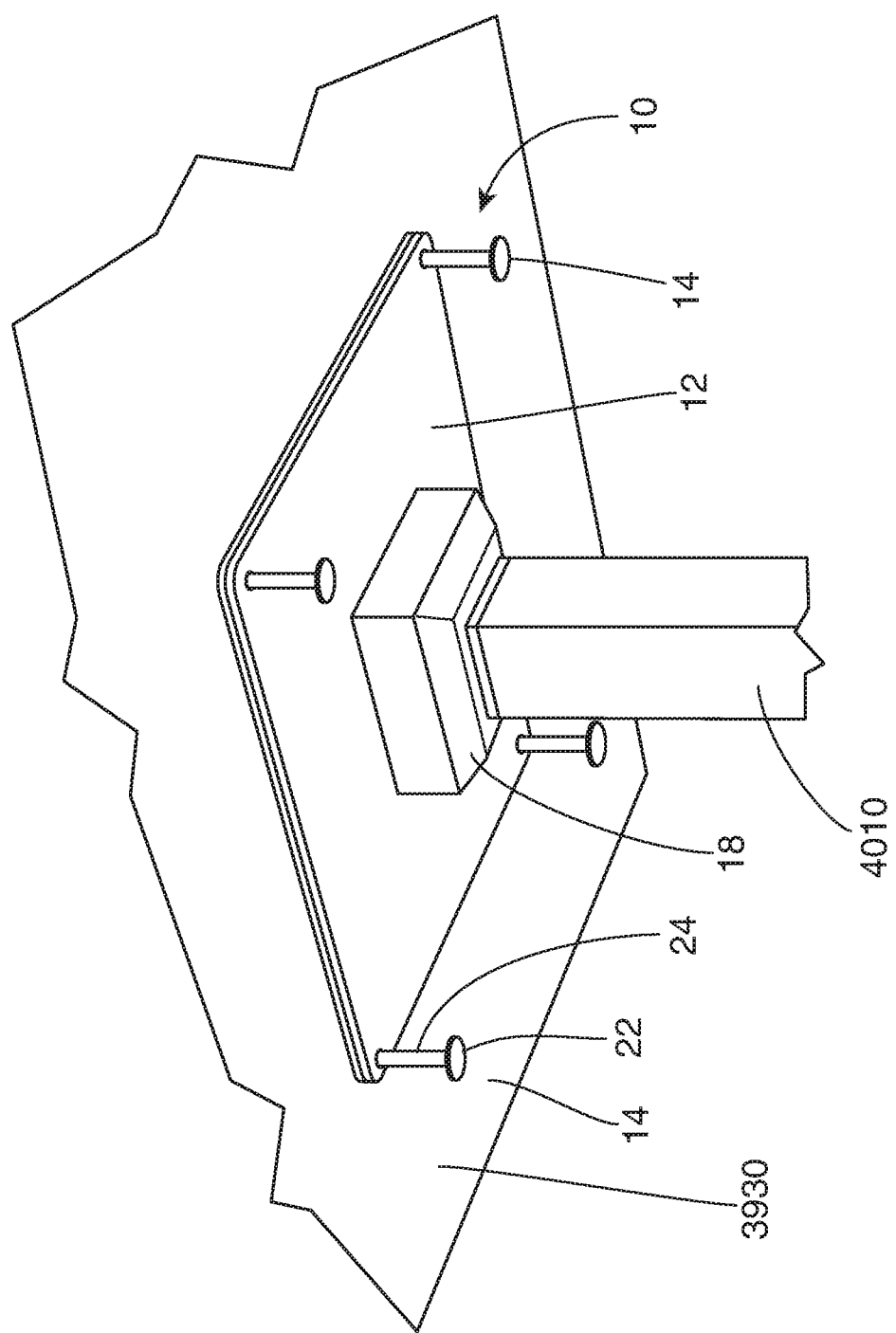
FIG. 7 is a bottom perspective view of a vacuum release door in contact with a vent cover door of a vent cover system in accordance with the present invention.
Figure 10:
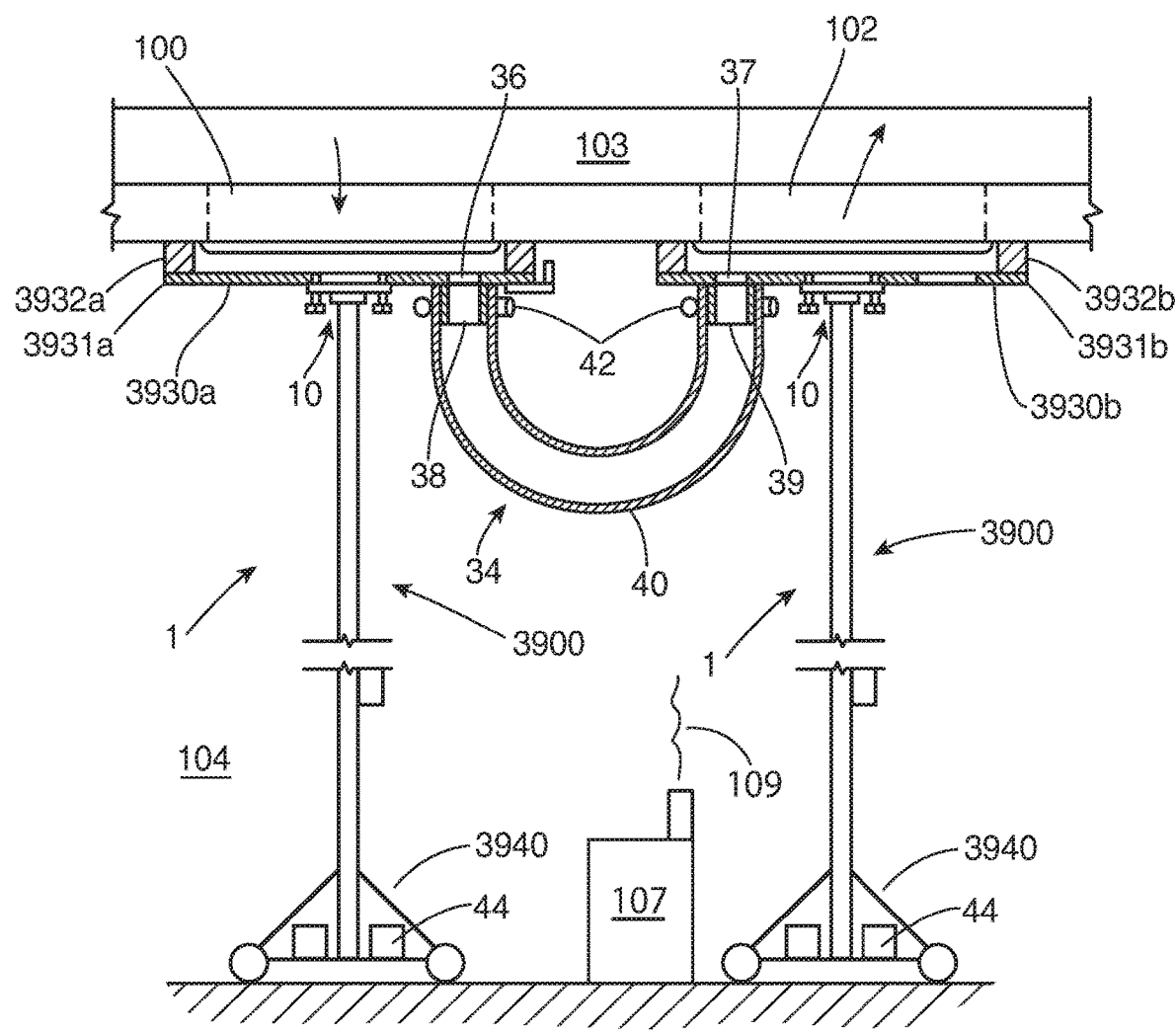
FIG. 10 is a side partially cross sectional view of a first vent cover system adjacent to a second vent cover system connected to each other with a vent bypass system in accordance with the present invention.
Figure 11:
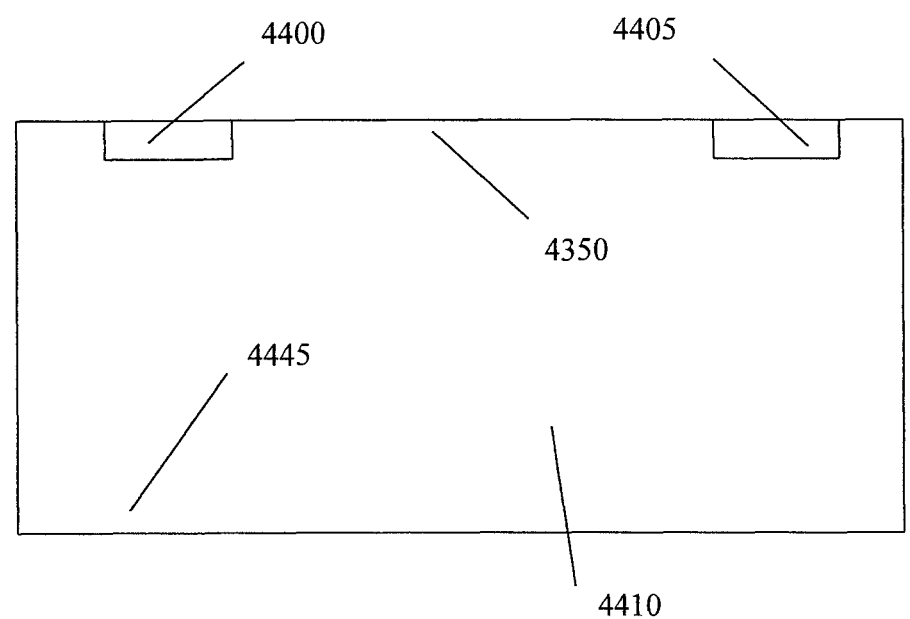
FIG. 11 is a side view of a treated room or space with at least one gas entry vent and at least one gas exit vent of a vent bypass system in accordance with the present invention.

With reference now to the drawings, and particularly to FIG. 7, there is shown a perspective view of a vacuum release door (10) in contact with a bottom of a vent cover door (3930) of a portable automated vent cover 3900. With reference to FIG. 10), a vent cover system (1) preferably includes the portable automated vent cover (3900) and the vacuum release door (10). With reference to FIGS. 1-6, the portable automated vent cover (3900) preferably includes a drive system (3910), a telescoping tube (3920), a vent cover door (3930) and a collapsible mobile tripod (3940). The drive system (3910) preferably includes a drive motor (3950), a gear box (3960), a drive housing (3970), an up-relay (3980) and a down-relay (3990). The up and down relays are preferably double pole/double throw relays. However, the drive system (3910) could be replaced with any suitable manual lift system (not shown). The manual lift system may be locked to any appropriate height. The telescoping tube (3920) includes an outer support tube (4000), an inner cover tube (4010), a rack gear (4020) and a stop collar (4030). However, other types of extendable supports besides telescoping tube (3920) may also be used. The drive motor (3950) drives an input of the gear box (3960) and an output shaft (4040) is driven by an output of the gear box (3960). A pinion gear (4050) is retained on the output shaft (4040) and the rack gear (4020) is driven by through the pinion gear (4050). The gear box (3960) reduces the speed of the drive motor (3950). Small electric motor gear boxes are well known in the art and need not be explained in detail. The drive motor (3950) is preferably a DC motor, but other motors could also be used. The drive housing (3970) includes a first housing half (4060) and a second housing half (4070). Each end of the output shaft (4040) is rotatably supported by the first and second housing halves. The first housing half (4060) includes a first tube slot (4080) and the second housing half (4070) includes a second tube slot (4090). The first and second tube slots are sized to receive an outer perimeter of the outer support tube (4000). The first and second housing halves are secured to the inner cover tube (4010) with a plurality of fasteners (4100). A drive system cover (4110) is attached to an outside perimeter of the first housing half (4060) with a plurality of fasteners (4120). The up and down relays are retained in the drive system cover (4110). An inlet hole (4130) is formed through a wall of the drive system cover (4110) to receive an inlet electrical connector (4140). The inlet electrical connector (4140) is attached to the drive system cover (4110) with at least two fasteners (4150). The inlet electrical connector (4140) is connected to the electronic controller or programmable logic circuit (315) with an electrical cable (not shown). The inlet electrical connector (4140) includes a ground line (4142), a power supply line (4144) and a retract power line 4146. A switch opening (4170) is formed through a wall of the drive system cover (4110) to receive an up-down switch (4160). The up-down switch (4160) is an on-off-on switch. The up-down switch (4160) includes an off-pole (4162), a first on-pole (4164) and a second on-pole (4166). The off-pole (4162) of the up-down switch (4160) is connected to the power supply line (4144) of the inlet electrical connector (4140). A switch lever (4168) of the up-down switch (4160) is toggled to the first on-pole (4164) to raise the inner cover tube (4010).

The electrical power flowing through the first on-pole (4164) energizes the up-relay (3980), which sends electrical power to the drive motor (3950) through a first contact (3982) and provides a path to ground for the drive motor (3950) through a second contact (3984). The electrical power flowing through the first on-pole (4164) is connected in series with a reset fuse (4172), which prevents the motor (3950) from being damaged, when the vent cover door (3930) is forced against the vent opening (4355). The motor (3950) is preferably a permanent magnet DC motor. Electromagnetic braking is inherent in permanent magnet DC motors. The electromagnetic braking keeps the vent cover door (3930) in contact with the vent opening (4355). The switch lever (4168) is toggled to the second on-pole (4166) to lower inner cover tube (4010). The electrical power flowing through the second on-pole (4166) energizes the down-relay (3990), which sends electrical power to the drive motor (3950) through a first contact (3992) and provides a path to ground for the drive motor (3950) through a second contact (3994). The retract power line (4146) is connected to the second on-pole (4166). Electrical power supplied through the retract power line (4146) will also lower the inner cover tube (4010).

The vent cover door (3930) includes a cover plate (4180), a peripheral sealing ring (4190) and a tube flange (4200). The peripheral sealing ring (4190) is attached to a top of the cover plate (4180) and around a perimeter thereof. The peripheral sealing ring (4190) is preferably fabricated of rubber, a rubber like material or any other suitable material. The tube flange (4200) is attached to a bottom of the cover plate (4180). The tube flange (4200) includes a tube opening (4210), which is sized to receive the inner cover tube (4010.) A tightening screw (4212) is used to secure the inner cover tube (4010) in the tube flange (4200). The rack gear (4020) is attached to the inner cover tube (4010) with a plurality of fasteners (4220). An end cap (4012) is preferably retained in a bottom of the inner cover tube (4010) with at least one fastener (4014). A rack slot (4230) is formed in the outer support tube (4000) to provide clearance for the rack gear (4020). The stop collar (4030) includes a clamp slot (4032), a tube opening (4034) and a stud slot (4036). A threaded stud (4240) is secured in the stud slot (4036) with a pair of nuts (not shown) secured to a top and bottom of the stop collar (4030). The threaded stud (4240) is positioned to actuate a normally closed limit switch (4250) to an open position to stop the flow of electricity to the down-relay (3990). The threaded stud (4240) is axially and radially adjusted to actuate a lever (4252) of the limit switch (4250) and stop the flow of electricity to the drive motor (3950), just before the down stop strikes a top of the drive housing (3970). A clamping fastener (4260) is tightened to secure the stop collar (4030) on the inner cover tube (4010).

Figure 1:
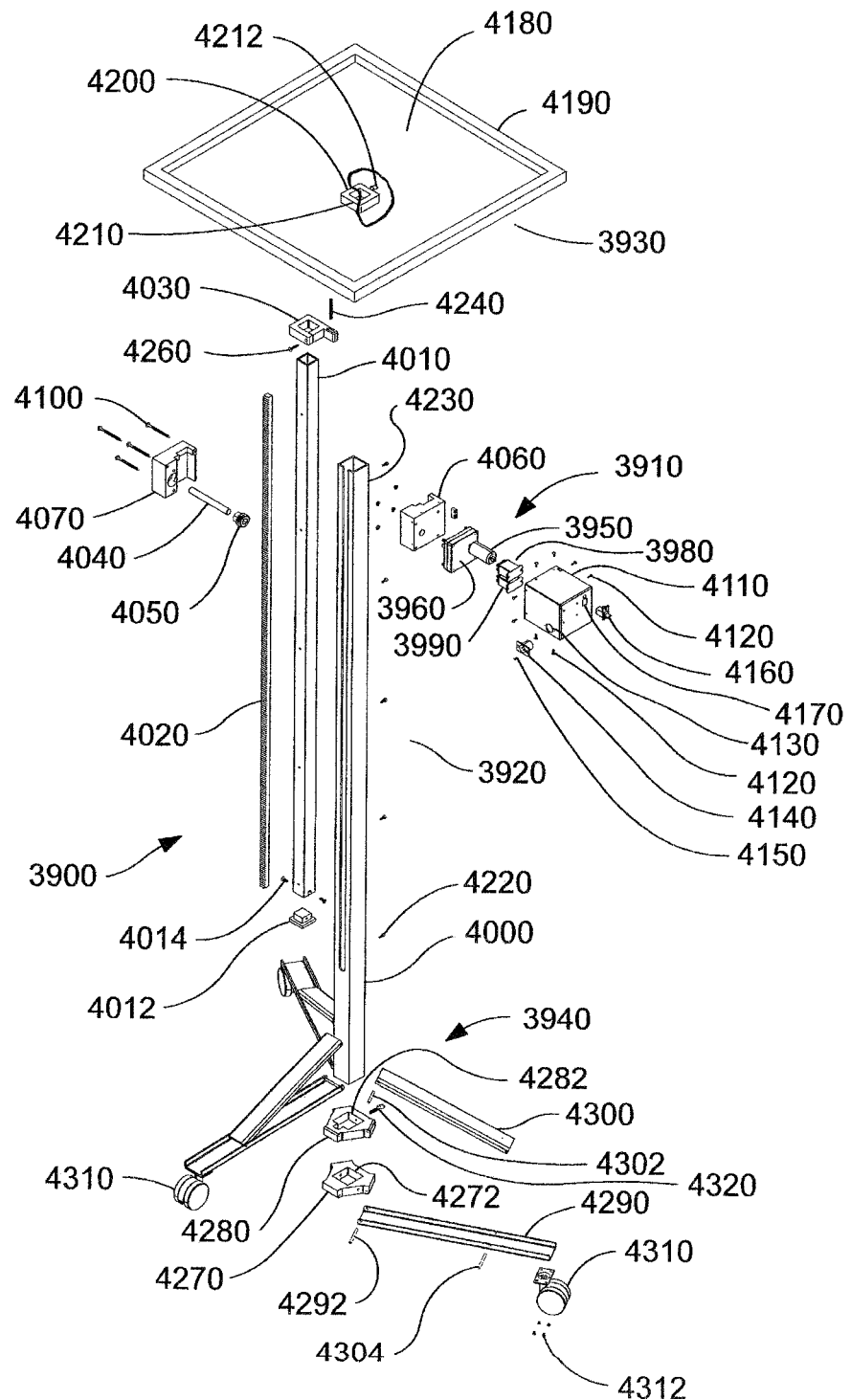
FIG. 1 is an exploded perspective view of a portable automated vent cover.
Figure 2:
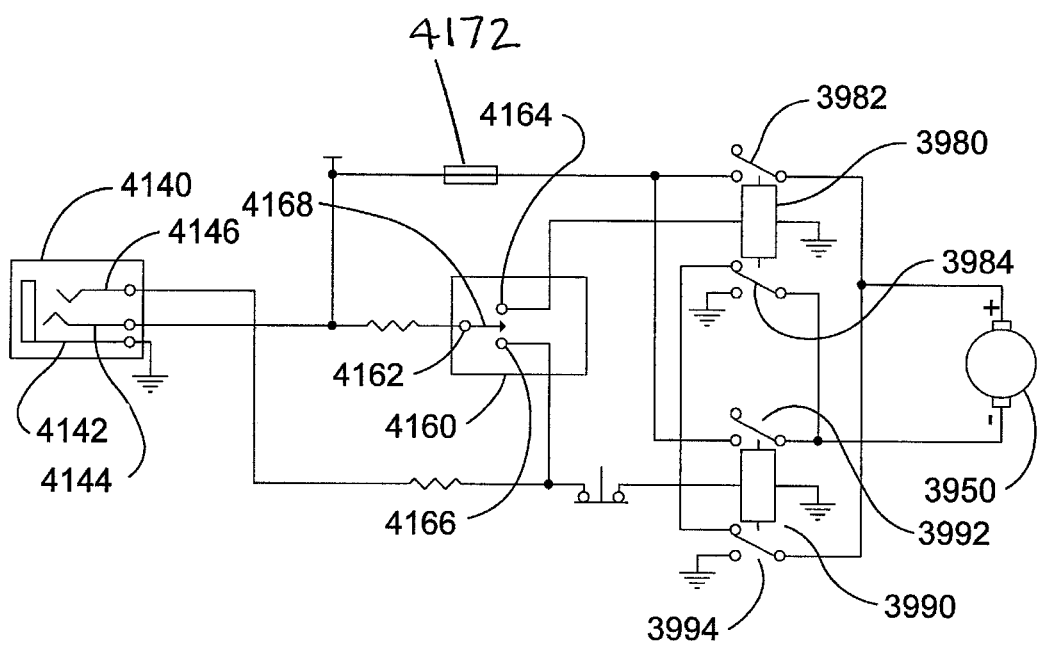
FIG. 2 is an electrical schematic of a portable automated vent cover.
Figure 3:
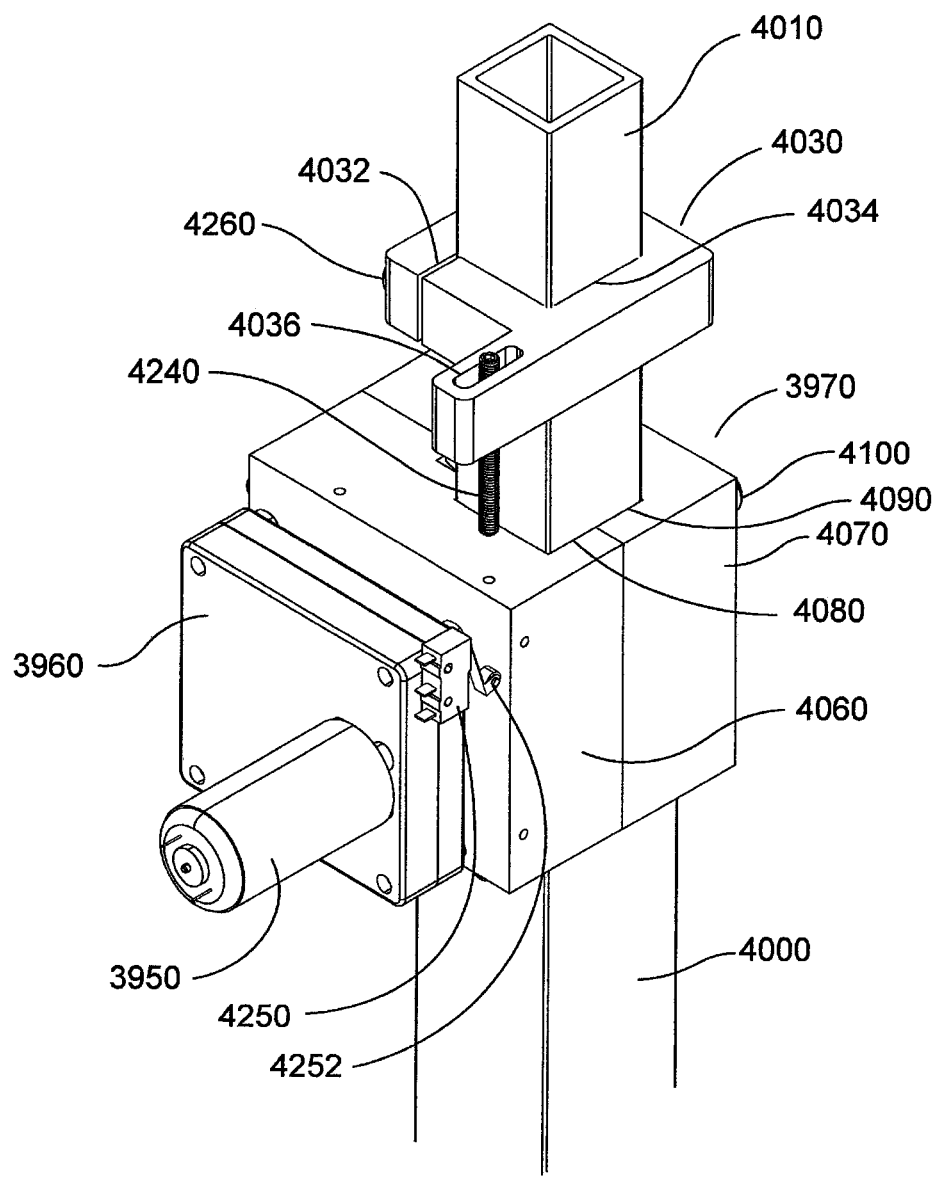
FIG. 3 is an enlarged perspective view of a drive system of a portable automated vent cover with a down stop in a raised position.
Figure 4:
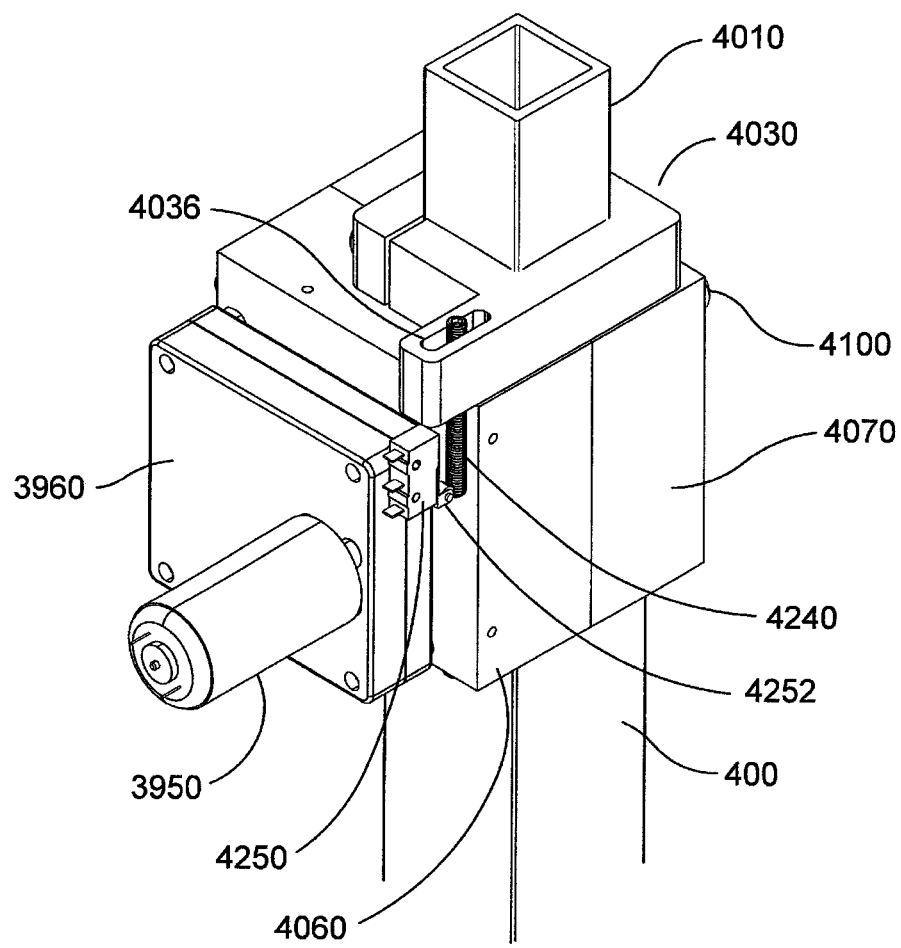
FIG. 4 is an enlarged perspective view of a drive system of a portable automated vent cover with a down stop in a lowered position.
Figure 5:
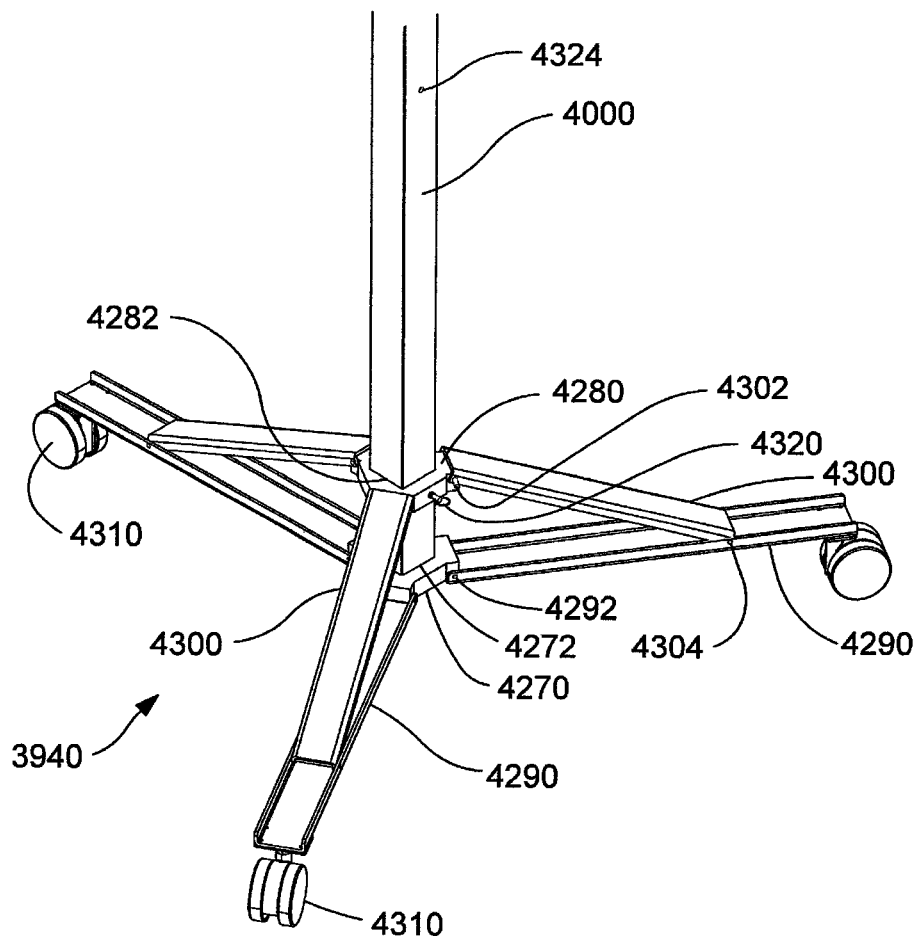
FIG. 5 is an enlarged perspective view of a mobile tripod of a portable automated vent cover.

With reference to FIGS. 5-6, the collapsible mobile tripod (3940) preferably includes a stationary pivot block (4270), a sliding pivot block (4280), three lower support arms (4290), three upper support arms (4300) and three castors (4310). The stationary pivot block (4270) includes a tube opening (4272), which is sized to receive the outer support tube (4000). The stationary pivot block (4270) is attached to a bottom of the outer support tube (4000) with any suitable device or method, such as fasteners. One end of the three lower support arms (4290) are pivotally attached equidistant around a perimeter of the stationary pivot block (4270) with three pivot pins (4292). The three castors (4310) are attached to a bottom of the other end of the three lower support arms (4290) with a plurality of fasteners (4312). The sliding pivot block (4280) includes a tube opening (4282), which is sized to slidably receive the outer support tube (4000).

One end of the three upper support arms (4300) are pivotally attached equidistant around a perimeter of the sliding block (4280) with three pivot pins (4302). The other end of the three upper support arms (4300) are pivotally attached to the three lower support arms with three pivot pins (4304). A locking pin (4320) is inserted through the sliding support block (4280) and a support hole (4322) or a retraction hole (4324) in the outer support tube (4000) to place the mobile tripod in a support orientation or a retracted orientation, respectively.

Figure 8:
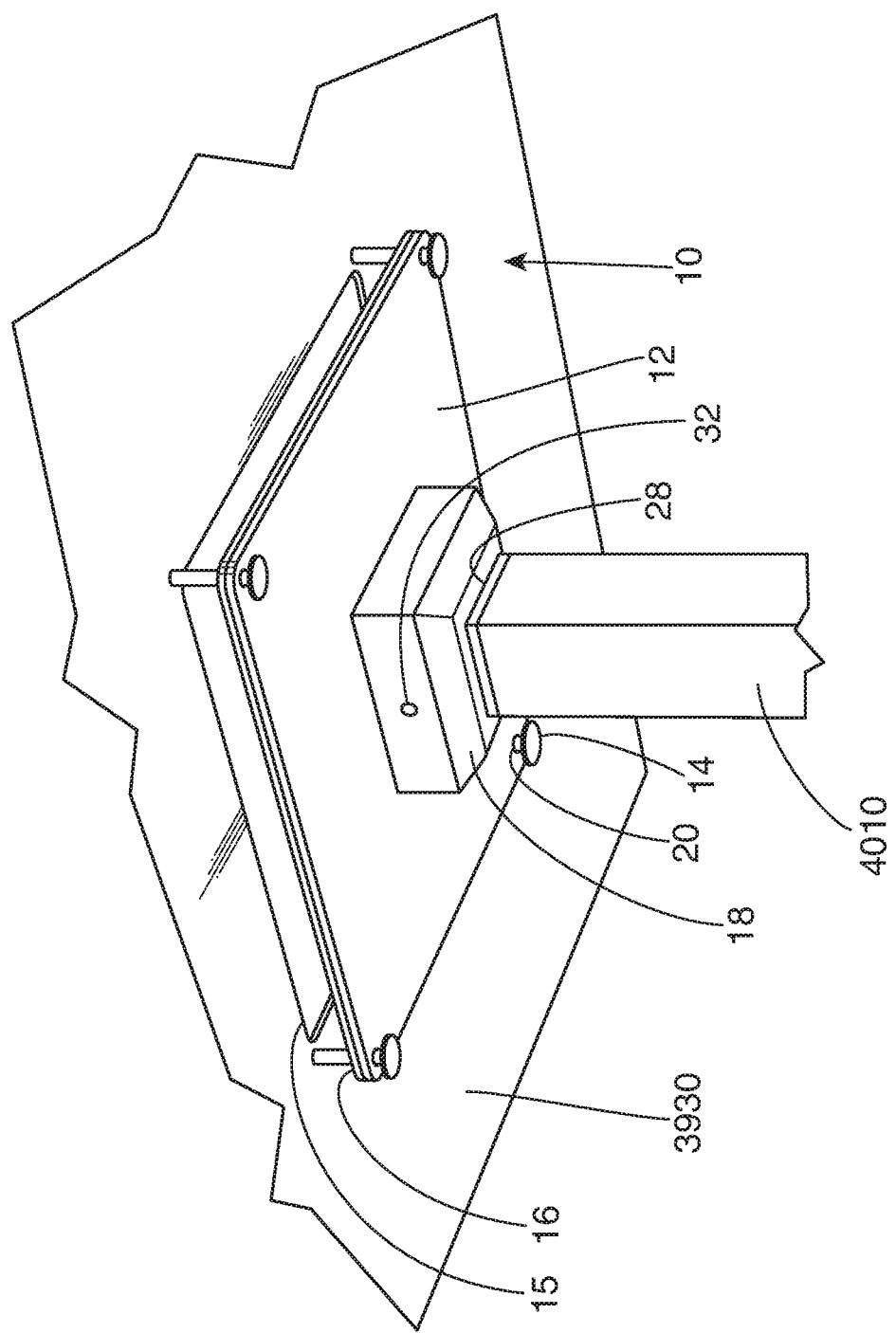
FIG. 8 is a bottom perspective view of a vacuum release door fully withdrawn from a vent cover door of a vent cover system in accordance with the present invention.
Figure 9:
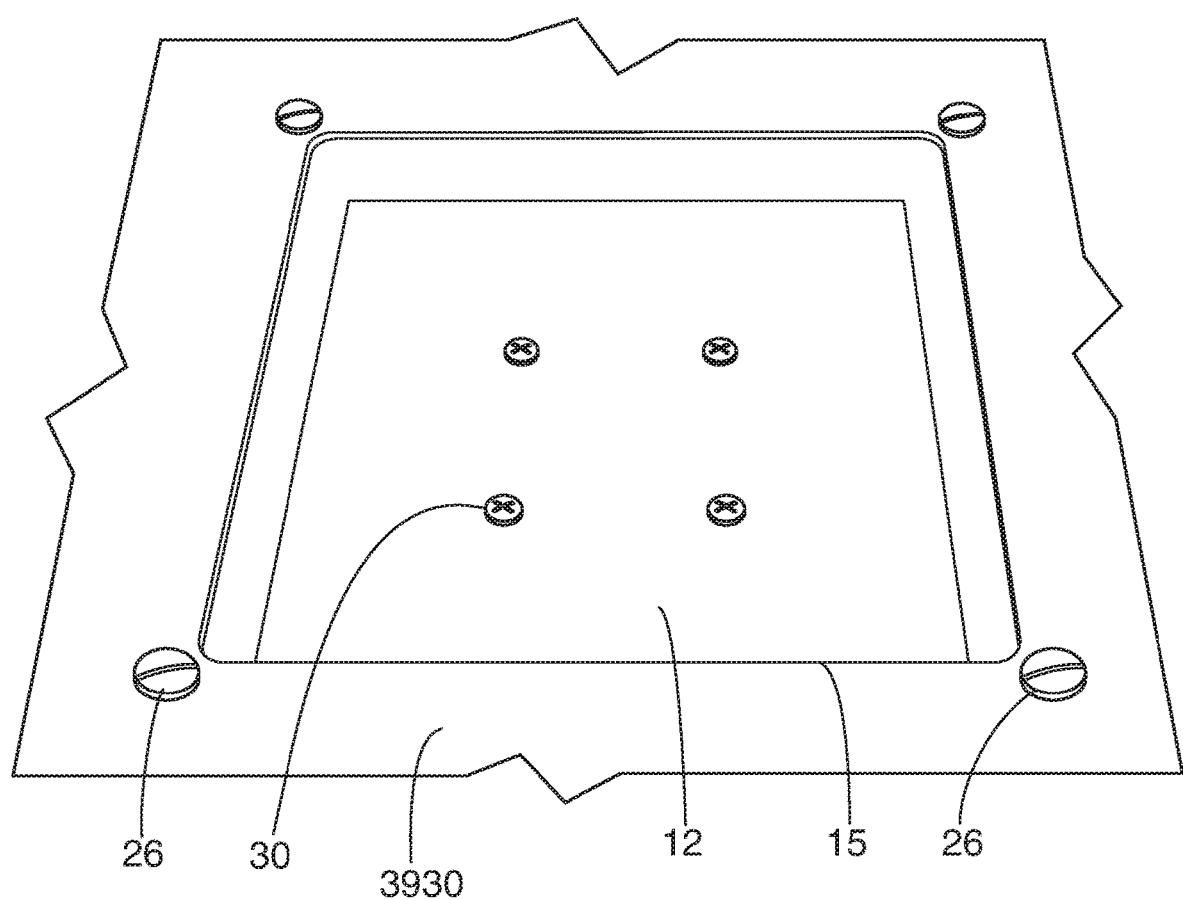
FIG. 9 is a top perspective view of a vacuum release door in contact with a vent cover door of a vent cover system in accordance with the present invention.

With reference to FIGS. 7-9, the vacuum release door (10) preferably includes a vacuum door plate (12), a plurality of retention pins (14), a sealing gasket (16) and a tube flange (18). The sealing gasket (16) preferably includes the same outer perimeter as the vacuum door plate (12). The sealing gasket (16) is preferably fabricated from rubber, a rubber like material, or any suitable material. A vacuum break opening (15) is formed through a center of the vent cover door (3930). The vacuum door plate (12) has an outer perimeter that is larger than a perimeter of the vacuum break opening (15). The sealing gasket (16) is attached to a top of the vacuum door plate (12). A plurality of pin holes (20) are formed around a perimeter of the vacuum door plate (12) to slidably receive the plurality of retention pins (14). Each retention pin (14) includes a head portion (22) and a pin portion (24). The pin portion (24) extends from the head portion (22). The pin portion (24) is inserted through the plurality of pin holes (20) and attached to the vent cover door (3930) with fasteners (26) or the like. Alternatively, and without limitation, the pin portion (24) is inserted through the plurality of pin holes (20) and attached to the vent cover door (3930) and/or the cover plate (4180), with fasteners (26) or the like. The pins (24) may also be suitably terminated on both ends, so they can perform their intended purposes, while also being able to have axial movement in the pin holes (20). However, other devices may also be substituted for the plurality of retention pins (14), such as but not limited to any type of guide rails. The tube flange (18) includes a tube opening (28), which is sized to snugly receive a top end of the inner cover tube (4010). The tube flange (18) is attached to a bottom of the vacuum door plate with fasteners (30) or the like. The inner cover tube (4010) is retained in the tube flange (18) with a pin (32) or the like.

In use, the vent cover door (3930) is raised, until a peripheral sealing ring (4190) on a top of the vent cover door (3930) seals around and/or to a perimeter of a vent opening (not shown). When an attempt is made to lower the vent cover door (3930) from the vent opening, retraction of the inner cover tube (4010) will cause a seal to be broken between the vacuum door plate (12) and the vacuum break opening (15) in the vent cover door (3930). After the seal is broken, the plurality of retention pins (14) will experience a downward force, which will cause a seal between the vent cover door 3930 and the vent opening to be broken. The vent cover system (1) makes it easier to break a seal between the vent opening and the vent cover door (3930), because the perimeter of the vacuum release door (12) is much shorter than a perimeter of the vent cover door (3930).

An air gap between a bottom of the vent cover door (3930) and a top of the vacuum door plate 12 is preferably, and without limitation, at least ⅛ inch, when the vacuum door plate (12) is in an open position. The vacuum door plate (12) seals the vacuum break opening (15) in a closed orientation. The vacuum door plate (12) does not cover the vacuum break opening (15) in an open orientation. It is easier to break a small perimeter seal than a large perimeter seal.

With reference to FIG. 10, a vent bypass system (34) includes at least one first vent cover (3930a) and at least one second vent cover (3930b). The first vent cover (3930a) includes a first vent plate (3931a) and a first sealing ring (3932a). The second vent cover (3930b) includes a second vent plate (3931b) and a second sealing ring (3932b). The vent bypass system (34) is created by forming a first bypass hole (36) through the first vent plate (3931a), and a second bypass hole (37) through a second vent plate (3930b) of two adjacent vent cover systems (1). A first tube flange (38) extends from a bottom surface of the first vent cover (3930a), and a second tube flange (39) extends from a bottom surface of the second vent cover (3930b), concentric with the bypass hole (36). The first vent cover (3930a) covers an entry vent (100) and the second vent cover (3930b) covers an exit vent (102). A first end of a flexible tube (tubular member) (40) is secured to the tube flange (38) of the first vent cover (3930a) with a securement device, such as a hose clamp (42) or the like, and a second end of the flexible tube (40) is secured to the second tube flange (38) of the second vent cover (3930b). The flexible tube or tubular member may have any suitable cross-sectional shape.

The tubular member (40) member will keep the HVAC system (103) substantially balanced by not sealing up a normal flow pattern through the enclosed space (104). Any type of support device may be used to force the first vent cover door (3930a) against the entry vent (100) and the second vent cover door (3930b) against the exit vent (102), such as a painter's pole (4365), a collapsible mobile tripod (3940), or any other suitable manual or automated support device.

Gas blown into the enclosed space (104) will bypass circulating through the enclosed space (104) by going through the flexible tube 40 from the entry vent (100) to the exit vent (102). The vent bypass system (34) will also keep a balance in a circulating system by not sealing up a normal flow pattern through the room. Additionally, more than one entry vent (100) may be transferred to one exit vent 102 with more than one tube (40), or one entry vent (100) may be transferred to more than one exit vent (102) with more than one tube (40).

With reference to FIGS. 11-15, an alternative embodiment of the vent bypass system (4415) can be positioned to and/or sealed against gas vents (4400) and (4405) in various ways including, but not limited to, automatically using any automated vent cover apparatus (3900), and/or manually using any manually adjustable vent cover holding and sealing apparatus (4430).

Without being limited, the vent bypass system (4415), can also include various components, such as, but not limited to any, vacuum release door(s) (10), vacuum break opening(s) (15), vent cover door(s) (3930), hose(s) (4380), and hose connection(s) (4420). The hose(s) (4380) can effectively connect and operate with any apparatus or component that can effectively seal any air/gas entry vent(s) (4400) and any air/gas exit vent(s) (4405). It is preferred, without limitation that the hose(s) (4380) connect to the various vent cover door(s) (3930) with one or more of any hose connection(s) (4420). Without being limited, the hose(s) (4380) can allow any air/gas to flow out from one or more vent(s) (4400) that opens into a room(a) or connected space(s), through the hose(s) (4380), and into and out of another one or more vent(s) (4405) that is in the same room or connected space, allowing the air/gas(s) to leave that room(s) or connected space(s). It is preferred, without limitation, that these one or more room(s) or connected space(s) (4410) are effectively connected and sealed.

More specifically, and without being limited, the hose connection(s) (4420) can include, one or more of any inbound air/gas hose connection(s) (4385) and outbound air/gas hose connection(s) (4390), all known to those skilled in the art, and they can be directly and/or indirectly connected, in various ways including, permanently, semi-permanently, and/or removable, to any vent covering component(s) such as, but not limited to any, vent cover door(s) (3930), or any other connected location(s) and/or component(s), all in a manner known in the art.

Referring again to FIGS. 14-15, and without being limited, any vent(s) connecting to any rooms and/or connected space(s), or any part of any vent(s) such as, but not limited to any, air/gas entry vent(s) (4400), air/gas exit vent(s) (4405), and/or any vent opening(s) (4355), can also be designed to be effectively sealed against the escape of any air/gas(s), while still being effectively sealed to and effectively interfaced with, any hose connection(s) (4420) for the passage of any air/gas(s) to any hose(s) (4380).

Again, with reference to FIGS. 11-15, the hose connection(s) (4420) can allow any gas to pass through one or more of any connected parts, such as, but not limited to any, inbound gas vent(s) (4385), outbound air/gas vent(s)(4390), vent(s) opening(s) (4355), vent cover door(s) (3930), hose(s) (4380), and hose connection(s) (4420), and function effectively as a system for the effective movement, passage, and/or transfer, of any air or gas(s) to, from, and/or through, any vent(s) (4385) (4390) and hose(s) (4380), in any room(s) and/or connected space(s) (4410).

Figure 12:
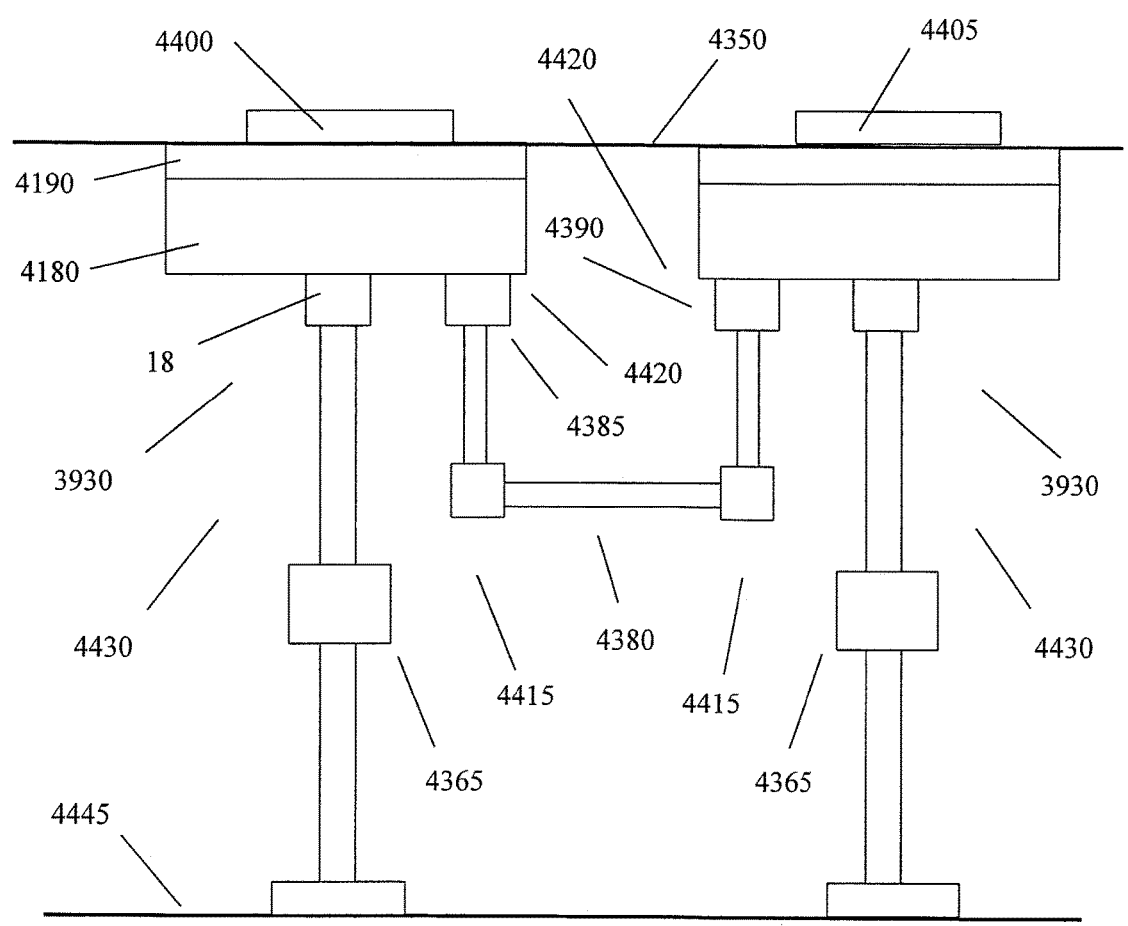
FIG. 12 is a side view of targeted space having an gas entry vent and a gas exit vent, both sealed with a separate vent cover door and a vacuum release door, all in a sealed state, and positioned against a ceiling surface with a manual vent holding apparatus, where both vents are connected via a hose connecting both vent cover doors and their respective vents of a vent bypass system in accordance with the present invention.
Figure 13:
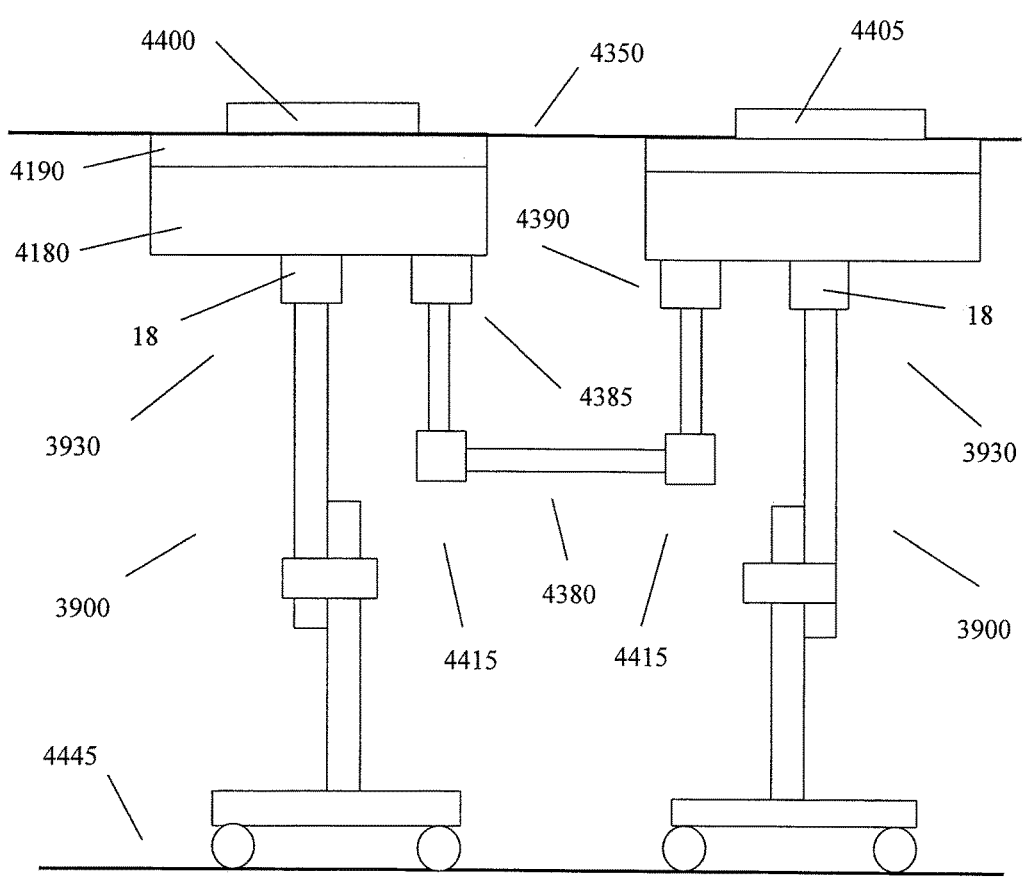
FIG. 13 is a side view of targeted space having an air/gas entry vent and an gas exit vent, both sealed with a separate vent cover door and a vacuum release door, all in a sealed state, and positioned against a ceiling surface with a portable automated vent cover apparatus, where both vents are connected via a hose connecting both vent cover doors and their respective vents of a vent bypass system in accordance with the present invention.
Figure 14:
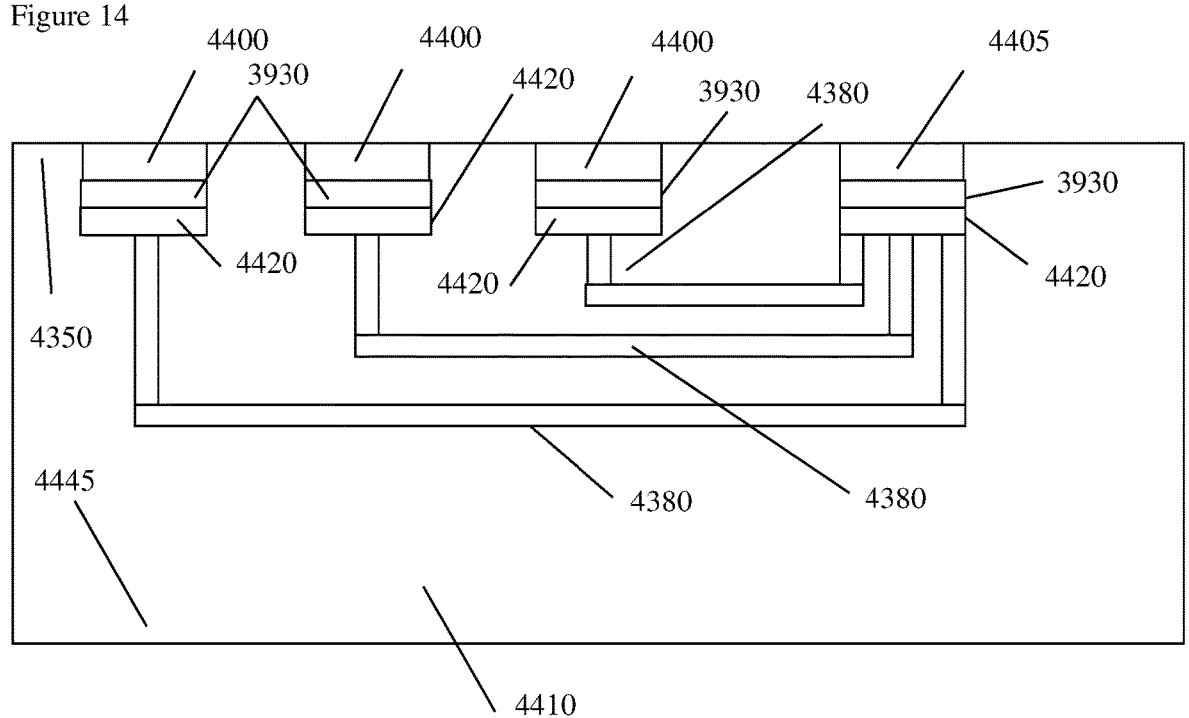
FIG. 14 a side view showing air/gas flowing into a room or connected space from two separate entry vents, and then exiting the room from one exit vent of a vent bypass system in accordance with the present invention.
Figure 15:
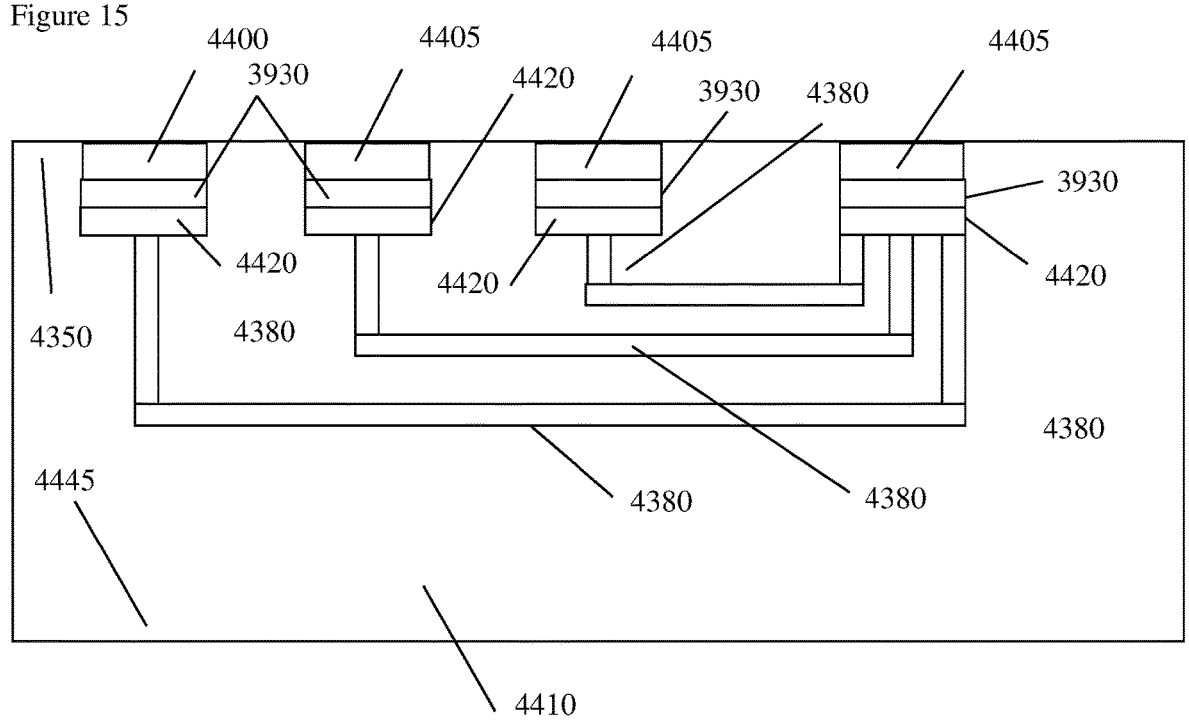
FIG. 15 a side view showing air/gas flowing into a room or connected space from one entry vent, and then exiting the room from three separate exit vents of a vent bypass system in accordance with the present invention.

According to FIGS. 12-13, it is preferred that two separate vent cover and hose bypass systems (4415) are each interfaced with a manually adjustable vent cover holding and sealing apparatus (4430) as shown in FIG. 12, and an automated vent cover apparatus (3900) as shown in FIG. 13, where both apparatus do not include any vacuum release door (10) and vacuum break opening (15).

Referring to FIGS. 12-13 and without limitation, the vent cover door (3930) belonging to a first vent cover and hose bypass system (4415), effectively seals an air/gas entry vent (4400), while another separate vent cover door (3930) belonging to another second vent cover and hose bypass system (4415), effectively seals an air/gas exit vent (4405). Any type of support device may be used to force the cover plate (4180) against the gas entry vent (4400) or the gas exit vent (4405), such as the painter's pole (4365), a collapsible mobile tripod (3940), or any other suitable manual or automated support device.

At least one hose (4380) connects the first vent cover and hose bypass system (4415) to the second vent cover and hose bypass system (4415). The hose(s) (4380) effectively connect to each vent cover door (3930) via at least one hose connection(s) (4420). More specifically, the inbound air/gas hose connection (4385) effectively connects the hose (4380) to the vent cover door (3930) that effectively covers and/or seals the air/gas entry vent (4400), while the same hose (4380) effectively connects with the outbound air/gas hose connection (4390) that connects with the vent cover door (3930) that effectively covers and/or seals the air/gas exit vent (4405). The flow of air/gas bypasses flowing into the enclosed space and flows back into the ventilation system.

With reference to FIGS. 10-24, and without limitation, an apparatus and method of another embodiment of the present invention, can also relate generally to the cleaning, sanitization, disinfection, sterilization, and/or decontamination, of the interior and/or exterior, and/or any other part, of one or more of any, air duct(s), air duct system(s), air supply duct(s), air supply trunk line(s), air return trunk line(s), air outlets, air inlets, air return duct(s), air shaft(s), hose(s) (40)(4380), means to channel, stop, restrict, and/or direct air/gas(s), and/or any other conduit(s) to move any air and/or gas(s) through, to, and/or from, one or more of any, HVAC equipment, room(s) (4410), area(s), and/or building(s), (Herein called "Air Duct(s)") (4455) that are used to supply any air and/or gas(s) that is heated, cooled, humidified, dehumidified, blown, pumped, and/or filtered, to various room(s) (4410), space(s), building(s), and/or building area(s), and are also used to return any air from these various room(s) (4410), space(s), building(s), and/or building area(s) back to the various HVAC part(s) and equipment(s) (4465), as well as any suitable and effective means known to those skilled in the art used for, heating air, moving air, delivering air, ventilating air, filtering air, processing air, humidifying air, dehumidifying air, adding fresh air, and/or cooling air, as well as any other associated system(s), equipment(s), part(s) and component(s) known to those skilled in the art such as, but not limited to any, air/gas(s) valve(s) (not shown), air/gas(s) diversion apparatus(s) (not shown), air duct(s) (4455), air duct(s) system(s) (4460), air/gas entry vent(s) (4400), air/gas exit vent(s) (4405), and/or vent opening(s) (4355) (Herein all generally called "HVAC part(s) and equipment(s)") (4465). Without being limited, air duct system(s) (4460) can include but are not limited to, one or more of any effectively connected air duct(s) (4455). Without being limited, the said room(s) (4410) can have one or more of any suitable floor(s) (4445). Also, and without being limited, the one or more of any, HVAC system(s), air duct(s) (4455), and/or air duct(s) system(s), within any building(s) (4470), can connect with one or more of any suitable and effective apparatus(s) that can be used for one or more of any uses and activities such as, but not limited to any, heating air, moving air, delivering air, ventilating air, filtering air, processing air, humidifying air, dehumidifying air, adding fresh air, and/or cooling air (Herein collectively called "HVAC Unit(s)" (4610)). Without being limited, many building(s) (4470) known to those skilled in the art use at least one HVAC unit(s) (4610) to heat air, move air, deliver air, ventilate air, filter air, process air, humidify air, dehumidify air, add fresh air, and/or cool air, that is flowed and/or circulated through one or more of any area(s) and room(s) (4410) of any building(s) (4470). Without being limited, the HVAC part(s) and equipment(s) (4465) can also include one or more of any suitable HVAC unit(s) (4610).

Without being limited, the present invention can also relate generally to the cleaning, sanitization, disinfection, sterilization, and/or decontamination, of the interior and/or exterior, and/or any other part, of one or more of any part(s) and component(s) associated with any, filtering of air/gas(s), heating of air/gas(s), cooling of air/gas(s), humidification of air/gas(s), dehumidification of air/gas(s), movement of air/gas(s), adding fresh air, ventilation of any air, including any part(s) and/or apparatus(s) of any HVAC unit(s) (4610), and/or any other HVAC part(s) and equipment(s) (4465), as well as any other associated parts and components used to heat, humidify, dehumidify, ventilate, filter, move, and/or cool, any air and/or gas(s) that is flowed within, into, through, and/or out of, various residential, commercial, industrial, and/or healthcare building(s) and/or structure(s) (Herein called "Building(s)" (4470), as well as any means to carry, transmit, and/or pipe, any air/gas(s) flow(s) within any building(s) (4470), such as, but not limited to any, air duct(s) (4455), air duct system(s) (4460), air/gas entry vent(s) (4400), air/gas exit vent(s) (4405), air supply duct(s) (4515), air return duct(s) (4520), vent opening(s) (4355), air handler(s) (not shown), register(s) (not shown), grilles (not shown), blower(s) and fan(s) (not shown), duct fan(s) (4535), and any other associated part(s), motor(s), housing(s), piping(s), air plenum(s) (not shown), drain pan(s) (not shown), air cleaner(s) (not shown), heat exchanger(s) (not shown), coil(s) (not shown), and/or chill coil(s) (not shown), of any HVAC part(s) and equipment(s) (4465) and/or HVAC unit(s) (4610) known to those skilled in the art (Herein collectively called "HVAC Part(s) and Equipment" (4465)). Without being limited, air duct(s) (4455) can include one or more of any, pipe(s), tube(s), and/or conduit(s), preferably and without limitation, that are effective, through which any air/gas(s) can flow through various building(s) (4470) and to and from any HVAC unit(s) (4610) as well as any area(s) and room(s) (4410) located in various building(s) (4470), and also includes any air duct(s) such as, but not limited to any, air duct system(s) (4460), air shaft(s) (4472), air supply duct(s) (4515), and air return duct(s) (4520).

Without being limited, the present invention also relates generally to the use of one or more of any suitable and effective means, known to those skilled in the art, to generate, administer, distribute, flow, deliver, disperse, and/or transmit (Herein called "Agent Dispenser(s)") (4505) one or more of any, substance(s), agent(s), chemical(s), chemistry(s), and/or molecule(s), in any suitable and effective quantity, and in one or more of any suitable and effective form(s), such as, but not limited to any, gas(s), vapor(s), aerosol(s), dry aerosol(s), and/or liquid aerosol(s) (Herein called "Deployed Agent(s)") (4510), to one or more of any area(s), surface(s), and/or space(s), such as, but not limited to, the interior of, inside of, within, and/or on, any targeted surface(s) of any, air duct(s) (4455), room(s) (4410), enclosure(s), compartment(s), air shaft(s), means to channel and/or direct air (not shown), vent(s) (4400)(4405), orifice(s), hose(s) (40)(4380), vent bypass system (4415), conduits to move any air flow(s), air duct system(s) (4460), HVAC unit(s) (4610), as well as any HVAC part(s) and equipment(s) (4465) and HVAC system related part(s) and component(s), for one or more of any purpose(s) such as, but not limited to, killing, destroying, neutralizing, and/or decontaminating, one or more of any pathogen(s) and/or microorganism(s) such as, but not limited to any, virus(s), bacteria(s), mold(s), fungus(s), and/or spore(s), that may be present on any of these surface(s), targeted surface(s), and/or suspended in any air and/or gas(s). The agent dispenser(s) (4505) and the current invention can also be used for other foreseeable purposes such as, but not limited to, deploying any suitable and effective aerosol(s) for various purposes such as, but not limited to, plugging holes in any air duct(s) (4455), air duct(s) system(s) (4460), and/or HVAC part(s) and equipment(s) (4465) and HVAC system(s), all in a manner known to those skilled in the art, as well as encapsulating any particles within, inside of, and/or on any, air duct(s) (4455), air duct(s) system(s) (4460), and/or HVAC part(s) and equipment(s) (4465), in a manner known to those skilled to the art. Without being limited, the deployed agent(s) (4510) can be administered and/or deployed into the various, air duct(s) (4455), air duct(s) system(s) (4460), any suitable and effective part of any vent bypass system(s)

(4415), and/or HVAC part(s) and equipment(s) (4465), at any suitable and effective, concentration(s), quantity(s), air flow velocity(s), air speed(s), flow rate(s), density(s), particle size(s), ingredient number(s), temperature(s), mass concentration(s), time interval(s), concentration(s), and/or for any treatment and exposure time(s). Without being limited, the one or more agent dispenser(s) (4505) can also include internally and/or externally in its design, one or more of any means to move, disperse, inject, and/or deploy, the one or more deployed agent(s) (4510), such as, but not limited to one or more of any suitable and effective blower(s), fan(s), and/or air pump(s).

Without being limited, the one or more agent dispenser(s) (4505) can include, but is not limited to any, vaporized hydrogen peroxide (VHP) gas deployment system, aerosol containing hydrogen peroxide deployment system, ozone gas deployment system, aerosol containing ozone deployment system, chlorine dioxide gas deployment system, aerosol containing chlorine dioxide deployment system, peroxyacetic acid (PAA) gas deployment system, aerosol containing peroxyacetic acid (PAA) deployment system, ultrasonically derived aerosol(s), and/or any other effective airborne systems, technologies, and methods, to administer, distribute, flow, blow, deliver, disperse, and/or transmit, one or more of any, substance(s), agent(s), chemical(s), chemistry(s), molecule(s), or otherwise any suitable and effective deployed agent(s) (4510), known to those skilled in the art for purposes including, but not limited to, treating, disinfecting, sterilizing, sanitizing, decontaminating, plugging, and/or encapsulating, various surfaces, part(s) (4465), and/or area(s).

It is known to those skilled in the art that any, air duct(s) (4455), air duct system(s) (4460), air shafts (4472), air conduit(s), air filters, means to hold or mount any air filter(s), and/or any other HVAC part(s) and equipment(s) (4465) known in the art, can harbor and/or be contaminated with any, virus(s), mold(s), fungus(s), bacteria(s), spore(s), contaminate(s), and/or pathogen(s). Without being limited, this can especially be a problem with buildings (4470) that have "sick building syndrome" due to the presence of pathogens such as, but not limited to any, mold and fungus growth within, inside of, and/or on, any, air duct(s) (4455), air duct(s) system(s) (4460), and/or HVAC part(s) and equipment(s) (4465), that are used to move air into, within, out of, and/or throughout, one or more of any building(s) (4470) and/or one or more of any room(s) (4410) within any building(s) (4470). Without being limited, various industries such as, but not limited to, the pharmaceutical, biotechnology, medical device, and biomedical industry, are also concerned with pathogen safety and the microbiological cleanliness within, inside of, and/or on, any, air duct(s) (4455), air duct(s) system(s) (4460), and/or HVAC part(s) and equipment(s) (4465) that are used to move air into, within, out of, and/or throughout, one or more of any room(s), isolated clean space(s), clean room(s), system of clean room(s), system of clean space(s) (Herein also called "Room(s)") (4410) and/or building(s) (4470). Without being limited, the healthcare industry is also increasingly concerned with pathogen safety and the microbiological cleanliness within, inside of, and/or on, any, air duct(s) (4455), air duct(s) system(s) (4460), and/or HVAC part(s) and equipment(s) (4465) that are used to move air into, within, out of, and/or throughout, one or more of any room(s) (4410) and/or building(s) (4470), especially as the world has now entered the end of the antibiotic era, and especially with the new threat that is reported with the fungus *C. auris*.

It is also known to those skilled in the art that the cleaning and/or treating of any, air duct(s) (4455), air duct(s) system(s) (4460), and/or HVAC part(s) and equipment(s) (4465) can be a labor and time intensive process. For example, and without being limited, one or more of any suitable and effective steps known to those skilled in the art, can be taken to effectively clean, sanitize, disinfect, sterilize, and/or decontaminate, the one or more of any area(s), surface(s), and/or space(s), on and/or within any, air duct(s) (4455), hose(s) (40)(4380), vent bypass system(s) (4415), air duct(s) system(s) (4460), and/or HVAC part(s) and equipment(s) (4465), such as but not limited to: (a) mechanically scrubbing, mechanically hitting, air whipping, air washing, air brushing, hitting surface(s) with compressed air from one or more air nozzle(s) outlets, agitating, brushing, and/or wiping, the various targeted surface(s) of these various parts, space(s), and/or area(s), for purpose(s) such as, but not limited to, loosening and/or removing any, foreign object debris, contaminant(s), pathogen(s), organism(s), dirt, dust, debris, and/or residue(s), that may have accumulated within, inside of, and/or on, the various air duct(s) (4455), air duct(s) system(s) (4460), and/or HVAC part(s) and equipment(s) (4465) (Herein called "Loosening the Contamination(s)"), (b) vacuuming the various air duct(s) (4455), air supply duct(s) (4515), hose(s) (40)(4380), vent bypass system(s) (4415), air return ducts (4520), and various HVAC part(s) and equipment(s) (4465), with one or more of any effective tool(s) and/or apparatus(s) known to those skilled in the art that can be used for vacuuming these various part(s), component(s), space(s), and/or conduit(s), by pulling any effective vacuum on any and/or all part(s) of any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), various HVAC part(s) and equipment(s) (4465), sealed zone(s) (4532), and/or one or more of any sealed air/gas flow system(s) (4530), and/or by blowing or moving any effective airflow and quantity of air through these various part(s), component(s), space(s), and/or conduit(s), at one or more of any effective time(s) and for any suitable and effective duration of time(s), to remove any foreign object debris and/or residue(s) that may have accumulated within, inside of, and/or on, any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), and various HVAC part(s) and equipment(s) (4465), sealed zone(s) (4532), and/or one or more of any sealed air/gas flow system(s) (4530) (Herein called "Collecting the Contaminant(s)"), and/or (c) administering, distributing, flowing, delivering, dispersing, and/or transmitting, one or more of any, deployed agent(s) (4510), substance(s), agent(s), chemical(s), chemistry(s), and/or molecule(s), such as, but not limited to any, disinfectant(s), sterilant(s), sporicide(s), sanitizer(s), anti-fungal compound(s), anti-mold compound(s), in one or more of any suitable and effective form(s), such as, but not limited to any, gas(s), vapor(s), aerosol(s), dry aerosol(s), and/or liquid aerosol(s), by one or more of any suitable and effective agent dispenser(s) (4505), to clean, sanitize, disinfect, sterilize, and/or decontaminate, the one or more of any area(s), surface(s), and/or space(s), on and/or within any, conduit(s), part(s), space(s), area(s), hardware(s), such as, but not limited to any, air duct(s) (4455), hose(s) (40)(4380), vent bypass system(s) (4415), air duct(s) system(s) (4460), and/or HVAC part(s) and equipment(s) (4465) (Herein called "Treating the Surfaces"). Without being limited, the "loosening of the contamination" step can also be combined with the "collecting the contaminants" step at the same time. Also, without being limited, the various steps and activities of "loosening of the contamination", "collecting the contaminant(s)", and "treating the surfaces", can all be combined at the same time. It is preferred, without limitation, that the "treating the surface(s)" step is performed after the steps of "loosening of the contamination(s)" and "collecting the contaminant(s)".

The current art has, without being limited, multiple problems known to those skilled in the art, that can be solved with the current invention. First, and without being limited, it can be difficult to pull and/or establish an effective vacuum or establish an effective positive airflow pressure, on and/or through the one or more air duct(s) (4455), system of air duct(s) (4460), and/or HVAC system(s) known to those skilled in the art, any sealed off and/or isolated targeted zone(s) (4532) (4540) of air duct(s) (4455), and/or air duct system(s) (4460), to clean in various ways known to those skilled in the art and/or chemically treat with various methods previously mentioned including, but not limited to any, effective airborne surface treatment method(s), for one or more of any space(s), location(s), part(s) and component(s) such as, but not limited to any, building(s) (4470), air duct(s) (4455), air duct system(s) (4460), isolated air duct(s) (4540), sealed zone(s) (4532), isolated air duct system(s), unisolated targeted zone(s) of HVAC part(s) and equipment(s) (4465) and air duct(s), isolated targeted zone(s) of HVAC part(s) and equipment(s) (4465) and/or air duct(s) (4550), and/or HVAC system(s) known to those skilled in the art, because of one or more of various limiting factors known to those skilled in the art can be such as, but not limited to: (a) the total length of all of the combined air duct(s) (4455) and/or air duct(s) system(s) (4460), in the building(s) (4470), targeted area(s) of the building(s) (4470), and/or HVAC system(s) known to those skilled in the art, can be excessively long to achieve an effective outcome, and (b) one or more of any air/gas(s) supply duct(s) (4515) and/or return duct(s) (4520) can both connect with, communicate with, and/or enter into any, same or common room(s), area(s), and/or connected space(s) (4410), contributing to a loss of the needed air/gas(s) pressures or vacuum that is needed to be established for any effective outcome(s), cleaning(s), and/or surface treatment(s). Second, and without limitation, one or more of any air duct(s) (4455) and more specifically, and without limitation any, air/gas(s) supply duct(s) (4515) and/or air/gas(s) return ducts (4520), that are directly and/or indirectly connected with one or more of any agent dispenser(s) (4505), can both connect with, communicate with, and/or enter into any, same or common room(s), area(s), and/or connected space(s) (4410), resulting in deployed agent(s) (4510), that are emitted and/or deployed by the agent dispenser(s) (4505), entering these said room(s), area(s), and/or connected space(s) (4410), when this result and/or situation is not desired and/or needs to be avoided for reasons known to those skilled in the art.

Without being limited, personnel such as, but not limited to any, HVAC cleaning personnel, technicians, their co-workers, and/or any other associated people, who loosen the contamination(s), collect the contaminant(s), and/or treat surfaces, of any, air duct(s) (4455), air duct(s) system(s) (4460), and/or HVAC part(s) and equipment(s) (4465), in situation(s) known to those skilled in the art, may need to effectively seal, cover, and/or block off, one or more of any, air duct(s) (4455), HVAC part(s) and equipment(s) (4465), and/or one or more of any section(s) and/or zone(s) (4532) (4525)(4530)(4545)(4550) including any HVAC part(s) and equipment(s) (4465), such as, but not limited to any, air duct(s) (4455), air duct(s) system(s) (4460), air/gas entry vent(s) (4400), air/gas exit vent(s) (4405), vent opening(s) (4355), and/or any other HVAC part(s) and equipment(s) (4465) known to those skilled in the art, in one or more area(s), location(s), and/or place(s), for purposes including, but not limited to, effectively loosening the contamination(s), collecting the contaminant(s), and/or treating the surfaces, of any, air duct(s) (4455), air duct(s) system(s) (4460), and/or HVAC part(s) and equipment(s) (4465). In addition, and without limitation, one or more hole cut(s) are sometimes also made into these various HVAC part(s) and equipment(s) (4465) such as, but not limited to any, air duct(s) (4455), air duct(s) system(s) (4460), air shaft(s) (4472), and/or any other HVAC part(s) and equipment(s) (4465), in order to effectively loosen the contamination(s), collect the contaminant(s), and/or treat the surfaces, of any various, air duct(s) (4455), air duct(s) system(s) (4460), and/or HVAC part(s) and equipment(s) (4465), including for one or more of any isolated section(s) and/or zone(s) (4540) of one or more of any, air duct(s) (4455), air duct(s) system(s) (4460), and/or any other HVAC part(s) and equipment(s) (4465), that are cleaned and/or treated.

Without being limited, a major problem in the current art is that the various air duct(s) (4455), air duct(s) system(s) (4460), and/or HVAC part(s) and equipment(s) (4465), such as, but not limited to any, supply duct(s) (4515), and return ducts (4520), and/or any other HVAC part(s) and equipment(s) (4465), especially and without limitation the one or more of any supply duct(s) (4515) and/or return duct(s) (4520), that both connect with, communicate with, and/or enter into, the same or common room(s), area(s), and/or connected space(s) (4410), could not be connected in any effective, communicating line, circuit, open circuit, closed circuit, sealed circuit, sealed and communicating line, including but not limited for any, entire HVAC system for a building, entire system of directly and/or indirectly communicating air duct(s) in a building(s) (4470), isolated section(s) and/or zone(s) (4540) and/or unisolated section(s) and/or zone(s) (4545) of one or more of any HVAC part(s) and equipment(s) (4465) such as, but not limited to any, air duct(s) (4455), air duct(s) system(s) (4460), air/gas(s) supply duct(s) (4515), and/or air/gas(s) return ducts (4520).

More specifically, and without limitation, the various air duct(s) (4455), and more specifically the various air duct(s) (4455), supply duct(s) (4515), and/or return ducts (4520) for an HVAC system in any building, flow air into and/or out of various room(s), zone(s), area(s), and/or zone(s) of room(s) and/or area(s) (Herein called "Room(s)" (4410)). These various air duct(s) (4455), and more specifically the various air/gas(s) supply duct(s) (4515) and/or air/gas(s) return ducts (4520) connect via these various room(s), zone(s), area(s), and/or zone(s) of room(s) and/or area(s) (4410), in a manner known in the art, where one or more supply duct(s) (4515) can connect or communicate with these one or more various room(s), zone(s), area(s), and/or zone(s) of room(s) and/or area(s) (4410) to supply air into these location(s) that is, without limitation, treated, heated, filtered, dehumidified, humidified, and/or cooled, by the various HVAC unit(s) (4610) and HVAC part(s) and equipment(s) (4465), and one or more return ducts (4520) can also connect or communicate with these one or more various room(s), zone(s), area(s), and/or zone(s) of room(s) and/or area(s) (4410) to return the air from these various room(s), zone(s), area(s), and/or zone(s) of room(s) and/or area(s) (4410), back to the various HVAC unit(s) (4610) and HVAC part(s) and equipment(s) (4465) so the returned air can be treated, heated, filtered, dehumidified, humidified, and/or cooled. The air/ gas(s) supply duct(s) (4515) and the air/gas(s) return ducts (4520) for these various room(s), zone(s), area(s), and/or zone(s) of room(s) and/or area(s) (4410) are not directly connected since they are used to flow air into and out of these various area(s) and room(s) (4410).

Without being limited, this can present problems such as, but not limited to, the debris from cleaning the various air duct(s) (4455) can be deposited into the room(s) (4410) where the various air duct(s) (4455) connect, the needed one or more of any effective air/gas(s) pressure(s) and/or vacuum(s) for any effective outcome(s) for any cleaning(s) and/or surface treatment(s) such as, but not limited to any, "loosening of the contamination", "collecting the contaminant(s)", and/or "treating the surfaces", cannot be kept throughout location(s), part(s), component(s), space(s), and area(s) such as, but not limited to any, air duct(s) (4455), air duct(s) system(s) (4460), HVAC part(s) and equipment(s) (4465), HVAC unit(s) (4610), because the various air duct(s) (4455) connect with the various area(s) and room(s) (4410), and the deployed agent(s) (4510), that are emitted and/or deployed by the agent dispenser(s) (4505), used to treat various surface(s) such as, but not limited to any surface(s) inside any air duct(s) (4455), can enter into the various room(s) (4410), unless the various air duct(s) that open into and communicate with the various area(s) and room(s) (4410) such as, but not limited to any, supply duct(s) (4515) and return ducts (4520) are effectively sealed. Without being limited, and as known to those skilled the art, entire HVAC system may not be effectively and completely treated from one or more effective input location(s) because the various air duct(s) (4455), supply duct(s) (4515), and return ducts (4520), are not all effectively interconnected as one continuous sealed and communicating system of air duct(s) (4455).

Also, without being limited, the present invention, allows one or more of any, air duct(s) (4455), air duct system(s) (4460), supply duct(s) (4515), return ducts (4520), and/or HVAC parts and equipment(s) (4465), to be effectively, connected, interconnected, and/or seamlessly interconnected, preferably and without limitation, with the use one or more of any suitable and effective vent bypass system(s) (4415) and associated hose(s) (40)(4380), in any effective, communicating line, communicating conduit, circuit, open circuit, closed circuit, sealed circuit, sealed and communicating line, sealed and communicating system of conduit(s), sealed and communicating conduit(s), also including but not limited to any, isolated zone(s) (4540) and/or unisolated section(s) zone(s) (4545) and/or room(s) (4410) of one or more of any HVAC parts and equipment(s) (4465) such as, but not limited to any, air duct(s) (4455), air duct(s) system(s) (4460), supply duct(s) (4515), and/or return ducts (4520). This communicating system of one or more air duct(s) (4455), air duct(s) system(s) (4460), supply duct(s) (4515), and/or return ducts (4520) can be, without limitation, cleaned in any effective manner known to those skilled in the art, and more preferably treated with one or more of any deployed agent(s) (4510), to clean and/or treat any surfaces within these conduits and any connected HVAC part(s) and equipment(s) (4465) and HVAC unit(s) (4610) such as, but not limited to, those used for any, filtering, heating, humidification, dehumidification, movement, ventilation, and/or cooling, of any air and/or air flow(s).

Without being limited, the various air, gas(s), and/or deployed agent(s) (4510), can flow within the various air duct(s) (4455), air duct(s) system(s) (4460), and HVAC part(s) and equipment(s) (4465), at one or more of any suitable and effective flow rate(s), flow speed(s), flow velocity(s), pressure(s), and/or vacuum(s), and it is preferred without limitation, that these flow characteristic(s), pressure(s), and or vacuum(s), that can be applied and/or used by those skilled in the art, within the one or more air duct(s) (4455), air duct(s) system(s) (4460), and HVAC part(s) and equipment(s) (4465), are at least effective.

With reference to FIGS. 16-20 and 23, and according to an embodiment, and without limitation, the one or more of any air duct(s) (4455), in any building(s) (4470), that supply air/gas(s) from one or more of any HVAC part(s) and equipment(s) (4465) and HVAC unit(s) (4610) such as, but not limited to, those used for filtering, heating, humidification, dehumidification, movement, ventilation, and/or cooling, of any air, to any one or more area(s) and/or room(s) (4410), and more specifically and without limitation, the one or more of any air/gas entry vent(s) (4400), can be effectively, and preferably and without limitation, removably connected, either directly and/or indirectly, in any effective sealed manner known in the art, but preferably and without limitation with one or more of any suitable and effective vent bypass system(s) (4415) and/or hose(s) (40) (4380), to one or more of any air duct(s) (4455) that return air (4520) from any of the said one or more area(s) and/or room(s) (4410) back to the said HVAC part(s) and equipment(s) (4465) and HVAC unit(s) (4610), and more specifically and without limitation, to the one or more of any air/gas exit vent(s) (4405) that connect to the said return ducts (4520), so that the one or more, and more preferably and without limitation all, of the various air duct(s) (4455)(4460)(4465)(4515) (4520) and the various parts of the HVAC part(s) and equipment(s) (4465) and HVAC unit(s) (4610), known those skilled in the art, can all be effectively connected and/or linked together and can effectively communicate, and any, air, gas(s), and/or deployed agent(s) (4510), can effectively flow through, and more preferably and without limitation, circulate through and around, the effectively sealed and connected system of the one or more of any air duct(s) (4455), air supply duct(s) (4515), air/gas(s) entry vent(s) (4400), air/gas exit vent(s) (4405), air return ducts (4520), vent bypass system(s) (4415), hose(s) (40)(4380), and various HVAC part(s) and equipment(s) (4465) and HVAC unit(s) (4610), that is established. This can prevent the deployed agent(s) (4510) from entering or being deployed into any room(s) and/or area(s) (4410) where there are any air/gas entry vent(s) (4400) and/or air/gas exit vent(s) (4405). It is preferred, without limitation, that the various air duct(s) (4455)(4460)(4465)(4515)(4520) are effectively connected and communicate with one another using the one or more vent bypass system(s) (4415), it is more preferred without limitation, that the one or more air supply duct(s) (4515) are effectively connected and communicate with the one or more air return and/or air exit duct(s) (4520)(4455) using the one or more vent bypass system(s) (4415), it is even more preferred, without limitation, that the one or more air/gas(s) entry vent(s) (4400) are effectively connected and communicate with the one or more air/gas exit vent(s) (4405) using the one or more vent bypass system(s) (4415).

According to FIGS. 16-24, and without limitation, the deployed agent(s) (4510) can be, deployed, injected, administered, distributed, flowed, delivered, dispersed, and/or transmitted by one or more agent dispenser(s) (4505), in any suitable and effective manner known to those skilled in the art, into, interfaced with, removably interfaced with, and/or at, one or more of any suitable and effective location(s) of this said sealed and connected system of one or more of any, part(s), component(s), area(s), location(s), such as, but not limited to any, air duct(s) (4455), air supply duct(s) (4515), air/gas(s) entry vent(s) (4400), air/gas exit vent(s) (4405), hose(s) (40)(4380), vent bypass system(s) (4415), air return ducts (4520), HVAC unit(s) (4610), and/or HVAC part(s) and equipment(s) (4465), that is established. When these one or more of any, part(s), component(s), area(s), location(s), such as, but not limited to any, air duct(s) (4455), air supply duct(s) (4515), air/gas(s) entry vent(s) (4400), air/gas exit vent(s) (4405), hose(s) (40)(4380), vent bypass system(s) (4415), air return ducts (4520), HVAC unit(s) (4610), and/or HVAC part(s) and equipment(s) (4465), are effectively connected and sealed together, it is intended, without limitation, that the various room(s) and area(s) (4410) in which there are any air/gas(s) entry vent(s) (4400) and air/gas exit vent(s) (4405), are not exposed to the deployed agent(s) (4510). However, in certain situations known to those skilled in the art, and without being limited, the deployed agent(s) (4510) can also enter one or more of any, room(s), zone(s), area(s) (4410), and/or zone(s) of room(s) and/or area(s) (4525), for purposes including, but not limited to, treating the air and/or various surface(s) within those space(s) and room(s) (4410) with the deployed agent(s) (4510).

It is preferred, without limitation, that the deployed agent(s) (4510) are injected, administered, distributed, flowed, dispersed, transmitted, and/or flowed, into this said connected system of air duct(s) (4455) and the various HVAC part(s) and equipment(s) (4465) and/or HVAC unit(s) (4610), at least at or effectively near the one or more of any suitable and effective location(s) of any HVAC part(s) and equipment(s) (4465) and/or HVAC unit(s) (4610) such as, but not limited to, those used for any, filtering, heating, humidification, dehumidification, movement, ventilation, and/or cooling, of any air, and more preferably, and without limitation, in the area of any suitable fresh air intake and/or fresh air supply for the HVAC part(s) and equipment(s) (4465) and/or HVAC unit(s) (4610), and even more preferably, and without limitation, after any HVAC part(s) and equipment(s) (4465) and/or HVAC unit(s) (4610) used for moving and/or circulating air/gas(s) throughout various room(s) (4410) and/or building(s) (4470). It is more preferred, without limitation, that there are at least one, but more preferably, and without limitation, multiple treatment locations, and even more specifically one or more effective location(s), where the deployed agent(s) (4510) are injected and/or flowed into this said connected system of various, air duct(s) (4455), conduit(s), hose(s) (40)(4380), and the various HVAC part(s) and equipment(s) (4465) and/or HVAC unit(s) (4610), and even more specifically, and without limitation, along the connected and sealed system of various air duct(s) (4455), air supply duct(s) (4515), air/gas(s) entry vent(s) (4400), air/gas exit vent(s) (4405), vent bypass system(s) (4415), hose(s) (40)(4380), air return ducts (4520), and/or various HVAC part(s) and equipment(s) (4465) and/or HVAC unit(s) (4610), such as, but not limited to, those used for any, filtering, heating, humidification, dehumidification, movement, ventilation, and/or cooling, of any air, and more preferably, and without limitation, in the area of the fresh air intake and/or supply of the HVAC part(s) and equipment(s) (4465) and/or HVAC unit(s) (4610), and even more preferably, and without limitation, after any HVAC part(s) and equipment(s) (4465) and/or HVAC unit(s) (4610) used for moving any air and/or gas(s) (Herein called "Sealed Air/Gas Flow System" (4530), all in a manner known to those skilled in the art.

Also according to FIGS. 16-20 and FIG. 23, and without limitation, one or more of any suitable and effective, source(s) of pressurized air/gas(s), air pump(s), blower(s), fan(s), duct fan(s) (Herein called "Duct Fan(s)" (4535)), can also be located at and/or effectively integrated with, interfaced with, communicate with, and/or into, and preferably and without limitation, temporarily and/or removably, in a manner known to those skilled in the art, one or more of any suitable and effective location(s) such as, but not limited to any, air duct(s) (4455), sealed and connected system of one or more of any air duct(s) (4455), air gas(s) supply duct(s) (4515), air/gas(s) entry vent(s) (4400), air/gas exit vent(s) (4405), hose(s) (40)(4380), vent bypass system(s) (4415), orifice(s), air/gas(s) return ducts (4520), HVAC part(s) and equipment(s) (4465), HVAC unit(s) (4610), sealed zone(s) (4532), orifice(s), zone(s) of room(s) and/or area(s) (4525), sealed air/gas(s) flow system(s) (4530), isolated zone(s) (4540), unisolated section(s) zone(s) (4545), isolated targeted zone(s) of HVAC part(s) and equipment(s) (4465) and/or air duct(s) (4550), and/or one or more of any sealed air/gas flow system(s) (4530), and/or air duct system(s) (4460). Without limitation, the said duct fan(s) (4535) can move any suitable and effective quantity of any air, gas(s), vapor(s), and/or deployed agent(s) (4510), at any suitable and effective velocity, speed, cubic feet per minute, and/or volume of air/gas(s) flow(s).

Without being limited, the deployed agent(s) (4510), can be moved through any, air duct(s) (4455), air supply duct(s) (4515), air/gas(s) entry vent(s) (4400), air/gas exit vent(s) (4405), vent bypass system(s) (4415), hose(s) (40)(4380), orifice(s), air return ducts (4520), and/or HVAC unit(s) (4610) and various HVAC part(s) and equipment(s) (4465), sealed zone(s) (4532), and/or one or more of any sealed air/gas flow system(s) (4530), with one or more, including any effective combination(s) of, at one or more of any suitable location(s), any suitable and effective source(s) of pressurized air/gas(s), air pump(s), blower(s), fan(s), and/or any effective means to move any air/gas(s), such as, but not limited to any, duct fan(s) (4535), airflow source(s) used with any HVAC system(s) and/or HVAC unit(s) (4610) known to those skilled in the art, such as, but not limited to any HVAC unit(s) (4610) fan(s) and/or blower(s) that are a part of any HVAC unit(s) (4610), part(s), and/or component(s), that move air and/or gas(s) throughout one or more of any location(s), space(s), and/or area(s) such as, but not limited to any, building(s) (4470), room(s), zone(s), area(s) (4410), and/or zone(s) of room(s) and/or area(s) (4525), sealed air/gas(s) flow system(s) (4530), and/or sealed zone(s) (4532), as well as any source(s) of pressurized air/gas(s), air pump(s), blower(s), and/or fan(s), that are directly and/or indirectly a part of any agent dispenser(s) (4505). Without being limited, these one or more of any suitable and effective source(s) of pressurized air/gas(s), air pump(s), blower(s), fan(s), and/or any means to move any air/gas(s), can be located at one or more of any suitable and effective location(s) known to those skilled in the art, and can be operated at one or more of any suitable and effective time(s) and for any suitable and duration of time(s). Without being limited, the deployed agent(s) (4510) can be flowed in one or more of any suitable and effective direction(s) at any effective time(s) within any, air duct(s) (4455), air supply duct(s) (4515), air/gas(s) entry vent(s) (4400), air/gas exit vent(s) (4405), vent bypass system(s) (4415), hose(s) (40) (4380), orifice(s), air return ducts (4520), various HVAC part(s) and equipment(s) (4465) and/or HVAC unit(s) (4610), sealed zone(s) (4532), and/or one or more of any sealed air/gas flow system(s) (4530).

With reference to FIGS. 16-20 and FIG. 23, and without limitation, the one or more of any duct fan(s) (4535) can be effectively interfaced with and/or effectively communicate with, any, air duct(s) (4455), vent bypass system(s) (4415), hose(s) (40)(4380), connected system of air duct(s) (4455), HVAC part(s) and equipment(s) (4465) and/or HVAC unit(s) (4610), in any suitable and effective, configuration(s), mounting direction(s), and/or orientation(s). The airflow(s) from the said duct fan(s) (4535) can also, without limitation, flow in one or more of any suitable and effective direction(s). Also, and without being limited, the one or more duct fan(s) (4535) can suitably and effectively communicably and removably interface, preferably and without limitation in any hermetically sealed manner, and more preferably and without limitation, be effectively located to and/or within any, air duct(s) (4455), hose(s) (40)(4380), sealed zone(s) (4532), and/or one or more of any sealed air/gas flow system(s) (4530), in any effective manner known to those skilled in the art, but at least at and/or with one or more of any suitable and effective location(s) and/or part(s), of one or more of any sealed zone(s) (4532) and/or one or more of any sealed air/gas flow system(s) (4530) such as, but not limited to any, air duct(s) (4455), vent bypass system(s) (4415), hose(s) (40) (4380), connected system of air duct(s) (4460), and/or the various HVAC part(s) and equipment(s) (4465) and/or HVAC unit(s) (4610), and even more specifically the connected and sealed system of various air duct(s) (4455)(4460)(4530), air supply duct(s) (4515), air/gas(s) entry vent(s) (4400), air/gas exit vent(s) (4405), vent bypass system(s) (4415), hose(s) (40)(4380), air return ducts (4520), and/or various HVAC part(s) and equipment(s) (4465) and/or HVAC unit(s) (4610), such as, but not limited to, those used for any, filtering, heating, humidification, dehumidification, movement, ventilation, and/or cooling, of any air.

Without being limited, the deployed agent(s) (4510) can be, deployed, injected, administered, distributed, flowed, delivered, dispersed, and/or transmitted, by the one or more said agent dispenser(s) (4505), in any suitable and effective manner and with any suitable and effective agent dispenser(s) (4505), known to those skilled in the art, at one or more of any suitable and effective, temperature(s), flow rate(s), flow speed(s), cubic feet per minute flow(s), mass flow(s), particle size(s), number mass(s), and/or concentration(s), of the air/gas(s) and/or deployed agent(s) (4510). It is preferred, without limitation, that the deployed agent(s) (4510) can move, flow, circulate, and/or completely circulate, through and/or throughout the one or more effectively connected and/or sealed, sealed zone(s) (4532), sealed air/gas flow system(s) (4530), air duct(s) (4455), conduit(s), hose(s) (40)(4380), HVAC part(s) and equipment(s) (4465) and/or HVAC unit(s) (4610), any connected and sealed system of various air duct(s) (4455), air supply duct(s) (4515), air/gas(s) entry vent(s) (4400), air/gas exit vent(s) (4405), vent bypass system(s) (4415), hose(s) (40)(4380), air return ducts (4520), and/or open system(s) (4565).

Figure 18:
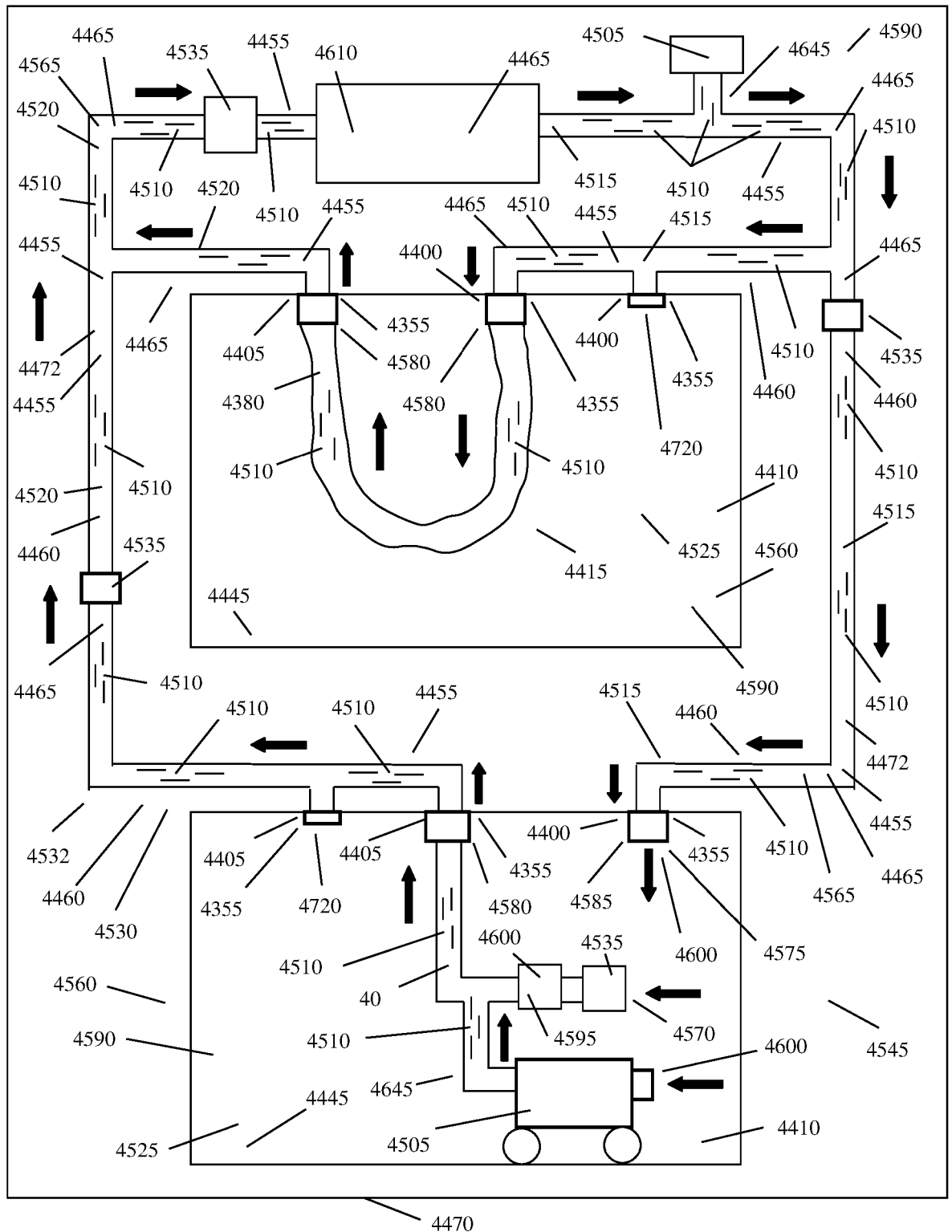
FIG. 18 is a schematic diagram of two story building showing at least one room on each floor and the rooms communicate with at least one system of shared air ducts that are effectively sealed on one end, and communicate with at least one air entry filter on the sealed end.
Figure 19:
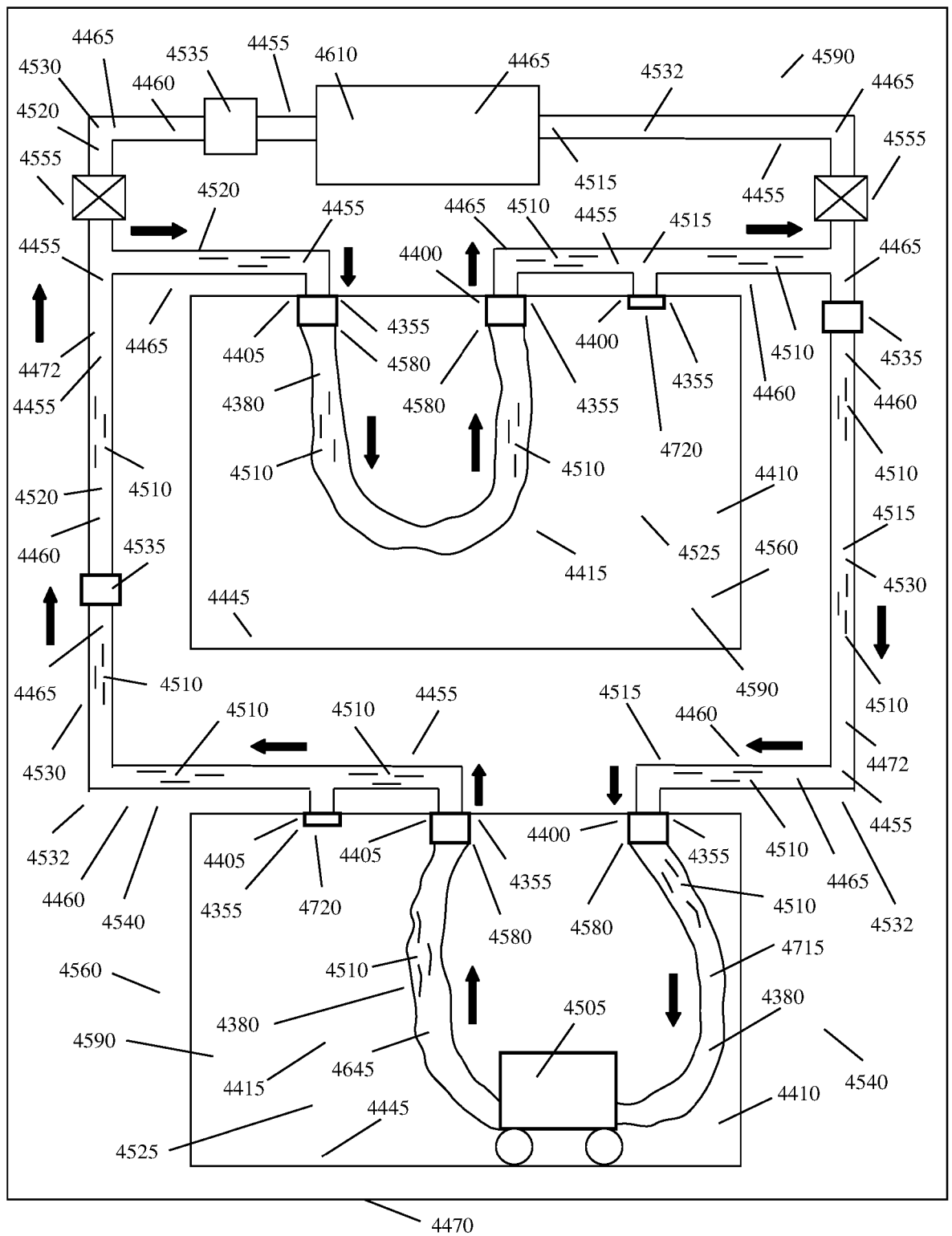
FIG. 19 is a schematic side view of a two story building showing at least one room on each floor, where the at least one room communicates with at least one system of shared air ducts to supply air into the at least one room and to provide a means for air to exit the at least one room, and at least one of the at least one room is isolated from communicating with the another room.
Figure 20:
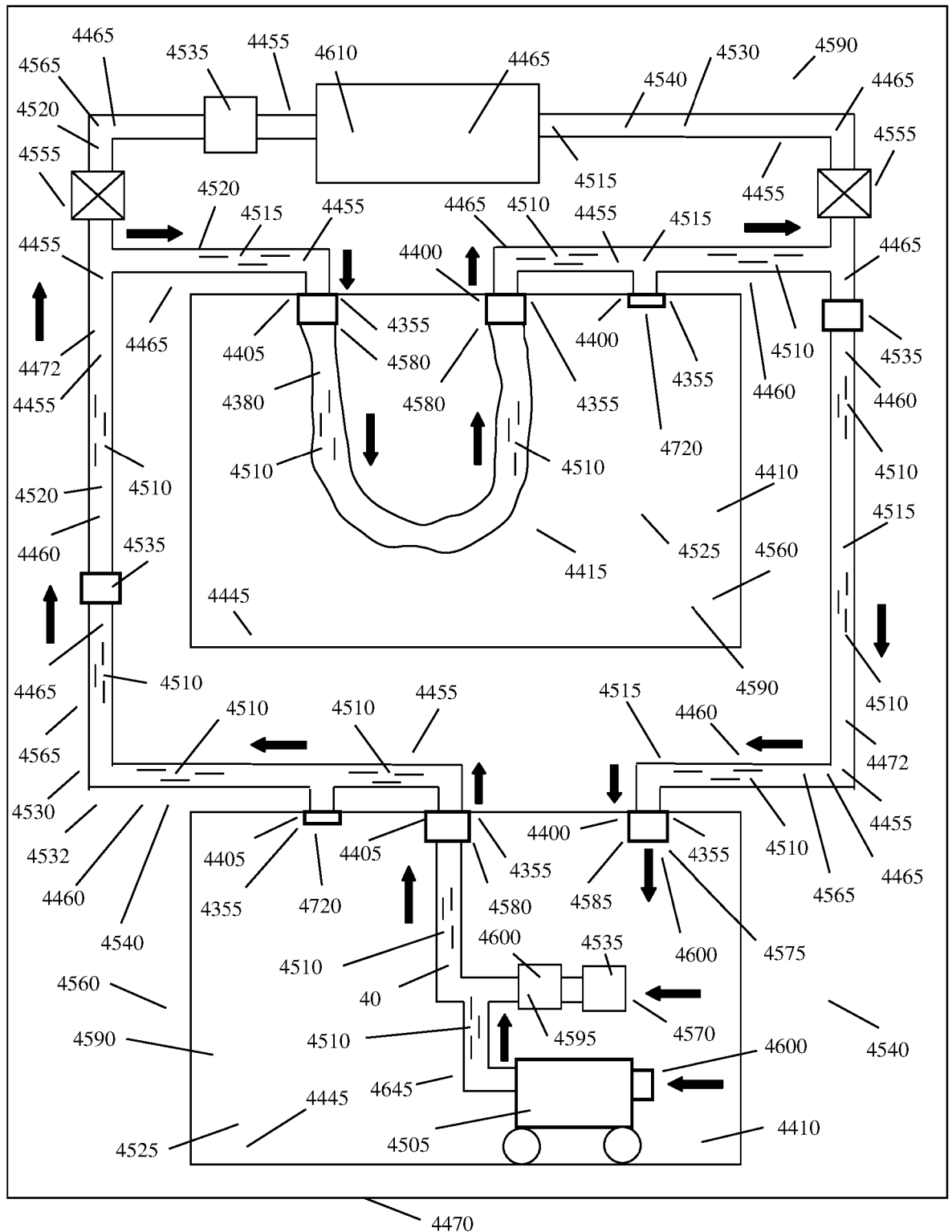
FIG. 20 is a schematic side view of a two story building showing at least one room on each floor, where the at least one room communicates with at least one system of shared air ducts to supply air into the at least one room to provide a way for air to exit the at least one room, and at least one of the at least one room is isolated from communicating with another room by effectively sealing various effective ends of various air ducts that provide air into and out of the at least one isolated room.
Figure 21:
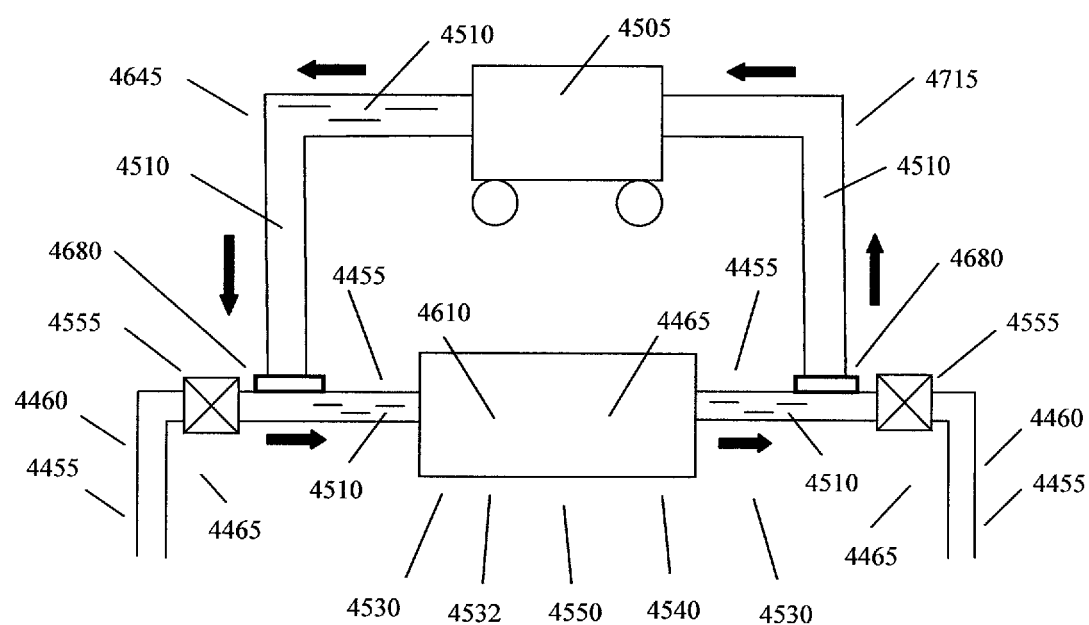
FIG. 21 is a schematic diagram of isolated and sealed off air ducts that communicate with at least one HVAC unit that contains one or more of any apparatus(s) used for purposes such as, but not limited to any filtering, heating, humidification, dehumidification, movement, ventilation, and/or cooling, of any air and/or air flow(s) that pass through the HVAC unit.

According to FIGS. 19-21, and without being limited, the one or more of the said sealed and connected system(s) of the one or more of any air duct(s) (4455), air supply duct(s) (4515), air/gas(s) entry vent(s) (4400), orifice(s), air/gas exit vent(s) (4405), vent bypass system(s) (4415), hose(s) (40) (4380), air return ducts (4520), and/or various HVAC part(s) and equipment(s) (4465) and/or HVAC unit(s) (4610), that is established, can also be confined and/or isolated to one or more of any suitable and effective zone(s) and/or area(s) (Herein called "Sealed Zone(s)" (4532)). It is preferred, without limitation, that the sealed zone(s) (4532) are effectively sealed and/or isolated in a manner and/or with one or more suitable and effective means known to those skilled in the art (Herein called "Air Duct Seal(s) (4555)". The sealed zone(s) (4532) can include and/or be, without limitation, any suitable and effective, size, air volume, number of air duct(s) (4455), number of air/gas(s) entry vent(s) (4400), number of air/gas exit vent(s) (4405), number of vent bypass system(s) (4415), number of hose(s) (40)(4380), number of HVAC part(s) and equipment(s) (4465), number of HVAC unit(s) (4610), number of air supply duct(s) (4515), number of air return duct(s) (4520), complexity, height, number of building(s) (4470), number of floor(s) (4560) of any building(s) (4470), and/or include one or more of any, room(s), zone(s), area(s), and/or zone(s) of room(s) and/or area(s) (4410). Also, according to FIGS. 16-20 and FIG. 23, and without being limited, one or more of any vent opening(s) (4355), air/gas(s) entry vent(s), and/or air/gas(s) exit vent(s), can also be effectively covered and/or sealed with one or more of any suitable and effective cover(s) and/or seal(s) (Herein called "Orifice Seal(s)") (4720) that can be any suitable and effective size(s), shape(s), design(s), thickness(s), length(s), width(s), height(s), material(s), and/or combination of material(s). Without being limited, the present invention, including but not limited to any of its embodiments, can apply to any, style of building(s), design of building(s), and number of stories or floors (4560) that any building may have including but not limited to any, one story and/or floor building(s) and/or multi story and/or floor building(s), known to those skilled in the art.

With reference to FIGS. 18 and 20, and without limitation, the deployed agent(s) (4510) and any accompanying air/gas(s) can also be, deployed, injected, and/or flowed, into one or more of any suitable and effective locations of any open and connected system(s) (4565) of various connected, air duct(s) (4455), air supply duct(s) (4515), air/gas(s) entry vent(s) (4400), air/gas exit vent(s) (4405), vent bypass system(s) (4415), hose(s) (40)(4380), air return ducts (4520), and/or various HVAC part(s) and equipment(s) (4465) and/or HVAC unit(s) (4610), conduit(s), hose(s) (40)(4380), and even more preferably, and without limitation, one or more of any suitable and effective location(s) of the connected and sealed system of various air duct(s) (4455), air supply duct(s) (4515), air/gas(s) entry vent(s) (4400), air/gas exit vent(s) (4405), vent bypass system(s) (4415), hose(s) (40)(4380), air return ducts (4520), and/or various HVAC part(s) and equipment(s) (4465) and/or HVAC unit(s) (4610) (Herein called "Open System(s)" (4565)), where the deployed agent(s) (4510) are effectively deployed at least at one or more of any suitable and effective end(s) and/or beginning(s) (Herein called ("Start Location(s) of Open System" (4570)) of this said open system(s) (4565), and then flowed through the said various part(s), component(s), space(s), location(s), and conduit(s), and then exit at one or more of any other suitable and effective open end(s) (Herein called "Open End Location(s) of Open System" (4575)) of this said open system(s) (4565). It is preferred, without limitation that the deployed agent(s) (4510) are at least, without limitation, deployed, injected, and/or flowed, into one or more additional suitable and effective location(s) of this said open system(s) (4565).

Without being limited, the one or more of any sealed air/gas flow system(s) (4530), sealed zone(s) (4532), and open system(s) (4565), can be any suitable and effective, size(s), shape(s), complexity(s), include multiple building (4470) level(s) or floor(s) (4560), and include both small and large connected and interconnected systems of various, air duct(s) (4455), air supply duct(s) (4515), air/gas(s) entry vent(s) (4400), air/gas exit vent(s) (4405), vent bypass system(s) (4415), hose(s) (40)(4380), air return ducts (4520), and/or various HVAC part(s) and equipment(s) (4465) and/or HVAC unit(s) (4610).

Also, without being limited, the establishment of any sealed zone(s) (4532) and/or open system(s) (4565) can also be used to isolate, encompass, include, seal together, connect, and/or envelop, one or more of any, equipment(s), component(s), area(s), and/or space(s), such as, but not limited to any, fan(s), blower(s), duct fan(s) (4535), air duct(s) (4455), air duct system(s) (4460), filter assembly(s) (not shown), filter holding apparatus(s) (not shown), and/or any other HVAC part(s) and equipment(s) (4465) and/or HVAC unit(s) (4610), for various activities and/or any combination of any suitable and effective activities such as, but not limited to, loosening the contamination(s), collecting the contaminant(s), treating the surfaces, cleaning various surface(s), within and/or on these various part(s), equipment(s), area(s) and/or space(s). Without being limited, this can also be used for cleaning and treating various HVAC part(s) and equipment(s) (4465) and/or HVAC unit(s) (4610), as well as before, during, and/or after, changing and/or replacing any air/gas(s) filter(s) (not shown). Without being limited the one or more of any air/gas(s) filter(s) (not shown) located in these various location(s), such as, but not limited to inside various HVAC system(s) and component(s) and/or HVAC unit(s) (4610), can be treated with any effective deployed agent(s) (4510) before, during, and/or after their removal. It is preferred, without limitation, that the various filter holding apparatus(s) (not shown) are effectively treated with the deployed agent(s) (4510) for purposes including, but not limited to, the effective decontamination of their various surface(s), at least before any new air/gas(s) filter(s) (not shown) are installed, and after the old air/gas(s) filter(s) (not shown) are removed from any suitable filter holding apparatus(s) (not shown). The air/gas(s) filter(s) can be, without limitation, any suitable and effective filter(s) known to those skilled in the art, for any suitable and effective application(s) known to those skilled in the art.

With reference to FIG. 21, and without being limited, one or more section(s) of any, air duct(s) (4455), air supply duct(s) (4515), air return duct(s) (4520), HVAC part(s) and equipment(s) (4465), HVAC unit(s) (4610), and/or HVAC system, can also be effectively sealed off in a manner known to those skilled in the art, but preferably and without limitation with any suitable number, size, and shape, of any effective air duct seal(s) (4555), so that they cannot communicate with other one or more of any connecting air duct(s) (4455), room(s) (4410), and/or system of of air duct(s) (4460), so that one or more of any HVAC part(s) and equipment(s) (4465) and/or HVAC unit(s) (4610), such as, but not limited to, those used for any, filtering, heating, humidification, dehumidification, movement, ventilation, and/or cooling, of any air/gas(s), as well as any communicating air duct(s) (4455), can be subjected to the one or more of any of the said step(s) and/or activities such as, but not limited to, "Loosening the Contamination(s)", "Collecting the Contaminant(s)", and/or "Treating the Surfaces", on and/or within these various area(s), part(s), and/or space(s).

According to FIGS. 16-24, and without being limited, the one or more agent dispenser(s) (4505) can suitably and effectively communicably and removably interface, preferably and without limitation in any hermetically sealed manner, known to those skilled in the art, at or with one or more of any suitable and effective, part(s), location(s), component(s), area(s), and/or space(s), such as, but not limited to any, air duct system(s) (4460), sealed zone(s) (4532) sealed air/gas flow system(s) (4530), air duct(s) (4455), connected and sealed system of various air duct(s) (4455), air supply duct(s) (4515), air/gas(s) entry vent(s) (4400), air/gas exit vent(s) (4405), vent bypass system(s) (4415), hose(s) (40)(4380), air return ducts (4520), and/or various HVAC part(s) and equipment(s) (4465) and/or HVAC unit(s) (4610), such as, but not limited to, those used for any, filtering, heating, humidification, dehumidification, movement, ventilation, and/or cooling, of any air.

Without being limited, the deployed agent(s) (4510) can be, deployed, injected, administered, distributed, flowed, delivered, dispersed, and/or transmitted, by the one or more said agent dispenser(s) (4505), in any suitable and effective manner known to those skilled in the art, at one or more of any suitable and effective, temperature(s), flow rate(s), flow speed(s), cubic feet per minute flow(s), mass flow(s), particle size(s), particle number(s), number mass(s), and/or concentration(s), of the air/gas(s) and/or deployed agent(s) (4510). It is preferred, without limitation, that the deployed agent(s) (4510) can move, flow, circulate, and/or completely circulate, through and/or throughout, the one or more of any area(s) such as, but not limited to any, effectively connected and/or sealed zone(s) (4532), sealed air/gas flow system(s) (4530), and/or zone(s) (4540).

Without being limited, the one or more of any air/gas entry vent(s) (4400) and the one or more of any air/gas exit vent(s) (4405), and/or any other entry and/or exit orifice(s), can be directly and/or indirectly connected with one or more of any suitable and effective conduit(s), tube(s), and/or hose(s) (40)(4380), and preferably and without limitation, with one or more of any suitable and effective vent bypass system (4415), so that air, deployed agent(s) (4510), and/or gas(s), may effectively pass from one or more of any air duct(s) (4455), and more particularly and without limitation, any air duct(s) (4455) that supply air/gas(s) (4515) to the one or more area(s) and/or room(s) (4410), preferably and without limitation through the one or more of any air/gas entry vent(s) (4400) and/or any other entry orifice(s), through the one or more of any conduit(s), tube(s), vent bypass system(s) (4415), and/or hose(s) (40)(4380), and preferably and without limitation through the one or more of any air/gas exit vent(s) (4405) and/or any other exit orifice(s), and then to one or more of any air duct(s) (4455) that return air/gas(s) (4520) to the one or more of any HVAC part(s) and equipment(s) (4465) and/or HVAC unit(s) (4610), and/or to one or more of any air duct(s) (4455) that reconnect, recirculate, and/or connect back, to one or more of any air duct(s) (4455) that supply air/gas(s) (4515) to the one or more of any area(s) and/or room(s) (4410).

It is preferred, without limitation, that all of the various air/gas(s) entry vent(s) (4400) and air/gas exit vent(s) (4405), that are preferably within, connected to, and/or communicating with, one or more of any, air duct(s) (4455), system of air duct(s) (4460), air supply duct(s) (4515), air return duct(s) (4520), sealed air/gas(s) flow system(s) (4530), sealed zone(s) (4532), isolated zone(s) (4540), within any building(s) (4470), and more preferably within an entire building(s) (4470), are effectively covered, and more preferred without limitation these air/gas(s) vent(s) (4400)(4405) are effectively removably sealed, and even more preferred without limitation these air/gas(s) vent(s) (4400)(4405) are effectively removably sealed in a manner that is hermetic or about hermetically sealed. Without being limited, these various air/gas(s) vent(s) (4400)(4405), and/or any other suitable suitable and effective orifice(s) (not shown) that may be cut and/or made present in one or more of any suitable location(s) of any air duct(s) (4455), in a manner known to those skilled in the art, can be effectively covered and/or sealed with one or more of any suitable and effective means to cover and/or seal any air/gas(s) vent(s) (4400)(4405) and/or orifice(s) (not shown) known to those skilled in the art, such as, but not limited to any, vent cover apparatus(s) (3900), cover plate(s) (4180) that preferably and without limitation includes at least one effective seal(s) and/or sealing ring(s) (4190), vent bypass system(s) (4415), and/or air duct seal(s) (4555).

Also, and without being limited, it is preferred that these said one or more means to cover and/or seal any air/gas(s) vent(s) (4400)(4405) and/or orifice(s) (not shown), can also interface and connect with, and/or removably interface and connect with, in any manner known to those skilled in the art, one or more of any suitable and effective conduit(s), tube(s), and/or hose(s) (40)(4380), thus preferably forming one or more effective vent bypass system(s) (4415). Without being limited, the said means to cover and/or seal any air/gas(s) vent(s) (4400)(4405) and/or orifice(s) (not shown), such as, but not limited to any vent bypass system(s) (4415) can effectively directly and/or indirectly interface with, and/or removably interface with, in any manner known to those skilled in the art, one or more of any air duct(s) (4455) that supply air (4515) and/or air/gas(s) entry vent(s) (4400), and one or more of any air duct(s) (4455) that returns air (4520) and/or air/gas(s) exit vent(s) (4405). The one or more of any suitable and effective conduit(s), tube(s), hose(s) (40)(4380) and/or vent bypass system(s) (4415), can and without limitation, effectively directly and/or indirectly connect and communicate with the one or more of any air duct(s) (4515) and/or air/gas(s) entry vent(s) (4400) that supply air to one or more area(s) and room(s) (4410), to the one or more of any air duct(s) (4520) and/or air/gas(s) exit vent(s) (4405) that return air/gas(s) from these one or more area(s) and room(s) (4410) back to the HVAC part(s) and equipment(s) (4465) and/or HVAC unit(s) (4610), so that air/gas(s), deployed agent(s) (4510), and/or gas(s) can effectively pass from the air/gas(s) supply duct(s) (4515) and air/gas(s) entry vent(s) (4400), to the air/gas(s) exit vent(s) (4405) that connect to the said return ducts (4520) and eventually back to the HVAC part(s) and equipment(s) (4465) and/or HVAC unit(s) (4610). Without being limited, the air/gas(s) and/or deployed agent(s) can also move in the opposite direction(s). Also, and without being limited, one or more of any air supply duct(s) (4515) and air/gas(s) entry vent(s) (4400) in certain, unique, and/or specific area(s), zone(s), and/or room(s) (4410) can also be effectively connected to one or more of any air/gas exit vent(s) (4405) and air return ducts (4520) in other certain, unique, different, and/or specific area(s), zone(s), and/or room(s) (4410).

According to FIGS. 16-20 and FIG. 23, and without being limitation, one or more of any suitable and effective means and apparatus design(s) known to those skilled in the art, can be used to cover and/or seal any air/gas(s) vent(s) (4400) (4405) and/or orifice(s) (not shown), such as, but not limited to any suitable and effective, plate(s), cover(s), block(s), and/or vent cover door(s) (3930) (Herein called "Cover(s)" (4580)). The cover(s) (4580) can be effectively connected to, interfaced with, and/or include one or more of any suitable and effective means known to those skilled in the art, to directly, indirectly, and/or removably, connect with, one or more of any suitable and effective conduit(s), tube(s), and/or hose(s) (40)(4380), so that any, air, gas(s), and/or any deployed agent(s) (4510), may effectively flow to and/or from the various air duct(s) (4455)(4515)(4520), air/gas(s) vent(s) (4400)(4405), and/or other orifice(s) (not shown), through the one or more of any cover(s) (4580), as well as through the one or more of any connected conduit(s), tube(s), and/or hose(s) (40) (4380), and more preferably through various vent bypass system(s) (4415), that are all directly and/or indirectly connected to one another and/or communicate with one another through the various said conduits and/or hose(s) (40)(4380). It is preferred, without limitation, that these various part(s) and component(s) are removably and effectively sealed to one another in a manner known to those skilled in the art, and additionally at least one effective seal(s) (not shown) can also be effectively positioned between the various various air duct(s) (4455)(4515) (4520) and/or air/gas(s) vent(s) (4400)(4405), and the various cover(s) (4580).

According to FIGS. 16-21 and FIG. 23, and without limitation, the various air duct(s) (4455), air supply duct(s) (4515), air/gas(s) entry vent(s) (4400), air/gas exit vent(s) (4405), hose(s) (40)(4380), vent bypass system(s) (4415), orifice(s) (not shown), air return ducts (4520), cover(s) (4580), and/or various HVAC part(s) and equipment(s) (4465) and/or HVAC unit(s) (4610), can be connected and/or interconnected in various ways known to those skilled in the art, for activities such as, but not limited to, loosening the contamination(s), collecting the contaminant(s), and treating the surfaces, of the various, conduit(s), air duct(s), and HVAC part(s) and equipment(s) (4465) and/or HVAC unit(s) (4610).

Figure 16:
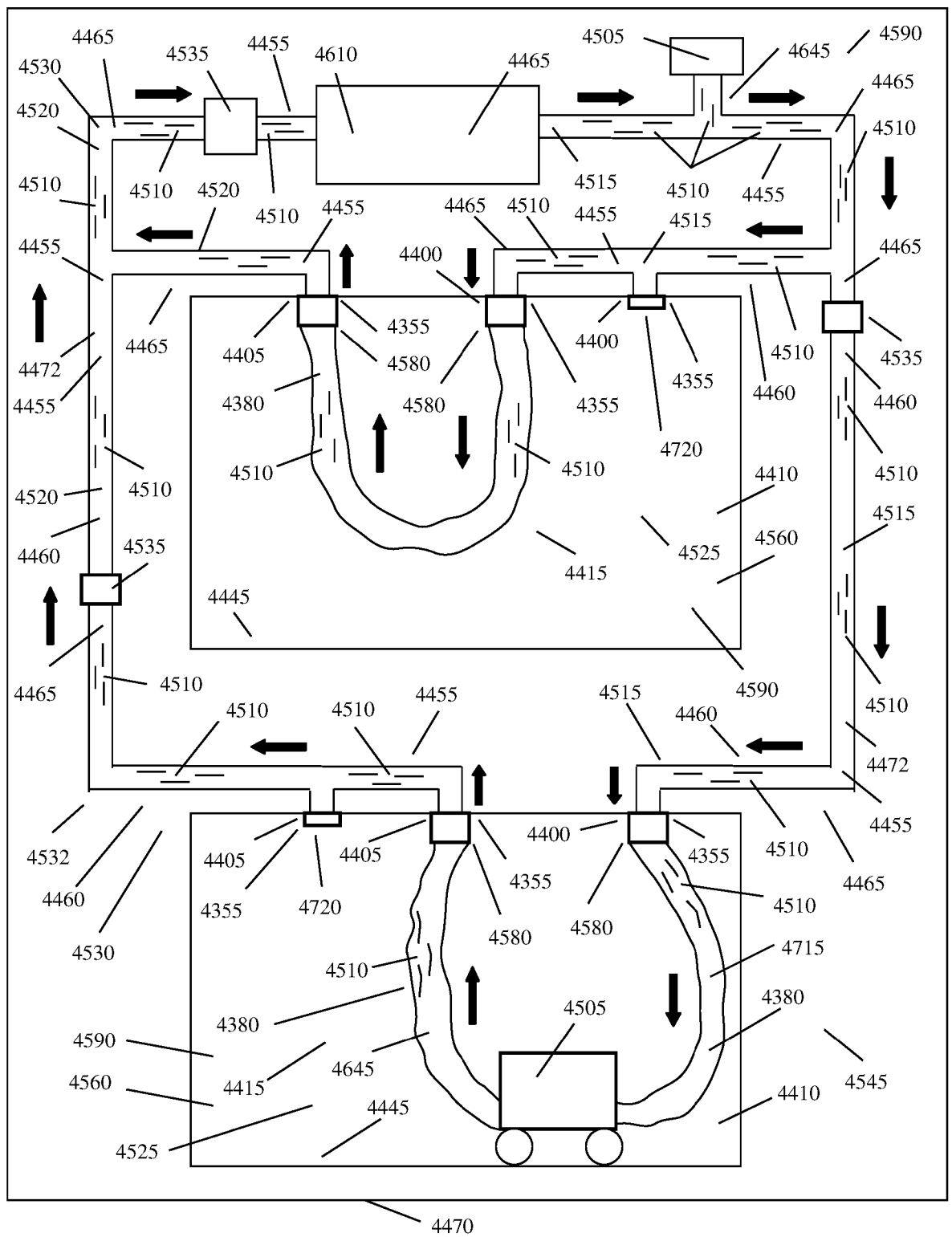
FIG. 16 is a schematic diagram of a two story building showing at least one room and the rooms communicate with at least one system of shared air ducts that communicate with at least one HVAC system that supply air to the at least one room on each floor in accordance with the present invention.
Figure 17:
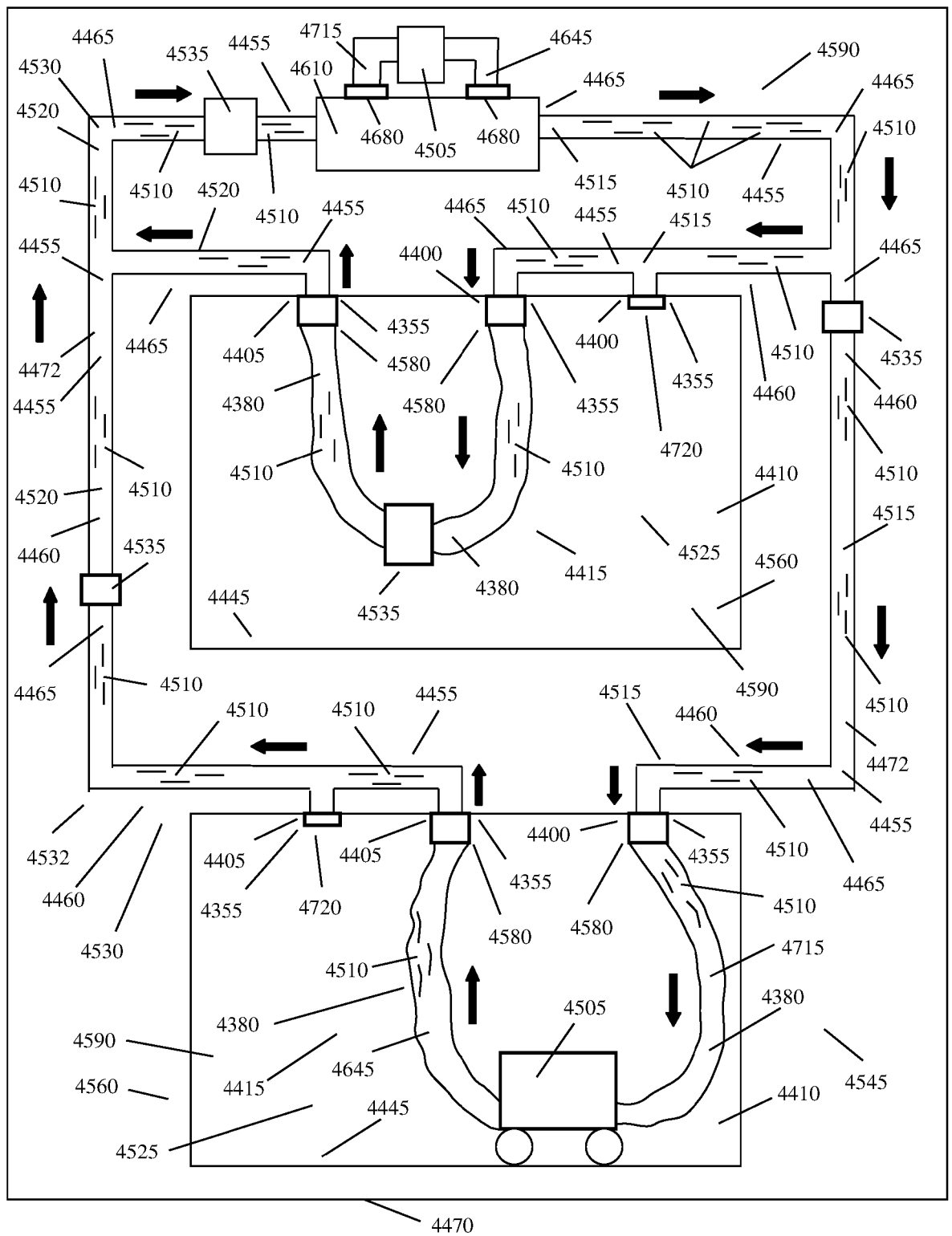
FIG. 17 is a schematic diagram of a two story of building showing at least one room on each floor and the rooms are connected by at least one system of shared air ducts that communicate with at least one HVAC system that supply air to the at least one room on each floor with a duct fan located in a hose, which connects flow between entry and exit vents on a second floor.

In one configuration, and according to FIGS. 16-17, and without limitation, the various air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), and/or various HVAC part(s) and equipment(s) (4465) and/or HVAC unit(s) (4610), that are connected and/or interconnected, to form one or more of any effective sealed air/gas flow system(s) (4530), can be effectively connected and/or interconnected with one or more equipment(s) such as, but not limited to any, agent dispenser(s) (4505) and/or duct fan(s) (4535), so that the air/gas(s) and/or deployed agent(s) (4510) that are deployed into the connected conduits can circulate and/or fully circulate through all of the various connected and/or interconnected part(s), space(s), area(s), and/or component(s) such as, but not limited to any, air duct(s) (4455), air supply duct(s) (4515), air/gas(s) entry vent(s) (4400), air/gas exit vent(s) (4405), hose(s) (40)(4380), vent bypass system(s) (4415), air return ducts (4520), various HVAC part(s) and equipment(s) (4465) and/or HVAC unit(s) (4610), and/ or sealed air/gas flow system(s) (4530).

In another configuration, and according to FIG. 18, and without limitation, the various air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), and/or various HVAC part(s) and equipment(s) (4465) and/or HVAC unit(s) (4610), that are connected and/or interconnected, to form one or more of any effective sealed air/gas flow system(s) (4530), can be effectively connected and/or interconnected with one or more equipment(s) such as, but not limited to any, agent dispenser(s) (4505), air/gas(s) entry filter(s) (4595), duct fan(s) (4535), and/or air/gas exit filter(s) (4585), so that the air/gas(s) and/or deployed agent(s) (4510) that are deployed into the connected conduits can flow effectively through all of the various connected and/or interconnected part(s), space(s), area(s), and/or component(s) such as, but not limited to any, air duct(s) (4455), air supply duct(s) (4515), air/gas(s) entry vent(s) (4400), hose(s) (40)(4380), vent bypass system(s) (4415), air/gas exit vent(s) (4405), air return ducts (4520), various HVAC part(s) and equipment(s) (4465) and/or HVAC unit(s) (4610), and/or sealed air/gas flow system(s) (4530), and then flow through one or more air/gas exit filter(s) (4585) and exit into the surrounding environment (4590). Without being limited, the surrounding environment (4590) can include, but is not limited to any, area(s), space(s), room(s) (4410), atmosphere(s), that is not connected to any, and/or is outside of any connected, sealed, and/or communicating, system of various part(s), component(s), area(s), and/or space(s) such as, but not limited to any, air duct(s) (4455), air supply duct(s) (4515), air/gas(s) entry vent(s) (4400), hose(s) (40) (4380), vent bypass system(s) (4415), air/gas exit vent(s) (4405), air return ducts (4520), various HVAC part(s) and equipment(s) (4465) and/or HVAC unit(s) (4610), air duct system(s) (4460), sealed air/gas flow system(s) (4530), sealed zone(s) (4532), and/or open system(s) (4565).

In still another configuration, and according to FIG. 19, and without limitation, the various air duct(s) (4455), air supply duct(s) (4515), air/gas(s) entry vent(s) (4400), hose(s) (40) (4380), air/gas exit vent(s) (4405), vent bypass system(s) (4415), orifice(s), air return ducts (4520), and/or various HVAC part(s) and equipment(s) (4465) and/or HVAC unit(s) (4610), that are connected and/or interconnected, and form one or more of any effective sealed zone(s) (4532), can be effectively connected and/or interconnected with one or more equipment(s) such as, but not limited to any, agent dispenser(s) (4505), and/or duct fan(s) (4535), so that the air/gas(s) and/or deployed agent(s) (4510) that are deployed into the connected conduits can circulate and/or fully circulate through all of the various connected and/or interconnected part(s), space(s), area(s), and/or component(s) such as, but not limited to any, air duct(s) (4455), air supply duct(s) (4515), air/gas(s) entry vent(s) (4400), air/gas exit vent(s) (4405), vent bypass system(s) (4415), hose(s) (40)(4380), air return ducts (4520), various HVAC part(s) and equipment(s) (4465) and/or HVAC unit(s) (4610), and/or sealed air/gas flow system(s) (4530).

In still another additional configuration, and according to FIG. 20, and without limitation, the various air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), and/or various HVAC part(s) and equipment(s) (4465) and/or HVAC unit(s) (4610), that are connected and/or interconnected, and form one or more of any effective sealed zone(s) (4532), can be effectively connected and/or interconnected with one or more equipment(s) such as, but not limited to any, agent dispenser(s) (4505), duct fan(s) (4535), and/or air/gas exit filter(s) (4585), so that the air/gas(s) and/or deployed agent(s) (4510) that are deployed into the connected conduits can flow effectively through all of the various connected and/or interconnected part(s), space(s), area(s), and/or component(s) such as, but not limited to any, air duct(s) (4455), air supply duct(s) (4515), air/gas(s) entry vent(s) (4400), air/gas exit vent(s) (4405), hose(s) (40) (4380), vent bypass system(s) (4415), air return ducts (4520), various HVAC part(s) and equipment(s) (4465), and/or sealed air/gas flow system(s) (4530), and then flow through one or more air/gas(s) exit filter(s) (4585) and exit into the surrounding environment (4590).

With reference to FIGS. 18 and 20, and without being limited, any air/gas(s) and/or deployed agent(s) (4510) that enters and/or exits the one or more sealed air/gas flow system(s) (4530) and/or sealed zone(s) (4532), can first pass through one or more of any effective entry filter(s) (4595), and then flow through various connected and/or interconnected, air duct(s) (4455), air supply duct(s) (4515), air/gas(s) entry vent(s) (4400), air/gas exit vent(s) (4405), hose(s) (40) (4380), vent bypass system(s) (4415), air return ducts (4520), HVAC part(s) and equipment(s) (4465) and/or HVAC unit(s) (4610), and/or sealed air/gas flow system(s) (4530), and then flow through one or more air/gas(s) exit filter(s) (4585), and/or sealed zone(s) (4532), and then exit into the surrounding environment (4590) through one or more of any effective exit filter(s) (4585) that can be any suitable and effective filters such as, but not limited to any, HEPA filter(s), ULPA filter(s), and/or any vapor capture filter(s), as known to those skilled in the art, before the air/gas(s) and/or deployed agent(s) (4510) exits into the surrounding environment (4590), preferably, and without limitation, after the time for administering, distributing, flowing, delivering, dispersing, and/or transmitting the deployed agent(s) has finished. Without being limited, it is preferred that only the external air/gas(s) that is used, provided, and/or flowed, is effectively and suitably filtered, and more preferably by one or more of any suitable and effective entry filter(s) (4595), before the said external air/gas(s) is introduced, injected, and/or flowed, into the one or more of any connected and/or interconnected part(s), space(s), area(s), and/or component(s) such as, but not limited to any, air duct(s) (4455), air supply duct(s) (4515), air/gas(s) entry vent(s) (4400), air/gas exit vent(s) (4405), hose(s) (40)(4380), vent bypass system(s) (4415), air return ducts (4520), HVAC part(s) and equipment(s) (4465) and/or HVAC unit(s) (4610), air duct system(s) (4460), sealed air/gas flow system(s) (4530), and/or sealed zone(s) (4532). Without being limited, external air/gas(s) can be sourced from one or more of any suitable and effective location(s) such as, but not limited to those in the surrounding environment(s) (4590) outside of the said connected and/or interconnected part(s), space(s), area(s), and/or component(s).

Alternatively, and with reference to FIGS. 16-24, and without limitation, the various, part(s), component(s), area(s), and/or space(s) such as, but not limited to any, air duct(s) (4455), air supply duct(s) (4515), air/gas(s) entry vent(s) (4400), hose(s) (40)(4380), vent bypass system(s) (4415), air/gas exit vent(s) (4405), air return ducts (4520), various HVAC part(s) and equipment(s) (4465) and/or HVAC unit(s) (4610), air duct system(s) (4460), sealed air/gas flow system(s) (4530), open system(s) (4565), and/or sealed zone(s) (4532), can also be subjected to and/or undergo the one or more of any of the said step(s) and/or activities such as, but not limited to, "Loosening the Contamination(s)", "Collecting the Contaminant(s)", and/or "Treating the Surfaces", either with and/or without the use of the one or more of any suitable and effective filter(s) (4600)(4595)(4585) at one or more of any suitable and effective location(s). For example, and without limitation, during the activity of "Treating the Surfaces", the deployed agent(s) (4510) can be effectively circulated through and/or around the said various, part(s), component(s), area(s), and/or space(s), as well as any, air duct system(s) (4460), sealed air/gas flow system(s) (4530), and/or sealed zone(s) (4532), without the use of any air/gas(s) filter(s) (4600)(4595) (4585).

With reference to FIGS. 16-18, and without limitation, an apparatus and method of another embodiment of the present invention comprises numerous steps to mechanically clean and/or treat with one or more of any deployed agent(s) (4510), the one or more of any area(s), surface(s), and/or space(s), on, inside of, and/or within one or more of any, air duct(s) (4455), air supply duct(s) (4515), air/gas(s) entry vent(s) (4400), air/gas exit vent(s) (4405), hose(s) (40) (4380), vent bypass system(s) (4415), orifice(s), air return ducts (4520), air shaft(s) (4472), room(s) (4410), and various HVAC part(s) and equipment(s) (4465) and/or HVAC unit(s) (4610), open system(s) (4565), sealed air/gas flow system(s) (4530), and/or air duct system(s) (4460). These one or more steps can be, without limitation, taken in any number of any suitable and effective order(s) and/or combination(s), and one or more of these steps and/or one or more of any part(s) of these steps can also be omitted and/or modified, all in a manner known to those skilled in the art. These various steps and/or activities can also, and without limitation, take place at one or more of any suitable and effective locations, and at one or more of any suitable and effective time(s) and for any suitable and effective duration(s).

In a first step, and without being limited, the desired, needed, and/or relevant, air/gas(s) entry vent(s) (4400) and air/gas exit vent(s) (4405) and/or any other orifice(s), that can cause any unwanted leaks of any air/gas(s) and/or deployed agent(s), and that connect and/or communicate with any air duct(s) (4455) and/or any other part(s), space(s), and/or component(s), that communicate with any air duct(s) (4455), are effectively sealed in a manner known to those skilled in the art, and one or more of any suitable and effective hose(s) (40)(4380) of effective length and diameter, are used to suitably and effectively connect in a manner known to those skilled in the art, the one or more of any air/gas(s) entry vent(s) (4400) to the one or more of any suitable and effective air/gas exit vent(s) (4405), and preferably and without limitation, with one or more of any various suitable vent bypass system(s) (4415), so that the various air supply duct(s) (4515) can effectively communicate with the various air return duct(s) (4520), and/or various HVAC part(s) and equipment(s) (4465) and/or HVAC unit(s) (4610), to form any effective, open system(s) (4565), sealed air/gas flow system(s) (4530), and/or air duct system(s) (4460), so that air/gas(s) and/or deployed agent(s) (4510) can be effectively flowed, moved, and/or circulated, through and/or around, these various part(s), component(s), structure(s), conduit(s), space(s), area(s), hose(s) (40) (4380), air duct(s) (4455), and/or various HVAC part(s) and equipment(s) (4465) and/or HVAC unit(s) (4610).

In a second step, and without being limited, one or more of any suitable and effective air filter(s) (4600)(4595)(4585) such as, but not limited to any, HEPA filter(s) and/or ULPA filter(s), can also be optionally located and/or used if needed and as determined by those skilled in the art, at any suitable and effective time(s), but preferably and without limitation, before, during, and/or after, and more preferably and without limitation, before, any deployed agent(s) (4510) are administered, distributed, flowed, delivered, dispersed, and/or transmitted, by one or more of any agent dispenser(s) (4505), into the one or more of any, air duct system(s) (4460), sealed air/gas flow system(s) (4530) and/or open system(s) (4565).

Without being limited, the one or more air filter(s) (4600) (4595)(4585), can be optionally located at any suitable and effective location(s), including, but not limited to, suitably and effectively sealed inside any, air duct(s) (4455), hose(s) (40)(4380), conduit(s), and/or vent bypass system(s) (4415). Without being limited, at least one air filter(s) (4600) can be effectively and suitably located either and/or both where any air/gas(s) and/or fresh air/gas(s) might enter (4595) and/or exit (4585) any, open system(s) (4565), sealed air/gas flow system(s) (4530), and/or air duct system(s) (4460), so that any air/gas(s) and/or deployed agent(s) (4510) that might enter and/or exit the connected conduit(s) system(s) (4460) and/or the one or more open system(s) (4530), can first pass through one or more of any effective entry filter(s) (4595), and then flow through various connected and/or interconnected, air duct(s) (4455), air supply duct(s) (4515), air/gas(s) entry vent(s) (4400), air/gas exit vent(s) (4405), hose(s) (40)(4380), vent bypass system(s) (4415), air return ducts (4520), HVAC part(s) and equipment(s) (4465) and/or HVAC unit(s) (4610), air duct system(s) (4460), open system(s) (4565), sealed air/gas flow system(s) (4530), and/or air duct system(s) (4460), and then optionally flow through one or more of any suitable air/gas(s) exit filter(s) (4585), and then exit into the surrounding environment (4590).

It is preferred, without limitation, that before any air/gas(s) exits into the surrounding environment (4590), the said air/gas(s) can also pass through one or more of any effective exit filter(s) (4585) that can be any suitable and effective filters such as, but not limited to any, HEPA filter(s), gas(s)/vapor(s) absorbing filter(s), and/or any gas(s)/vapor(s) capture filter(s), as known to those skilled in the art, before the air/gas(s) and/or deployed agent(s) (4510) exits the, open system(s) (4565), sealed air/gas flow system(s) (4530), and/or air duct system(s) (4460), into the surrounding environment (4590). It is more preferred, without limitation the filter(s) (4600)(4595) (4585) are at least used during the time for administering, distributing, flowing, delivering, dispersing, and/or transmitting, the deployed agent(s) (4510) and/or during any time(s) where air/gas(s) are flowed through any air duct(s) 4455) and/or HVAC part(s) and equipment(s) (4465) and/or HVAC unit(s) (4610), for drying any of the treated surfaces.

In a third step, and without being limited, various vent bypass system(s) (4415), conduit(s), and/or hose(s) (40) (4380), are effectively directly and/or indirectly interfaced with the various air/gas(s) supply duct(s) (4515) and/or air/gas(s) entry vent(s) (4400) and air/gas exit vent(s) (4405) and/or air/gas(s) return duct(s) (4520), in one or more of any area(s) and/or room(s), allowing the said air/gas(s) entry vent(s) (4400) and/or air supply duct(s) (4515) and the air/gas exit vent(s) (4405) and/or air return duct(s) (4520) to effectively communicate, where the air/gas(s) that typically flows from the one or more air/gas(s) supply ducts into various room(s) and/or area(s) (4410), instead flows through the one or more hose(s) (40)(4380) and into the one or more connected air/gas(s) exit vent(s) (4405) and/or air/gas(s) return duct(s) (4520), and preferably and without limitation, flows, circulates, moves, either through, throughout, and/or around, any, open system(s) (4565), sealed air/gas flow system(s) (4530), and/or air duct system(s) (4460), and even more preferably and without limitation, flows, circulates, and/or moves, back to and/or through, the HVAC part(s) and equipment(s) (4465) and/or HVAC unit(s) (4610).

In a fourth step, and without being limited, the one or more of any area(s), surface(s), and/or space(s), on, inside of, and/or within any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), various HVAC part(s) and equipment(s) (4465) and/or HVAC unit(s) (4610), open system(s) (4565), sealed air/gas flow system(s) (4530), and/or air duct system(s) (4460), can be mechanically cleaned by taking the step and/or undergoing the activity of "Loosening the Contamination(s)", whereby various means and methods known to those skilled in the art such as, but not limited to, mechanically scrubbing, air whipping, air washing, air brushing, hitting surface(s) with compressed air from one or more air nozzle(s), agitating, brushing, and/or wiping, the various targeted surface(s) of these various parts, space(s), and/or area(s), for one or more of any effective time(s), to remove any foreign object debris, pathogen(s), contaminant(s), and/or residue(s) that may have accumulated within, inside of, and/or on, these various part(s), component(s), structure(s), conduit(s), space(s), area(s), air duct(s) (4455), and/or various HVAC part(s) and equipment(s) (4465) and/or HVAC unit(s) (4610).

In a fifth step, and without being limited, the one or more of any area(s), surface(s), and/or space(s), on, inside of, and/or within any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), various HVAC part(s) and equipment(s) (4465) and/or HVAC unit(s) (4610), open system(s) (4565), sealed air/gas flow system(s) (4530), and/or air duct system(s) (4460), can be further cleaned by various means and methods known to those skilled in the art such as, but not limited to any, vacuuming activity, pulling a vacuum through, and/or blowing air/gas(s) through, these said various part(s), component(s), structure(s), conduit(s), space(s), hose(s) (40) (4380), area(s), air duct(s) (4455), and/or various HVAC part(s) and equipment(s) (4465) and/or HVAC unit(s) (4610), at one or more of any effective time(s) and for any suitable and effective duration of time(s), by taking the step and/or undergoing the activity of "Collecting the Contaminant(s)", whereby one or more of any suitable and effective, tool(s), apparatus(s), pressure(s), vacuum(s), air velocity(s), air speed(s), and/or volume(s), of air and/or gas(s), may be used to remove any, foreign object debris, pathogen(s), particle(s), and/or residue(s), that may have accumulated within, inside of, and/or on, these said various, part(s), component(s), structure(s), conduit(s), hose(s), space(s), area(s), air duct(s) (4455), and/or various HVAC part(s) and equipment(s) (4465) and/or HVAC unit(s) (4610), all in a manner known to those skilled in the art. Without being limited, at least the second step and the third step can also be combined in a manner known to those skilled in the art.

In a sixth step, and without being limited, one or more of any deployed agent(s) (4510) such as, but not limited to any, substance(s), agent(s), chemical(s), chemistry(s), and/or molecule(s), that includes, but is not limited to any, disinfectant(s), sterilant(s), sporicide(s), sanitizer(s), anti-fungal compound(s), anti-mold compound(s), in one or more of any suitable and effective form(s), such as, but not limited to any, gas(s), vapor(s), aerosol(s), dry aerosol(s), and/or liquid aerosol(s), can be administered, distributed, flowed, delivered, dispersed, and/or transmitted, by one or more of any agent dispenser(s) (4505), to clean, sanitize, disinfect, sterilize, and/or decontaminate, the one or more of any area(s), surface(s), and/or space(s), on and/or within any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), various HVAC part(s) and equipment(s) (4465) and/or HVAC unit(s) (4610), open system(s) (4565), sealed air/gas flow system(s) (4530), and/or air duct system(s) (4460). This is further described in the step and/or activity called "Treating the Surfaces" mentioned earlier in the present invention. It is preferred, without limitation, that this fourth step is performed after the first, second, and third steps are effectively completed.

In a seventh step, and without being limited, after the said deployed agent(s) (4510) are finished being administered, distributed, flowed, delivered, dispersed, and/or transmitted, by one or more of any agent dispenser(s) (4505), the air/gas(s) within the one or more of any, open system(s) (4565), sealed air/gas flow system(s) (4530), and/or air duct system(s) (4460), can be suitably and effectively filtered at one or more of any suitable and effective, location(s), time(s), and duration of time(s), with one or more of any suitable and effective air/gas(s) filter(s) (4600)(4595)(4585), in any suitable and effective manner known to those skilled in the art. Also, without being limited, the one or more of any air/gas(s) filter(s) (4600)(4595)(4585) can be suitably and effectively, located, located within, directly attached, indirectly attached, connected, temporarily connected, removably connected, sealed within, removably sealed within, to, with, at, and/or within, one or more of any suitable and effective location(s), part(s), component(s) and/or equipment(s), such as, but not limited to any, air duct(s) (4455), air supply duct(s) (4515), air/gas(s) entry vent(s) (4400), air/gas exit vent(s) (4405), vent bypass system(s) (4415), hose(s) (40)(4380), orifice(s), air return ducts (4520), various HVAC part(s) and equipment(s) (4465) and/or HVAC unit(s) (4610), the beginning of any air duct (4455) system, the end of any air duct (4455) system, and/or any filter(s) holding apparatus(s) (not shown), at any suitable and effective time(s). Without being limited, the one or more of any effective vapor(s) and/or gas(s) capturing and/or airborne chemical absorbing filter(s) (4600)(4595)(4585) known to those skilled in the art, can also be removably connected to the one or more of any hose(s) (40)(4380), at any effective time(s), but preferably at least after the deployed agent(s) (4510) are finished being administered, distributed, flowed, delivered, dispersed, and/or transmitted.

In an eighth step, and without being limited, after the said deployed agent(s) (4510) are finished being administered, distributed, flowed, delivered, dispersed, and/or transmitted, by one or more of any agent dispenser(s) (4505), any suitable and effective air/gas(s), and more preferably and without limitation, any, effectively filtered, fresh, and/or pure, air/gas(s) that is effectively "dry" in a manner known to those skilled in the art, can be flowed through and/or over any, space(s), area(s), part(s), conduit(s), and/or component(s), such as, but not limited to any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), various HVAC part(s) and equipment(s) (4465) and/or HVAC unit(s) (4610), open system(s) (4565), sealed air/gas flow system(s) (4530), and/or air duct system(s) (4460), to effectively dry the various treated surfaces on and/or within these said one or more of any, area(s), surface(s), part(s), conduit(s), component(s) and/or space(s). The flow of the said air/gas(s) can be provided by means such as, but not limited to, either pulling a vacuum through, and/or blowing, flowing, and/or moving, air/gas(s) through and/or over, these said area(s), surface(s), part(s), conduit(s), component(s) and/or space(s), at one or more of any effective time(s) and for any suitable and effective duration of time(s), using any suitable and effective, pressure(s), vacuum(s), air velocity(s), air speed(s), and/or volume(s), of air and/or gas(s).

With reference to FIGS. 19-21, and without limitation, an apparatus and method of another embodiment of the present invention comprises numerous steps to mechanically clean and/or treat with one or more of any deployed agent(s) (4510), the one or more of any area(s), surface(s), and/or space(s), on, inside of, and/or within any, air duct(s) (4455), air supply duct(s) (4515), HVAC part(s) and equipment(s) (4465) and/or HVAC unit(s) (4610), area(s), zone(s), area(s) of air duct(s) (4455), zone(s) of air duct(s) (4455), room(s) (4410), air/gas(s) entry vent(s) (4400), air/gas exit vent(s) (4405), hose(s) (40)(4380), vent bypass system(s) (4415), orifice(s), and/or air return ducts (4520), sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550). These one or more steps can be, without limitation, taken in any number of any suitable and effective order(s) and/or combination(s), and one or more of these steps and/or one or more of any part(s) of these steps can also be omitted and/or modified, all in a manner known to those skilled in the art. These various steps and/or activities can, and without limitation, take place at one or more of any suitable and effective location(s), and at one or more of any suitable and effective time(s) and for any suitable and effective duration(s).

In a first step, and without being limited, one or more of any relevant, desired, and/or needed, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), can be effectively isolated (Herein called "Sealed Zone(s)" (4532)) in any suitable and effective manner known to those skilled in the art, so that they cannot communicate with other, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), that are not in the same and/or designated sealed zone(s) (4532). Without being limited, the one or more of any sealed zone(s) (4532) can be created by using one or more of any suitable and effective means known to those skilled in the art, to effectively block, seal, and/or seal off, one or more of any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), in one or more of any suitable and effective location(s), area(s), and/or zone(s), in order to create one or more of any suitable and effective sealed zone(s) (4532). The one or more of any sealed zone(s) (4532) can be, and without limitation, any, size(s), shape(s), number(s), complexity(s), system(s), and/or group(s), of any part(s) and component(s) such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520).

In a second step, and without being limited, the desired, needed, and/or relevant, air/gas(s) entry vent(s) (4400) and air/gas exit vent(s) (4405), and/or any other orifice(s) that can cause any unwanted leaks of any air/gas(s) and/or deployed agent(s), and that connect with any air duct(s) (4455) and/or any other part(s), space(s), and/or component(s), that communicate with any air duct(s) (4455) and connect and/or communicate with the sealed zone(s) (4532), are effectively sealed in a manner known to those skilled in the art, and one or more of any suitable and effective hose(s) (40)(4380) of effective length and diameter, are used to suitably and effectively connect in a manner known to those skilled in the art, the one or more of any air/gas(s) entry vent(s) (4400) to the one or more of any suitable and effective air/gas exit vent(s) (4405), and preferably and without limitation, with one or more of any suitable vent bypass system(s) (4415), so that the various air supply duct(s) (4515) can effectively communicate with the various air return duct(s) (4520), to form one or more of any sealed zone(s) (4532).

Without being limited, once the sealed zone(s) (4532) are formed, air/gas(s) and/or deployed agent(s) (4510) can be effectively flowed, moved, and/or circulated, through and/or around, the various part(s), component(s), structure(s), conduit(s), space(s), and/or area(s), that can form the one or more of any sealed zone(s) (4532) such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), room(s) (4410), air shaft(s) (4472), air/gas(s) entry vent(s) (4400), air/gas exit vent(s) (4405), hose(s) (40) (4380), vent bypass system(s) (4415), orifice(s), and/or air return ducts (4520).

In a third step, and without being limited, one or more of any suitable and effective air filter(s) (4600)(4595)(4585) such as, but not limited to any, HEPA filter(s) and/or ULPA filter(s), can also be located and/or used at any suitable and effective time(s), but preferably and without limitation, before, during, and/or after, any deployed agent(s) (4510) are administered, distributed, flowed, delivered, dispersed, and/or transmitted, by one or more of any agent dispenser(s) (4505), into the one or more of any, sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), and more preferably, and without limitation, after the deployed agent(s) (4510) are administered, distributed, flowed, delivered, dispersed, and/or transmitted.

Without being limited, the one or more air filter(s) (4600) (4595)(4585), can be optionally located at any suitable and effective location(s), including, but not limited to, suitably and effectively sealed inside any, air duct(s) (4455), hose(s) (40)(4380), and/or vent bypass system(s) (4415). It is preferred, without limitation, that at least one air filter(s) (4600) can be effectively and suitably located either and/or both where any air/gas(s) and/or fresh air/gas(s) enters (4595) and exits (4585) the sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), so that any air/gas(s) and/or deployed agent(s) (4510) that enters and/or exits the one or more sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), can first pass through one or more of any effective entry filter(s) (4595), and then flow through various connected and/or interconnected, air duct(s) (4455), air supply duct(s) (4515), air/gas(s) entry vent(s) (4400), air/gas exit vent(s) (4405), hose(s) (40)(4380), vent bypass system(s) (4415), air return ducts (4520), HVAC part(s) and equipment(s) (4465) and/or HVAC unit(s) (4610), sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), and then flow through one or more air/gas(s) exit filter(s) (4585), and then exit into the surrounding environment (4590). It is preferred, without limitation, that before any air/gas(s) exits into the surrounding environment (4590), the said air/gas(s) can also pass through one or more of any effective exit filter(s) (4585) that can be any suitable and effective filters such as, but not limited to any, HEPA filter(s) gas(s)/vapor(s) absorbing filter(s), and/or any gas(s)/vapor(s) capture filter(s), as known to those skilled in the art, before the air/gas(s) and/or deployed agent(s) (4510) exits the sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), and into the surrounding environment (4590). It is more preferred, without limitation, that the said filter(s) (4600)(4595) (4585) are at least used during the time for administering, distributing, flowing, delivering, dispersing, and/or transmitting, the deployed agent(s) (4510) into any, sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), and/or during any time(s) where air/gas(s) are flowed through any air duct(s) (4455) and/or HVAC part(s) and equipment(s) (4465) and/or HVAC unit(s) (4610), for drying any of these treated surfaces.

In a fourth step, and without being limited, various vent bypass system(s) (4415), conduit(s), and/or hose(s) (40)(4380), are effectively directly and/or indirectly interfaced with the various air/gas(s) supply duct(s) (4515) and/or air/gas(s) entry vent(s) (4400) and air/gas exit vent(s) (4405) and/or air/gas(s) return duct(s) (4520), in one or more of any area(s) and/or room(s), allowing the said air/gas(s) entry vent(s) (4400) and/or air supply duct(s) (4515) and the air/gas exit vent(s) (4405) and/or air return duct(s) (4520) to effectively communicate, where the air/gas(s) that typically flows from the one or more air/gas(s) supply ducts into various room(s) and/or area(s) (4410), instead flows through the one or more hose(s) (40)(4380) and into the one or more connected air/gas(s) exit vent(s) (4405) and/or air/gas(s) return duct(s) (4520), and preferably and without limitation, flows, circulates, and/or moves, either through, throughout, and/or around, any, sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550).

In a fifth step, and without being limited, the one or more of any area(s), surface(s), and/or space(s), on, inside of, and/or within any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), various HVAC part(s) and equipment(s) (4465) and/or HVAC unit(s) (4610), sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), can be mechanically cleaned by various means and methods known to those skilled in the art such as, but not limited to, mechanically scrubbing, air whipping, air washing, air brushing, hitting surface(s) with compressed air from one or more air nozzle(s), agitating, brushing, and/or wiping, the various targeted surface(s) of these various parts, space(s), and/or area(s), for one or more of any effective time(s), to remove any foreign object debris, pathogen(s), contaminant(s), and/or residue(s) that may have accumulated within, inside of, and/or on, these various part(s), component(s), structure(s), conduit(s), space(s), area(s), air duct(s) (4455), and/or various HVAC part(s) and equipment(s) (4465) and/or HVAC unit(s) (4610).

In a sixth step, and without being limited, the one or more of any area(s), surface(s), and/or space(s), on, inside of, and/or within any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), and various HVAC part(s) and equipment(s) (4465) and/or HVAC unit(s) (4610), sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), can then be further cleaned by various means and methods known to those skilled in the art such as, but not limited to any, vacuuming activity, pulling a vacuum through, and/or blowing air/gas(s) through, these various part(s), component(s), structure(s), conduit(s), space(s), hose(s) (40)(4380), area(s), air duct(s) (4455), and/or various HVAC part(s) and equipment(s) (4465) and/or HVAC unit(s) (4610), at one or more of any effective time(s) and for any suitable and effective duration of time(s), and with one or more of any suitable and effective, tool(s), apparatus(s), pressure(s), vacuum(s), air velocity(s), air speed(s), and/or volume(s) of air and/or gas(s), to remove any foreign object debris, pathogen(s), particle(s), and/or residue(s), that may have accumulated within, inside of, and/or on, these various part(s), component(s), structure(s), conduit(s), hose(s), space(s), area(s), air duct(s) (4455), and/or various HVAC part(s) and equipment(s) (4465) and/or HVAC unit(s) (4610), in a manner known to those skilled in the art. Without being limited, at least the second step and the third step can also be combined in a manner known to those skilled in the art.

In a seventh step, and without being limited, one or more of any deployed agent(s) (4510) such as, but not limited to any, substance(s), agent(s), chemical(s), chemistry(s), and/or molecule(s), that includes, but is not limited to any, disinfectant(s), sterilant(s), sporicide(s), sanitizer(s), anti-fungal compound(s), anti-mold compound(s), in one or more of any suitable and effective form(s), such as, but not limited to any, gas(s), vapor(s), aerosol(s), dry aerosol(s), and/or liquid aerosol(s), can be administered, distributed, flowed, delivered, dispersed, and/or transmitted, by one or more of any agent dispenser(s) (4505), to clean, sanitize, disinfect, sterilize, and/or decontaminate, the one or more of any area(s), surface(s), and/or space(s), on and/or within any, air duct(s) (4455), air supply duct(s) (4515), air/gas(s) entry vent(s) (4400), air/gas exit vent(s) (4405), hose(s) (40) (4380), vent bypass system(s) (4415), orifice(s), air return ducts (4520), various HVAC part(s) and equipment(s) (4465) and/or HVAC unit(s) (4610), sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550). It is preferred, without limitation, that this fourth step is performed after the first, second, and third steps are effectively completed.

In an eighth step, and without being limited, after the said deployed agent(s) (4510) are finished being administered, distributed, flowed, delivered, dispersed, and/or transmitted, by one or more of any agent dispenser(s) (4505), the air/gas(s) within the one or more of any, sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), can be suitably and effectively filtered at one or more of any suitable and effective, time(s), location(s), and duration of time(s), with one or more of any suitable and effective air/gas(s) filter(s) (4600)(4595)(4585), in any suitable and effective manner known to those skilled in the art. Also, without being limited, the one or more of any air/gas(s) filter(s) (4600)(4595)(4585) can be suitably and effectively, located, located within, directly attached, indirectly attached, connected, temporarily connected, removably connected, sealed within, removably sealed within, to, with, at, and/or within, one or more of any suitable and effective location(s), part(s), component(s) and/or equipment(s) such as, but not limited to any, air duct(s) (4455), air supply duct(s) (4515), air/gas(s) entry vent(s) (4400), air/gas exit vent(s) (4405), vent bypass system(s) (4415), hose(s) (40)(4380), orifice(s), air return ducts (4520), and various HVAC part(s) and equipment(s) (4465) and/or HVAC unit(s) (4610), including but not limited to any filter(s) holding apparatus(s) (not shown). Without being limited, the one or more of any effective vapor and/or gas(s) capturing and/or airborne chemical absorbing filter(s) (4600)(4595)(4585) known to those skilled in the art, can also be removably connected to the one or more of any hose(s) (40)(4380), after the deployed agent(s) (4510) are finished being administered, distributed, flowed, delivered, dispersed, and/or transmitted.

In a ninth step, and without being limited, after the said deployed agent(s) (4510) are finished being administered, distributed, flowed, delivered, dispersed, and/or transmitted, by one or more of any agent dispenser(s) (4505), any suitable and effective air/gas(s), and more preferably and without limitation, any, effectively filtered, fresh, and/or pure, air/gas(s) that is effectively "dry" in a manner known to those skilled in the art, can be flowed through and/or over any, space(s), area(s), part(s), conduit(s), and/or component(s), such as, but not limited to any, air duct(s) (4455), air supply duct(s) (4515), air/gas(s) entry vent(s) (4400), air/gas exit vent(s) (4405), hose(s) (40)(4380), vent bypass system(s) (4415), orifice(s), air return ducts (4520), various HVAC part(s) and equipment(s) (4465) and/or HVAC unit(s) (4610), sealed zone(s) (4532), sealed air/gas flow system(s) (4530), air duct(s) system(s) (4460), isolated zone(s) (4540), and/or isolated targeted zone(s) of HVAC part(s) and equipment(s) (4465) and air duct(s) (4550), to effectively dry the various treated surfaces on and/or within these said one or more of any, area(s), part(s), conduit(s), component(s) and/or space(s). The flow of the said air/gas(s) can be provided by means such as, but not limited to, either pulling a vacuum through, and/or blowing, flowing, and/or moving air/gas(s) through and/or over, these said area(s), part(s), conduit(s), component(s) and/or space(s), at one or more of any effective time(s) and for any suitable and effective duration of time(s), using any suitable and effective, pressure(s), vacuum(s), air velocity(s), air speed(s), and/or volume(s), of air and/or gas(s).

Figure 22:
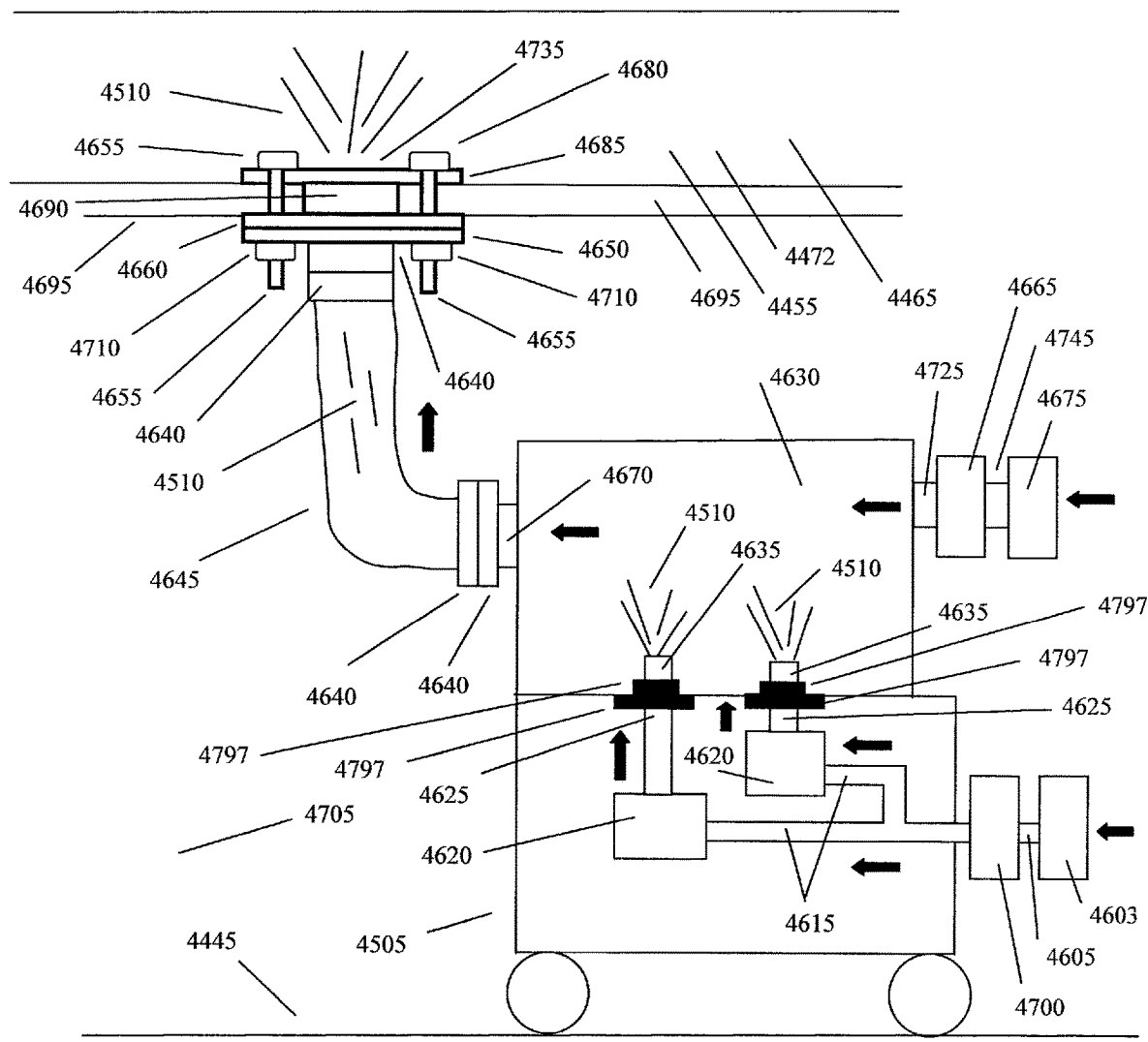
FIG. 22 is a schematic diagram of an enhanced deployed agent generator that includes at least one aerosol, gas, and/or vapor collection chamber which is connected to and communicates with at least one blower, fan, and/or air pump.
Figure 24:
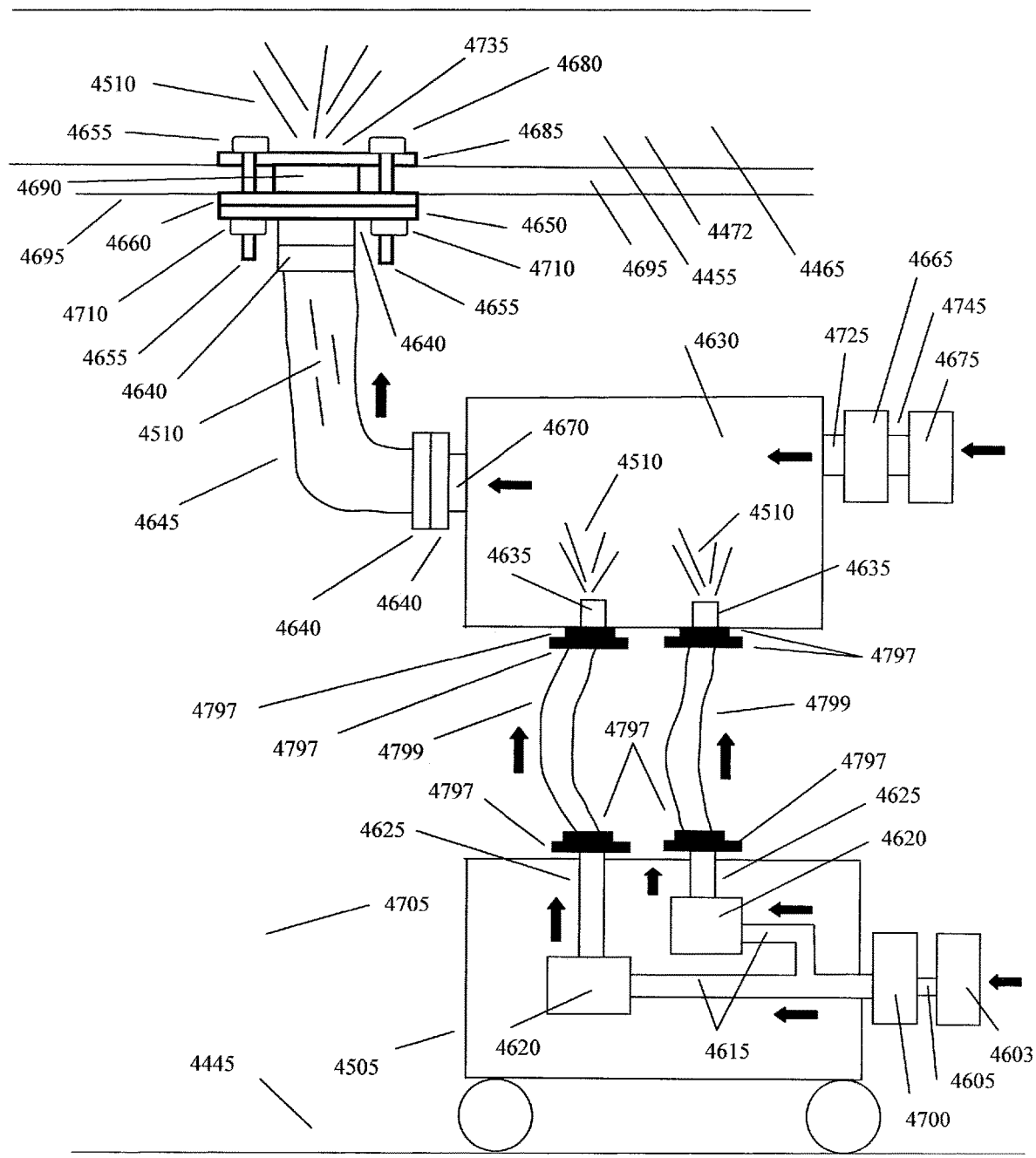
FIG. 24 is a schematic diagram of an enhanced deployed agent(s) generator that includes at least one aerosol, gas, and/or vapor collection chamber which is connected to and communicates with at least one blower, fan, and/or air pump, and where the collection chamber can directly and/or indirectly removably communicate with various conduit(s), HVAC equipment, air shaft, and/or air duct to flow the generated aerosol, gas, and/or vapor into enclosure(s), space(s), location(s), and/or area(s).

With reference to FIGS. 22 and 24, and according to another embodiment, and without limitation, many agent dispenser(s) (4505) known to those skilled in the art, cannot provide and/or output one or more of any effective airflow(s) that can carry the deployed agent(s) (4510) various effective and/or needed distance(s), and/or the airflow that the said agent dispenser(s) (4505) can generate and/or provide does not have effective attributes such as, but not limited to any effective, air/gas flow output speed, and/or air/gas flow volume output per unit of time, to effectively carry the deployed agent(s) (4510), through various part(s), component(s), structure(s), conduit(s), enclosure(s), space(s), and/or area(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), air return ducts (4520), air duct system(s) (4460), sealed zone(s) (4532), sealed air/gas flow system(s) (4530), and/or open system(s) (4565), especially and without limitation, when these various part(s), component(s), structure(s), conduit(s), enclosure(s), space(s), and/or area(s), have one or more of any, long, horizontal, complex, geometrically complex, and/or vertical, runs of conduit(s) and/or air duct(s) (4455). Also, with reference to FIGS. 22 and 24, and without limitation, agent dispenser(s) (4505) known to those skilled in the art, need one or more effective means to suitably and/or effectively interface with various, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), room(s) (4410), air shaft(s) (4472), air/gas(s) entry vent(s) (4400), air/gas exit vent(s) (4405), hose(s) (40)(4380), vent bypass system(s) (4415), orifice(s), service and/or work compartment(s) (not shown), and/or air return ducts (4520), especially in a manner that is hermetically sealed. The present invention provides a means to solve these said problems with the current art.

According to FIGS. 22 and 24, and without limitation, an apparatus and method is presented in the present invention. Without being limited, one or more of any agent dispenser(s) (4505) known to those skilled in the art, can be effectively communicated with and/or connected to one or more of any suitable and effective location(s) of the one or more of any agent flow compartment(s) (4630). Further, and without limitation, the deployed agent(s) (4510) can be aerosolized, vaporized, generated, and/or created, at any suitable and effective location(s) outside of the said agent flow compartment(s) (4630) by one or more of any suitable and effective means to aerosolize, generate, vaporize, translate, and/or create, the deployed agent(s) (4510) that is know to those skilled in the art (Herein called "Deployed Agent Generator(s)") (4620) such as, but not limited to any, ultrasonic aerosol generator(s), aerosol generator(s), gas(s) and/or vapor(s) generator(s), hydrogen peroxide gas(s)/vapor(s) generator(s), peroxyacetic acid (PAA) gas(s)/vapor(s) generator(s), ozone generator(s), chlorine dioxide gas(s)/vapor(s) generator(s), aerosol(s) containing chlorine dioxide generator(s), aerosol generator(s) that disperse any chemical(s) and/or molecules that are effective at killing and/or neutralizing any bacteria(s), viruse(s), spore(s), bacteriophage(s), and/or fungus(s), and/or aerosol generator(s) that generates aerosol using any compressed air.

Without being limited, the one or more deployed agent generator(s) (4620) can directly and/or indirectly connect and communicate with the one or more agent flow compartment(s) (4630) using one or more of any suitable and effective pipe(s), conduit(s), duct(s), and/or hose(s) (Herein called "Deployed Agent Exhaust Pipe(s)") (4625). Without being limited, the deployed agent exhaust pipe(s) (4625) can also include and/or be replaced by, one or more of any suitable and effective aerosol extractor apparatus(s), and even more specifically one or more of any exhaust stack(s) and/or output conduit(s) or pipe(s) that are a part of the one or more of any aerosol extractor apparatus(s), as taught in U.S. Pat. No. 9,789,508 to Baumgartner et al. Also, and without being limited, the deployed agent exhaust pipe(s) (4625) can removably connect to the agent flow compartment(s) (4630) using one or more of any suitable and effective means known to those skilled in the art such as, but not limited to any, Tri-clamp adapter(s), and/or hose coupling(s) (Herein called "Coupling(s)") (4797). The deployed agent exhaust pipe(s) (4625) can be, and without limitation, any suitable and effective, length(s), flexibility(s), width(s), height(s), and/or diameter(s), and they can be constructed from one or more of any suitable and effective material(s) known to those skilled in the art. It is preferred, without limitation, that the one or more deployed agent exhaust pipe(s) (4625) at least, terminate with, terminate into, terminate inside of, connect with, connect inside of, connect outside of, and/or communicate with, the agent flow compartment(s) (4630) in or with any suitable and effective manner, and at any suitable and effective location(s), so that the deployed agent(s) (4510) can be effectively moved, circulated, flowed, and/or blown, into the said agent flow compartment(s) (4630) from the deployed agent generator(s)" (4620). Also, and without being limited, the deployed agent generator(s) (4620) can be located at any suitable and effective location(s) such as, but not limited to, outside of the agent flow compartment(s) (4630), inside of the agent flow compartment(s) (4630), and/or partially inside of the agent flow compartment(s) (4630). It is preferred, without limitation, that the deployed agent generator(s) (4620) are suitably located outside of the agent flow compartment(s) (4630) and suitably inside of the agent dispenser(s) (4505).

The deployed agent(s) (4510) can be, and without limitation, moved, circulated, flowed, and/or blown, from the deployed agent generator(s) (4620) into the agent flow compartment(s) (4630) using any suitable and effective means known to those skilled in the art such as, but not limited to one or more of any, suitable and effective source(s) of pressurized air/gas(s), air pump(s), blower(s), fan(s), and/or any other means to move any air/gas(s), (Herein called "Agent Generator Blower(s)") (4700) and at any suitable and effective, air/gas flow output speed(s), and/or air/gas flow volume output(s) per unit of time, to effectively carry the deployed agent(s), from the deployed agent generator(s) (4620) into the agent flow compartment(s) (4630). Any suitable and effective amount of deployed agent(s) (4510) can be moved into the agent flow compartment(s) (4630) from the deployed agent generator(s) (4620) per any suitable and effective unit of time. It is preferred, without limitation, that the deployed agent generator(s) (4620) are effectively connected to and communicate with one or more of any suitable and effective agent generator blower(s) (4700). Without being limited, the agent generator blower(s) (4700) can be effectively directly and/or indirectly connected to and communicate with one or more of any suitable and effective means to filter the air/gas(s) before and/or after they enter and/or leave the agent generator blower(s) (4700), such as, but not limited to any, HEPA filter(s) (Herein called "Airflow Injection Filter(s)") (4603).

The said agent generator blower(s) (4700) can be, and without limitation, effectively directly and/or indirectly connected and/or removably connected to, and communicate with, one or more of any suitable and effective filter(s) (4603) or airflow injection filter(s) (4603), all in a manner known to those skilled in the art. It is preferred, without limitation, that air/gas(s) first enters the said one or more agent generator blower(s) (4700) before passing through the one or more airflow injection filter(s) (4603). However, and without limitation, air/gas(s) can also enter the agent generator blower(s) (4700) after passing through the one or more airflow injection filter(s) (4603).

Referring to FIGS. 22 and 24, and without being limited, the one or more agent flow compartment(s) (4630) can also be located in one or more of any suitable and effective location(s) including, but not limited to, inside the agent dispenser(s) (4505), partially inside the agent dispenser(s) (4505), outside of and remote from the agent dispenser(s) (4505), and/or outside of the agent dispenser(s) (4505). It is preferred, without limitation, that the one or more agent flow compartment(s) (4630) are located suitably and effectively outside of the agent dispenser(s) (4505), but at least suitably and effectively attached and/or connected to the one or more agent dispenser(s) (4505) with which they communicate with. It is also preferred, without limitation, that the one or more agent flow compartment(s) (4630) are removably and suitably connected and/or attached to the one or more agent dispenser(s) (4505) with which they communicate with.

Referring to FIG. 24, and without limitation, the one or more agent flow compartment(s) (4630) can be located at one or more of any suitable and effective distance(s) from the one or more agent dispenser(s) (4505) and/or deployed agent generator(s) (4620). Without being limited, the at least one deployed agent generator(s) (4620) and/or deployed agent exhaust pipe(s) (4625) can removably connect to the agent flow compartment(s) (4630) using one or more of any suitable and effective chamber connection conduit(s) (4799). Without being limited, any suitable and effective means known to those skilled in the art can suitably and effectively removably connect the said chamber connection conduit(s) (4799) to the deployed agent generator(s) (4620) and/or deployed agent exhaust pipe(s) (4625), and the agent flow compartment(s) (4630), so that the one or more deployed agent generator(s) (4620) can effectively communicate with the one or more agent flow compartment(s) (4630).

Also, and without being limited, the chamber connection conduit(s) (4799) can removably connect to the deployed agent generator(s) (4620), deployed agent exhaust pipe(s) (4625), and/or the agent flow compartment(s) (4630), using one or more of any suitable and effective means known to those skilled in the art such as, but not limited to any, Tri-clamp adapter(s), hose coupling(s), and/or any other suitable coupling(s) (4797) and related part(s) and component(s). The chamber connection conduit(s) (4799) can be, and without limitation, any suitable and effective, length(s), flexibility(s), width(s), height(s), design(s), and/or diameter(s), and they can be constructed from one or more of any suitable and effective material(s) known to those skilled in the art.

Without being limited, the deployed agent(s) (4510) can be, and without limitation, moved, circulated, flowed, and/or blown, from the agent flow compartment(s) (4630) and into any, location(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), using any suitable and effective means known to those skilled in the art such as, but not limited to one or more of any, suitable and effective source(s) of pressurized air/gas(s), air pump(s), blower(s), fan(s), and/or any means to move any air/gas(s), (Herein called "Compartment Blower(s)") (4665) and at any suitable and effective, speed(s), air/gas(s) flow output speed(s), and/or air/gas(s) flow volume output(s) per unit of time, to effectively carry the deployed agent(s), out from the agent flow compartment(s) (4630). Any suitable and effective amount of deployed agent(s) (4510) can be moved out of the agent flow compartment(s) (4630) per any suitable and effective unit of time. It is preferred, without limitation, that the agent flow compartment(s) (4630) are connected to and communicate with one or more of any suitable and effective compartment blower(s) (4665). Without being limited, the compartment blower(s) (4665) can be connected to and communicate with one or more of any suitable and effective means to filter the air/gas(s) before they enter the agent flow compartment(s) (4630) such as, but not limited to any, HEPA filter(s) (Herein called "Compartment Airflow Filter(s)") (4675). Without being limited, the agent flow compartment(s) (4630) can also be be connected to and communicate with one or more of any suitable and effective compartment airflow filter(s) (4675) to filter any air/gas(s) before they enter the agent flow compartment(s) (4630) after leaving the said compartment blower(s) (4665). It is preferred, without limitation, that any air/gas(s) that leave the one or more compartment blower(s) (4665) are at least effectively filtered by at least one compartment airflow filter(s) (4675), located in one or more of any suitable and effective location(s), before the said air/gas(s) enters the said agent flow compartment(s) (4630).

The agent flow compartment(s) (4630) can be, without limitation, directly and/or indirectly connected to and communicate with one or more of any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), using one or more of any suitable and effective means known to those skilled in the art. Without being limited, the agent flow compartment(s) (4630) can removably connect and communicate with and/or have, one or more of any suitable and effective outlet(s) (Herein called "Agent Outlet(s)") (4670) through which the deployed agent(s) (4510) can flow, move, and/or be blown through, and out of the agent flow compartment(s) (4630).

It is preferred, without limitation, that the one or more agent outlet(s) (4670) and/or agent flow compartment(s) (4630), can connect and communicate with the said location(s), room(s), enclosure(s), space(s), part(s), component(s), structure(s), and/or conduit(s), with one or more of any suitable and effective, hose(s), pipe(s), and/or conduit(s) (Herein called "Connection Conduit(s)") (4645). Without being limited, the connection conduit(s) can be any suitable and effective, length(s), width(s), flexibility(s), height(s), and/or diameter(s), and they can be constructed from one or more of any suitable and effective material(s) known to those skilled in the art. Also, and without being limited, the one or more agent flow compartment(s) (4630) and/or agent outlet(s) (4670) can removably connect with and communicate with one or more of any suitable and effective connection conduit(s) (4645) using one or more of any suitable and effective means known to those skilled in the art such as, but not limited to any, Tri-clamp adapter(s), and/or hose coupling(s). It is preferred, without limitation, that the agent flow compartment(s) (4630) is directly and/or indirectly connected to and effectively communicates with one or more of any suitable and effective hose connector(s) (4640), and it is more preferred, without limitation, that the agent flow compartment(s) (4630) is directly and/or indirectly connected to and effectively communicates with one or more of any suitable and effective agent outlet(s) (4670) that can suitably and effectively connect with one or more hose connector(s) (4640), all in a manner known to those skilled in the art.

Also, without being limited, the connection conduit(s) (4645) can connect and communicate with the said any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), chamber(s) (not shown), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), using one or more of any suitable and effective means known to those skilled in the art such as, but not limited to any, bulkhead fitting(s), and/or air/gas(s) pass-through fitting(s), that can be any suitable and effective, size(s), shape(s), geometry(s), length(s), width(s), design(s), and/or height(s), and can be removably attached at one or more of any suitable and effective location(s) (Herein called "Airflow Bulkhead Fitting(s)") (4680). Without being limited, the airflow bulkhead fitting(s) (4680) can be any suitable and effective, design(s), size(s), shape(s), geometry(s), diameter(s), length(s), width(s), and/or height(s), and can be any suitable and effective airflow bulkhead fitting(s) (4680) design(s) known to those skilled in the art. Without limitation, the said bulkhead fitting(s) (4680) can be designed and built so that they have one or more of any suitable and effective hole(s) and/or orifice(s) (not shown), that are any suitable and effective, size(s), shape(s), geometry(s), length(s), width(s), design(s), thickness(s), and/or height(s), but at least effectively sized and designed to allow any effective flow(s) of air/gas(s) and/or deployed agent(s) (4510) to flow from the one or more of any connection conduit(s) (4645) and into and through the one or more airflow bulkhead fitting(s) (4680), and into the said any, location(s), room(s), enclosure(s), space(s), part(s), component(s), structure(s), and/or conduit(s). Further, and without limitation, at least one side(s), halve(s), and/or part(s), of the bulkhead fitting(s) (4680), and as known to those skilled in the art, can removably connect with and communicate with one or more of any suitable and effective connection conduit(s) (4645) using one or more of any suitable and effective means known to those skilled in the art such as, but not limited to any suitable, Tri-clamp adapter(s), and/or hose coupling(s) (Herein called "Hose Connector(s)") (4640).

Also, and without being limited, one or more of any suitable and effective seal(s) and/or gasket(s) (Herein called "Gasket(s)") (4660) can be located at one or more of any suitable and effective location(s) between any suitable and effective part(s) of any airflow bulkhead fitting(s) (4680) and any suitable and effective parts of any wall(s) (4695). It is preferred, without limitation, that the said gasket(s) (4660) are included in the design of the said bulkhead fitting(s) (4680) and/or are a part of the design of the bulkhead fitting(s) (4680). Without limitation, the said gasket(s) (4660) can be designed and built so that they have one or more of any suitable and effective hole(s) and/or orifice(s) (not shown), that are any suitable and effective, size(s), shape(s), geometry(s), length(s), width(s), design(s), thickness(s), and/or height(s), but at least effectively sized and designed to allow any effective flow(s) of any air/gas(s) and/or deployed agent(s) (4510) to flow from the one or more of any connection conduit(s) (4645), through the one or more airflow bulkhead fitting(s) (4680), through the said gasket(s) (4660), and into the said one or more of any, location(s), room(s), enclosure(s), space(s), part(s), component(s), structure(s), and/or conduit(s). It is preferred, without limitation, that the one or more said hole(s) and/or orifice(s) (not shown) are located in and/or about the middle of the said gasket(s) (4660). It is also preferred, without limitation, that at least one of the said gasket(s) (4660) is located between one suitable part of any bulkhead fitting(s) (4680) known to those skilled in the art and one side of any wall(s) (4695), and another at least one of the said gasket(s) (4660) is located between another suitable part of any bulkhead fitting(s) (4680) known to those skilled in the art, and the other side of any wall(s) (4695), all in a manner known to those skilled in the art.

Without being limited, the deployed agent(s) (4510) can flow from at least the one or more agent flow compartment(s) (4630), preferably and without limitation through the one or more agent outlet(s) (4670), and then through the one or more connection conduit(s) (4645), where the deployed agent(s) (4510) can then flow through the one or more airflow bulkhead fitting(s) (4680) and any associated part(s), component(s), and gasket(s) (4660), including flowing through the one or more wall hole(s) (4690) and through the one or more hole(s)s and/or orifice(s) in the rear fitting plate(s) (Herein called "Rear Fitting Plate Orifice(s)") (4735), and into the said one or more of any, location(s), room(s), enclosure(s), space(s), part(s), component(s), structure(s), and/or conduit(s). Without being limited, the one or more wall hole(s) (4690) and rear fitting plate orifice(s) (4735) can be any suitable and effective, number(s), size(s), shape(s), diameter(s), length(s), width(s), thickness(s), and/or design(s).

Without being limited, one or more of any suitable and effective, hole(s), opening(s), and/or orifice(s) (Herein called "Wall Hole(s)") (4690), of any suitable and effective, design(s), size(s), shape(s), geometry(s), diameter(s), length(s), width(s), and/or height(s), can exist, can be made, can be penetrated through, and/or can be created in, on, and/or through, one or more of any, wall(s), barrier(s), structure(s), part(s), component(s), bulkhead wall(s), and/or partition(s) (Herein called "Wall(s)") (4695), of and/or belonging to, one or more of any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520). Without being limited, the one or more of any airflow bulkhead fitting(s) (4680) can suitably and effectively, interface with, interact with, communicate with, cover, partially cover, fully cover, cover and communicate with, and/or connect with, the one or more of any wall hole(s) (4690). Also, and without limited, the one or more wall hole(s) (4690) can, and without limitation, create one or more effective path(s) for any air/gas(s) and/or deployed agent(s) (4510) to flow from the one or more connection conduit(s) (4645), through the one or more airflow bulkhead fitting(s) (4680) and wall hole(s) (4690), and into the said one or more of any, location(s), room(s), enclosure(s), space(s), part(s), component(s), structure(s), and/or conduit(s).

Referring to FIGS. 22 and 24, and without limitation, a more detailed description of an apparatus and method of the present invention is given. Without being limited, an improved agent dispenser(s) (4505) includes at least one agent flow compartment(s) (4630) that can be removably interfaced with, remotely connected to, be a part of, and/or be attached to, the said agent dispenser(s) (4505). The deployed agent(s) (4510) are generated in at least one deployed agent generator(s) (4620). Without being limited, the said deployed agent(s) (4510) can be flowed and/or moved out of the said deployed agent generator(s) (4620) and through one or more of any suitable and effective deployed agent exhaust pipe(s) (4625). Also without being limited, the said one or more deployed agent generator(s) (4620) and/or deployed agent exhaust pipe(s) (4625) can directly and/or indirectly communicate with the said agent flow compartment(s) (4630), where the said deployed agent(s) (4510) can preferably, and without limitation, flow and/or move into the said agent flow compartment(s) (4630) through and/or out of one or more of any suitable and effective flow outlet(s) (4635) that preferably, and without limitation, effectively communicates with and/or is directly and/or indirectly connected to, and/or is a part of, the said exhaust pipe(s) (4625). It is preferred, without limitation, that the one or more flow outlet(s) (4635) are suitably and effectively located inside of the agent flow compartment(s) (4630). Without being limited, the said exhaust pipe(s) (4625) can also terminate with one or more of the said flow outlet(s) (4635).

Alternatively, and without limitation, the one or more flow outlet(s) (4635) can connect and/or removably connect with one or more of any suitable and effective, Tri-clamp adapter(s), hose coupling(s), and/or any other suitable coupling(s) (4797) and related part(s) and component(s), all in a manner known to those skilled in the art. For example, and without limitation, the one or more flow outlet(s) (4635) can also extend any suitable and effective distance(s) outside of and/or beyond the agent flow compartment(s) (4630) and effectively connect and communicate with one or more suitable coupling(s) (4797), and the one or more output end(s) of the one or more deployed agent exhaust pipe(s) (4625) and/or deployed agent generator(s) (4620), can also effectively connect and communicate with one or more suitable coupling(s) (4797), so that one or more of any suitable chamber connection conduit(s) (4799) can removably connect with the input end of the said flow outlet(s) (4635) and the output end of the said deployed agent exhaust pipe(s) (4625) and/or deployed agent generator(s) (4620), and provide a means for the deployed agent generator(s) (4620) to effectively communicate with the agent flow compartment(s) (4630). Without being limited, the said flow outlet(s) (4635) can be any suitable and effective, size(s), shape(s), diameter(s), design(s), height(s), length(s), width(s), and/or number(s).

One or more of any suitable and effective blower(s), fan(s), air pump(s), or otherwise agent generator blower(s) (4700), can and without limitation, provide an effective flow(s) of air/gas(s) to effectively move, circulate, and/or flow, the deployed agent(s) (4510) out of the one or more deployed agent generator(s) (4620) and into the one or more agent flow compartment(s) (4630). The agent generator blower(s) (4700) can be, and without limitation, effectively and removably connected directly and/or indirectly to one or more of any effective filter(s) (4603) or air flow injection filter(s) (4603), all in a manner known to those skilled in the art. Air/gas(s), preferably and without limitation, from the environment surrounding the agent dispenser(s) (4505), can and without limitation, enter the said agent generator blower(s) (4700) after passing through one or more suitable conduit(s) or air flow inlet pipe(s) (4605) and before and/or after exiting the said air flow injection filter(s) (4603). The said fresh air/gas(s) leaves the said agent generator blower(s) (4700) and travels through one or more of any suitable conduit(s) or air flow supply pipe(s) (4615), where the said fresh air/gas(s) enters the one or more deployed agent generator(s) (4620). Without being limited, the one or more deployed agent(s) (4510) are created, formed, generated, vaporized, aerosolized, and/or turned into any gas(s) and/or vapor(s), inside of and/or by, the one or more deployed agent generator(s) (4620), all in a manner known to those skilled in the art. The said fresh air/gas(s) that is supplied to and/or into the deployed agent generator(s) (4620), flows, pushes, blows, moves, and/or circulates, the deployed agent(s) (4510) out of the said deployed agent generator(s) (4620) and into one or more suitable conduit(s) or deployed agent exhaust pipe(s) (4625). The said one or more deployed agent exhaust pipe(s) (4625) effectively communicates with one or more agent flow compartment(s) (4630) so that the said deployed agent(s) (4510) can effectively flow, move, and/or circulate, from the said deployed agent generator(s) (4620) and into the said agent flow compartment(s) (4630).

Without being limited, the agent flow compartment(s) (4630) can be any suitable and effective, size(s), shape(s), number(s), length(s), width(s), height(s), design(s), and/or geometry(s), and can include various design enhancements for effective airflow and/or draining of any fluids, all in a manner known to those skilled in the art. Also, and without being limited, the agent flow compartment(s) (4630) can have one or more of any suitable and effective, outlet(s), exit orifice(s), exit(s), exhaust outlet(s), exhaust conduit(s), and/or hole(s) (Herein called "Agent Outlet(s)") (4670), through which air/gas(s) and the deployed agent(s) (4510) can exit the agent flow compartment(s) (4630). The agent outlet(s) (4670) can be any suitable and effective, size(s), shape(s), number(s), length(s), protrusion length(s), diameter(s), width(s), height(s), design(s), and/or geometry(s). Without being limited, the deployed agent(s) (4510) can flow from the one or more agent flow compartment(s) (4630), through the one or more agent outlet(s) (4670), and then into and through the one or more connection conduit(s) (4645). Without being limited, the deployed agent(s) (4510) can also flow from the one or more agent flow compartment(s) (4630), through the one or more agent outlet(s) (4670), and into the environment that surrounds the agent dispenser(s) (4505) and/or agent flow compartment(s) (4630). Alternatively, and without limitation, the deployed agent(s) (4510) can also flow from the one or more agent flow compartment(s) (4630), through the one or more agent outlet(s) (4670), through the one or more connection conduit(s) (4645), and then exit the said connection conduit(s) (4645) into the environment (4705) that surrounds the agent dispenser(s) (4505) and/or agent flow compartment(s) (4630).

Without being limited, the said agent outlet(s) (4670) can directly and/or indirectly connect with one or more of any suitable and effective means, known to those skilled in the art, to suitably and effectively connect and/or removably connect, with one or more of any of the said connection conduit(s) (4645). It is preferred, without limitation, that the one or more agent flow compartment(s) (4630) have and/or communicate with one or more of any suitable and effective agent outlet(s) (4670) that suitably and effectively connects and communicates with one or more of the said hose connector(s) (4640), and the said hose connector(s) (4640) connects and communicates with one or more of the said connection conduit(s) (4645). It is also preferred, without limitation, that the said hose connector(s) (4640) are any suitable Tri-clamp adapter(s) and Tri-clamp connector(s) known to those skilled in the art.

One or more of any suitable and effective blower(s), fan(s), air pump(s), or otherwise compartment blower(s) (4665) can be, and without limitation, effectively and removably connected to the agent flow compartment(s) (4630). The said compartment blower(s) (4665) provides an effective flow of air/gas(s) into the one or more agent flow compartment(s) (4630) to effectively move, circulate, and/or flow, the deployed agent(s) (4510), that are flowed, moved, and/or circulated, into the said agent flow compartment(s) (4630) from the said deployed agent generator(s) (4620), out of the said agent flow compartment(s) (4630) and into the one or more connection conduit(s) (4645) and/or surrounding environment(s) (4705). The said compartment blower(s) (4665) can be, and without limitation, effectively directly and/or indirectly connected and/or removably connected to, and communicate with, one or more of any suitable and effective filter(s) (4675) or compartment air flow filter(s) (4675), all in a manner known to those skilled in the art. It is preferred, without limitation, that air/gas(s) first enters the said one or more compartment blower(s) (4665) before passing through the one or more compartment air flow filter(s) (4675). However, and without limitation, air/gas(s) can also enter the compartment blower(s) (4665) after passing through the one or more compartment air flow filter(s) (4675). Without being limited, the compartment air flow filter(s) (4675) can be located in or at one or more of any suitable and effective location(s). According to FIG. 22, and without limitation, any suitable and effective air/gas(s) can enter the one or more compartment airflow filter(s) (4675), flow through one or more of any suitable compartment air inlet(s) (4745) or any other suitable conduit(s), to the one or more suitable compartment blower(s) (4665), and then flow through one or more of any suitable compartment flow tube(s) (4725) or any other suitable conduit(s), and into the one or more agent flow compartment(s) (4630).

Alternatively, and without limitation, the one or more compartment blower(s) (4665) can also be suitably and effectively mounted to, interfaced with, and/or located at, the one or more of the said agent outlet(s) (4670), where the compartment blower(s) (4665) can be configured in a manner known to those skilled in the art, to effectively vacuum and/or pull the air/gas(s) and deployed agent(s) (4510) through both the deployed agent generator(s) (4620) and/or the agent flow compartment(s) (4630). It is preferred, without limitation, that in this configuration at least the air/gas(s) that are supplied to the deployed agent generator(s) (4620) are effectively filtered by one or more air flow injection filter(s) (4603). It is more preferred, without limitation, that in this configuration at least the air/gas(s) that are supplied to the deployed agent generator(s) (4620) are effectively filtered by one or more air flow injection filter(s) (4603), and other air/gas(s) that may also be supplied to the agent flow compartment(s) (4630), is effectively filtered by one or more compartment air flow filter(s) (4675).

Without being limited, the air/gas(s) and deployed agent(s) (4510) can flow through one or more of the said connection conduit(s) (4645) that can connect, communicate, and/or terminate, with one or more of any suitable and effective hose connector(s) (4640), that can effectively connect and communicate with one or more additional suitable and effective hose connector(s) (4640) that effectively connect, removably connect, interface, removably interface, and/or communicate, with one or more of any suitable and effective airflow bulkhead fitting(s) (4680) such as, but not limited to, any that are known to those skilled in the art.

Also, and without being limited, the one or more said airflow bulkhead fitting(s) (4680) described in the present invention can include and communicate with at least one suitable and effective hose connector(s) (4640) that connects and communicates with at least one front fitting plate(s) (4650), all in a manner known to those skilled in the art. It is preferred, without limitation, that the said hose connector(s) (4640) are any suitable Tri-clamp adapter(s) and Tri-clamp connector(s) known to those skilled in the art.

In an even more detailed aspect of the present invention, and without being limited, the airflow bulkhead fitting(s) (4680) can include various part(s) and component(s) such as, but not limited to, at least one of any suitable and effective, front fitting plate(s) (4650), gasket(s) (4660), rear fitting plate(s) (4685), threaded bolt(s) (4655), and threaded nut(s) (4710). Without being limited, the front fitting plate(s) (4650) can interface with the at least one of any, wall(s) (4695), of and/or belonging to, one or more of any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520). It is preferred, without limitation that the at least one of any effective seal(s) and/or gasket(s) (4660) is effectively located between the front fitting plate(s) (4650) and the said wall(s) (4695). Without being limited, the various part(s) and component(s) such as, but not limited to, at least one of any suitable and effective, front fitting plate(s) (4650), gasket(s) (4660), rear fitting plate(s) (4685), threaded bolt(s) (4655), and threaded nut(s) (4710), can be any suitable and effective, size(s), design(s), shape(s), geometry(s), length(s), width(s), height(s), and/or thickness(s), and can have any suitable and effective thread pattern(s) and design(s) known in the art, and use any suitable and effective materials for their construction.

Without being limited, one or more of any effectively threaded rod, bolt, and/or screw, hole(s) (not shown) of any suitable size(s) and depth(s), are effectively located in the front fitting plate(s) (4650), so that one or more of any effective threaded rod(s), bolt(s), and/or screw(s) (Herein called "Threaded Bolt(s)") (4655) can protrude from the rear fitting plate(s) (4685) located on the other side of the said wall(s) (4695) and through the one or more wall hole(s) (4690) and into and/or through the one or more front fitting plate(s) (4650).

Also, and without being limited, one or more of any suitable, plate(s), bar(s), and/or support(s) (Herein called "Rear Fitting Plate(s)") (4685) are suitably and effectively located, preferably and without limitation, directly opposed to the front fitting plate(s) (4650), on the other side of the wall(s) (4695) from the front fitting plate(s) (4650). Also, and without being limited, one or more of any threaded bolt(s) (4655) with any effective length(s), protrude from the rear fitting plate(s) (4685) in any effective manner know to those skilled in the art, and through the one or more suitable wall hole(s) (4690) and gasket(s) (4660), and screw and/or thread any effective distance(s) into and/or through the one or more said threaded rod, bolt, and/or screw, hole(s) (not shown), located in the front fitting plate(s) (4685) located on the other side of the wall(s) (4695) from the rear fitting plate(s) (4685). It is preferred, without limitation, that the front fitting plate(s) (4685) are located on the same side(s) of the one or more wall(s) (4695) as the agent dispenser(s) (4505) and the agent flow compartment(s) (4630). It is also preferred, without limitation, that the threaded bolt(s) (4655) are fixed into any suitable and effective position, and cannot turn, as they protrude from the rear fitting plate(s) (4685), all in a manner known to those skilled in the art.

Additionally, and without being limited, the rear fitting plate(s) (4685), threaded bolt(s) (4655), and front fitting plate(s) (4685) are designed in a manner known to those skilled in the art, so that one or more of any suitable nut(s) (4710) can be threaded onto the threaded bolt(s) (4655) and mechanically tightening the nut(s) (4710) from the side of the front fitting plate(s) (4685), causes the rear fitting plate(s) (4685) and the front fitting plate(s) (4685) to tighten effectively against the said wall(s) (4695) and at least one hermetic seal(s) to form against the wall(s) (4695) with the said gasket(s) (4660), all in a manner known to those skilled in the art. Any suitable and effective thread pattern(s) can be used for the various said part(s) and component(s).

Referring to FIGS. 16, 17, 19, and 21, and without being limited, any air/gas(s) flow and/or deployed agent(s) (4510) that is circulated within and/or through the one or more of any, location(s), room(s), enclosure(s), space(s), part(s), component(s), structure(s), and/or conduit(s), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), vent bypass system(s) (4415), and/or air return ducts (4520), can be effectively flowed, moved, and/or circulated through, the one or more of any agent dispenser(s) (4505), and more specifically through one or more of any suitable and effective part(s) and component(s) of the one or more agent dispenser(s) (4505), and even more specifically through one or more of any, agent generator blower(s) (4700), deployed agent generator(s) (4620), agent flow compartment(s) (4630), compartment blower(s) (4665), agent outlet(s) (4670), connection conduit(s) (4645), and/or airflow bulkhead fitting(s) (4680), that are a part of and/or communicate with one or more of any agent dispenser(s) (4505).

According to FIGS. 16, 17, 19, and 21, and without limitation, one or more of any suitable and effective, pipe(s), conduit(s), and/or hose(s) (Herein called "Agent Dispenser Inlet Connection(s)" (4715), can also suitably and effectively connect and communicate with one or more of any agent dispenser(s) (4505) in a manner known to those skilled in the art, and supply the said agent dispenser(s) (4505) with any suitable and effective supply and/or flow of any air/gas(s) and/or deployed agent(s) (4510). It is preferred, without limitation, that the supply and/or flow of the said air/gas(s) and/or deployed agent(s) (4510) are sourced from the one or more of any suitable and effective, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520). Also, and without being limited, the said supply and/or flow of the said air/gas(s) and/or deployed agent(s) (4510) can be supplied to and flow through the one or more deployed agent generator(s) (4620) and/or agent flow compartment(s)

(4630), where the deployed agent(s) (4510) and air/gas(s) can then flow through and/or out of, one or more location(s), outlet(s), part(s), and/or component(s) such as, but not limited to any, connection conduit(s) (4645). Without being limited the one or more connection conduit(s) (4645) can suitably and effectively connect and communicate with one one or more of any suitable and effective, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), all in a manner known to those skilled in the art.

It is preferred, without limitation, that the one or more of any agent dispenser(s) (4505) are therefore hermetically sealed and connected to the said one or more of any suitable and effective, location(s), room(s), enclosure(s), space(s), part(s), equipment(s), component(s), structure(s), conduit(s), HVAC parts and equipment(s) (4465), HVAC unit(s) (4610), and/or air duct(s) (4455), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), and at least one effective communicating and closed loop air/gas(s) flow system(s) is formed, where the said flow of air/gas(s) and/or deployed agent(s) (4510) is moved, circulated, and flowed, through the one or more of the said any, location(s), room(s), enclosure(s), space(s), part(s), equipment(s), component(s), structure(s), conduit(s), HVAC parts and equipment(s) (4465), HVAC unit(s) (4610), and/or air duct(s) (4455), in addition to also being moved, circulated, and flowed, effectively and suitably through the one or more of any agent dispenser(s) (4505), and even more preferably and without limitation, at least through either and/or both of the one or more, agent flow compartment(s) (4630) and/or the deployed agent generator(s) (4620), as well as any vent bypass system(s) (4415) that are connected to the closed, effectively sealed, and communicating system of any of the said, location(s), room(s), enclosure(s), space(s), part(s), equipment(s), component(s), structure(s), conduit(s), HVAC parts and equipment(s) (4465), HVAC unit(s) (4610), and/or air duct(s) (4455), through which the air/gas(s) and/or deployed agent(s) can move, circulate, and flow through.

Alternatively, and referring to FIGS. 18 and 20, and without limitation, the one or more of any agent dispenser(s) (4505) can be hermetically sealed and connected to the said one or more of any suitable and effective, location(s), room(s), enclosure(s), space(s), part(s), equipment(s), component(s), structure(s), conduit(s), HVAC parts and equipment(s) (4465), HVAC unit(s) (4610), and/or air duct(s) (4455), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), and at least one effective communicating and open loop air/gas(s) flow system(s) is formed, where the said flow of air/gas(s) and/or deployed agent(s) (4510) is moved, circulated, and flowed, through the one or more of the said any, location(s), room(s), enclosure(s), space(s), part(s), equipment(s), component(s), structure(s), conduit(s), HVAC parts and equipment(s) (4465), HVAC unit(s) (4610), and/or air duct(s) (4455), in addition to also being moved, circulated, and flowed, effectively and suitably through the one or more of any agent dispenser(s) (4505), and even more preferably and without limitation, at least through either and/or both of the one or more, agent flow compartment(s) (4630) and/or the deployed agent generator(s) (4620), as well as any vent bypass system(s) (4415), where the air/gas(s) and deployed agent(s) (4510) is eventually flowed and/or vented into any environment, area, and/or atmosphere, at one or more of any suitable and effective location(s) that is outside of and/or separate from the said open loop air/gas(s) flow system(s).

Referring to FIGS. 16-17, 19, and 23, and according to an embodiment, and without limitation, an enhanced vent bypass system(s) (4415) (4790) is shown, where the enhanced vent bypass system (4415) (4790) can also include and communicate with one or more of any, including one or more of any suitable and effective combination(s) of any, suitable and effective, part(s), component(s), and/or equipment(s), such as, but not limited to any, means to filter any air/gas(s) (4600) including any means to filter airborne chemicals from any air/gas(s), means to flow, blow, or move any air/gas(s) (4535), means to heat any air/gas(s) (4740), means to dehumidify any air/gas(s) (4800), and/or agent dispenser(s) (4505). Without being limited, the one or more said part(s), component(s), and/or equipment(s), can be connected and/or located in any suitable and effective order(s), and be activated and/or used for one or more of any purposes, and at any suitable and effective time(s), and for any effective duration of time(s). Without limitation, the said part(s), component(s), and/or equipment(s), can also suitably and effectively connect and communicate with one or more of any conduit(s) and/or hose(s) (40)(4380) that connect with and/or are a part of any enhanced vent bypass system(s) (4415) (4790). Also without being limited, the one or more conduit(s) or hose(s) (40)(4380) can form, take the place of, and/or function as, the one or more agent dispenser inlet connection(s) (4715) and connection conduit(s) (4645) that can connect and communicate with the one or more agent dispenser(s) (4505).

Figure 23:
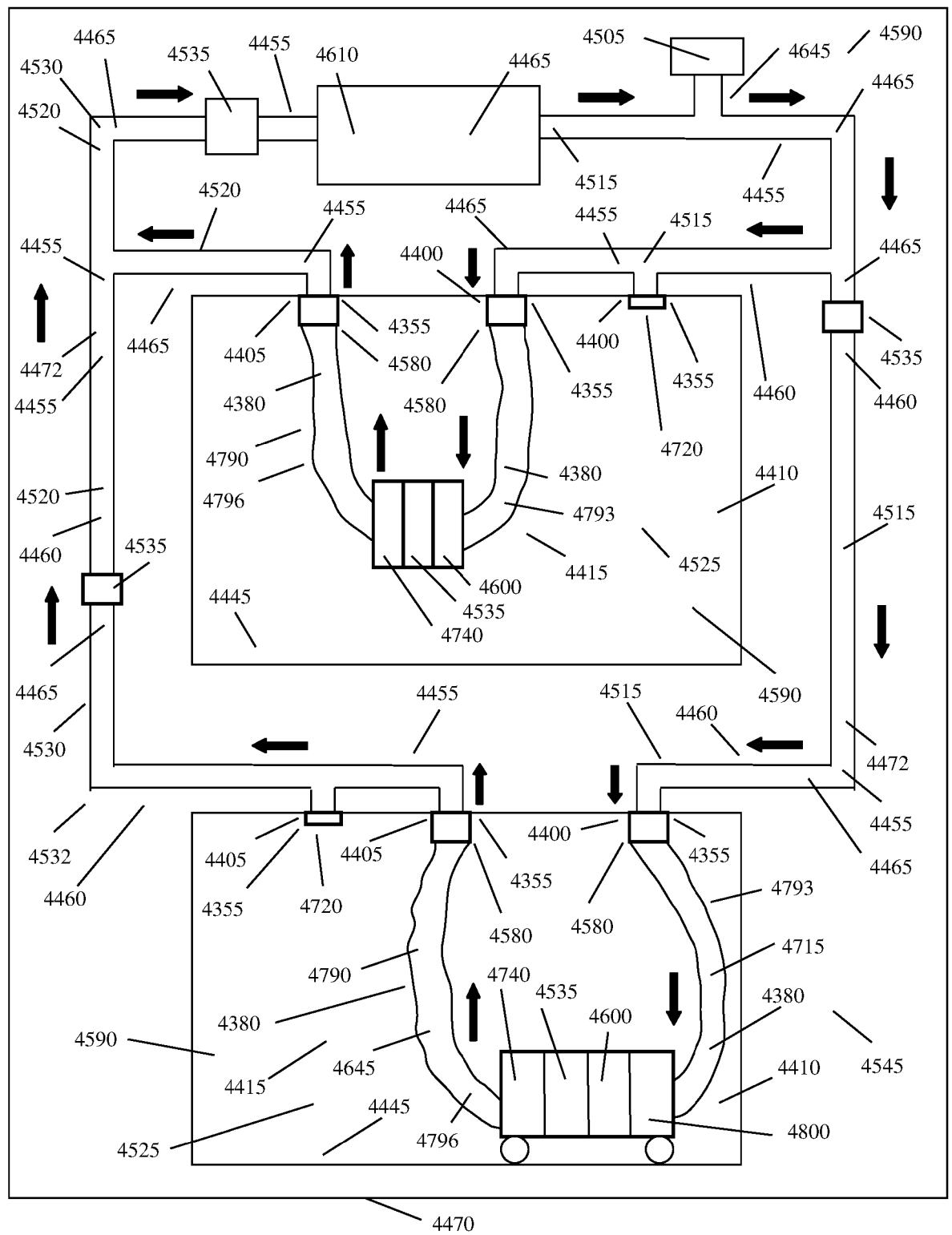
FIG. 23 is a schematic diagram of an enhanced vent bypass system used in a multi-story building, where hoses and/or conduits that connect to one part of the vent bypass system that covers and seals the air/gas(s) vent(s) in an area(s) and/or room(s) is first connected to and communicates with one or more of any, air filter(s), blower(s), heater(s), and/or agent dispensor(s), and is then connected and sealed to the other means to cover and seal the other air/gas(s) vent(s) in the room(s)/area(s).

More specifically, and referring to FIG. 23, and without limitation, one or more enhanced vent bypass system(s) (4790) can be used in any building(s) and structure(s) including, but not limited to any multi-story building(s) (4470), where one or more hoses and/or conduits (40)(4380) (Herein called "Air/gas(s) Supply Conduit(s)") (4793), that connect to one part of an enhanced vent bypass system (4790) that covers and seals any air/gas(s) vent(s) (4400) that supply air/gas(s) in and/or into any area(s) and/or room(s) (4410) is first connected to and communicates with one or more of any, air filter(s) (4600), blower(s) (4535), air/gas(s) flow heater(s) (4740), dehumidifier(s) (4800), and/or agent dispensor(s) (4505), in any suitable and effective combination(s), and is then connected and sealed to one or more hoses and/or conduits (40)(4380) (Herein called "Air/gas(s) Exit Conduit(s)") (4796), that connects to another part of the enhanced vent bypass system(s) (4790) that covers and seals the air/gas(s) vent(s) (4405) that vent, remove, and/or provide an exit for air/gas(s) to leave, any area(s) and/or room(s) (4410).

In one example, and without being limited, at least one suitable and effective duct fan(s) (4535) is suitably and effectively connected to and communicates with the vent bypass system (4415), and more specifically with the various conduit(s) or hose(s) (40)(4380) of the vent bypass system (4415). The said duct fan(s) (4535) are operated at least during the deployment of the deployed agent(s) (4510) by the agent dispenser(s) (4505), and assist with moving or flowing air/gas(s) and/or the deployed agent(s) (4510) effectively through various location(s), room(s), enclosure(s), space(s), part(s), equipment(s), component(s), structure(s), conduit(s), HVAC parts and equipment(s) (4465), HVAC unit(s) (4610), and/or air duct(s) (4455), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520).

In another example, and without being limited, after the deployed agent(s) (4510) are finished being administered by the agent dispenser(s) (4505), at least one of any suitable and effective, duct fan(s) (4535), air heater(s) (4740), dehumidifier(s) (4800), and/or air filter(s) such as, but not limited to any, airborne chemical absorbing filter(s) and/or HEPA filter(s), can be suitably and effectively connected to and communicate with the one or more of any conduit(s) or hose(s) (40)(4380) of the vent bypass system (4415). Without limitation, the said duct fan(s) (4535), dehumidifier(s) (4800), and/or air/gas(s) heater(s) is operated and effectively flows and moves air/gas(s), and preferably and without limitation, effectively heated air/gas(s), through various location(s), room(s), enclosure(s), space(s), part(s), equipment(s), component(s), structure(s), conduit(s), HVAC parts and equipment(s) (4465), HVAC unit(s) (4610), and/or air duct(s) (4455), such as, but not limited to any, air duct(s) (4455), air supply duct(s) (4515), air duct system(s) (4460), HVAC part(s) and equipment(s) (4465) and/or HVAC unit(s) (4610), area(s), zone(s), area(s) of air duct(s) (4455), zone(s) of air duct(s) (4455), enclosure(s) (not shown), room(s) (4410), air shaft(s) (4472), air/gas(s) entry vent(s) (4400), air/gas exit vent(s) (4405), hose(s) (40)(4380), vent bypass system(s) (4415), orifice(s), and/or air return ducts (4520), for purposes including, but not limited to effectively, drying, dehumidifying, and/or removing any, gas(s), chemical(s), humidity, and/or vapor(s), from these various, surface(s), space(s), location(s), part(s), and/or equipment(s). Without being limited, the one or more duct fan(s) (4535) and/or air heater(s) (4740) can be operated for one or more of any suitable and effective duration(s) of time. Also without being limited, the duct heater(s) can heat the air/gas(s) that are flowed and moved, to any suitable and effective temperatures, but at least preferably, and without limitation, to any effective temperature above 70 degree Fahrenheit.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. A method of preventing gas flow into and out of an enclosed space through at least two vents of a HVAC system, such that the enclosed space may be decontaminated with disinfection equipment inside the enclosed space, comprising the steps of:

sealing at least one entry vent of a HVAC system such that no gas from the entry vent enters the enclosed space;

sealing at least one exit vent of said HVAC system such that no gas in the enclosed space exits through the at least one exit vent;

connecting one end of at least one tubular member to the at least one entry vent, such that gas flows into said one end of said tubular member; and connecting an opposing end of said at least one tubular member to said at least one exit vent, such that the gas flows directly from said at least one entry vent into said at least one exit vent through said at least one tubular member.

2. The method of preventing gas flow into and out of an enclosed space through at least two vents of a HVAC system of claim 1, further comprising the step of:

providing at least one first vent cover having a first sealing ring formed at least around a perimeter for sealing to the at least one entry vent, at least one first bypass hole formed through said at least one first vent cover; and providing at least one second vent cover having a second peripheral sealing ring formed at least around a perimeter for sealing to the at least one exit vent, at least one second bypass hole formed through said at least one second vent cover.

3. The method of preventing gas flow into and out of an enclosed space through at least two vents of a HVAC system of claim 2, further comprising the step of:

connecting a tube flange of one of said at least one first vent cover covering one of the at least one entry vent to said one end of said at least one tubular member; and connecting a tube flange of one of said at least one second vent cover covering one of the at least one exit vent to said opposing end of said at least one tubular member.

4. The method of preventing gas flow into and out of an enclosed space through at least two vents of a HVAC system of claim 1, further comprising the step of:

providing said at least one tubular member as being flexible.

5. A method of preventing gas flow into and out of an enclosed space through at least two vents of a HVAC system, such that the enclosed space may be decontaminated with disinfection equipment inside the enclosed space, comprising the steps of:

sealing at least one entry vent of a HVAC system such that no gas from the entry vent enters the enclosed space;

sealing at least one exit vent of said HVAC system such that no gas in the enclosed space exits through the at least one exit vent;

connecting one end of at least one tubular member to the at least one entry vent, such that gas flows into said one end of said tubular member; and connecting an opposing end of said at least one tubular member to said at least one exit vent, such that the gas flows directly from said at least one entry vent into said at least one exit vent through said at least one tubular member, said at least one tubular member keeping the HVAC system substantially balanced.

6. The method of preventing gas flow into and out of an enclosed space through at least two vents of a HVAC system of claim 5, further comprising the step of:

providing at least one first vent cover having a first sealing ring formed at least around a perimeter for sealing to the at least one entry vent, at least one first bypass hole formed through said at least one first vent cover; and providing at least one second vent cover having a second sealing ring formed at least around a perimeter for sealing to the at least one exit vent, at least one second bypass hole formed through said at least one second vent cover.

7. The method of preventing gas flow into and out of an enclosed space through at least two vents of a HVAC system of claim 6, further comprising the step of:
connecting a tube flange of one of said at least one first vent cover covering one of the at least one entry vent to said one end of said at least one tubular member; and
connecting a tube flange of one of said at least one second vent cover covering one of the at least one exit vent to said opposing end of said at least one tubular member.

8. The method of preventing gas flow into and out of an enclosed space through at least two vents of a HVAC system of claim 5, further comprising the step of:
providing said at least one tubular member as being flexible.

9. A method of preventing gas flow into and out of an enclosed space through at least two vents of a HVAC system, such that the enclosed space may be decontaminated with disinfection equipment inside the enclosed space, comprising the steps of:
sealing at least one entry vent of a HVAC system such that no gas from the entry vent enters the enclosed space;
sealing at least one exit vent of said HVAC system such that no gas in the enclosed space exits through the at least one exit vent;
connecting one end of at least one tubular member to the at least one entry vent, such that gas flows into said one end of said tubular member; and
connecting an opposing end of said at least one tubular member to said at least one exit vent, such that the gas flows directly from said at least one entry vent into said at least one exit vent through said at least one tubular member, a flow of gas bypassing circulating through the enclosed space and passing through said at least one tubular member back into the HVAC system, said at least one tubular member keeping the HVAC system substantially balanced.

10. The method of preventing gas flow into and out of an enclosed space through at least two vents of a HVAC system of claim 9, further comprising the step of:
providing at least one first vent cover having a first sealing ring formed at least around a perimeter for sealing to the at least one entry vent, at least one first bypass hole formed through said at least one first vent cover; and
providing at least one second vent cover having a second peripheral sealing ring formed at least around a perimeter for sealing to the at least one exit vent, at least one second bypass hole formed through said at least one second vent cover.

11. The method of preventing gas flow into and out of an enclosed space through at least two vents of a HVAC system of claim 10, further comprising the step of:
connecting a tube flange of one of said at least one first vent cover covering one of the at least one entry vent to said one end of said at least one tubular member; and
connecting a tube flange of one of said at least one second vent cover covering one of the at least one exit vent to said opposing end of said at least one tubular member.

12. The method of preventing gas flow into and out of an enclosed space through at least two vents of a HVAC system of claim 9, further comprising the step of:
providing said at least one tubular member as being flexible.

* * * * *